United States Patent
Cervin et al.

(10) Patent No.: US 7,745,184 B2
(45) Date of Patent: Jun. 29, 2010

(54) PROCESS FOR THE BIOLOGICAL PRODUCTION OF 1,3-PROPANEDIOL WITH HIGH YIELD

(75) Inventors: Marguerite A. Cervin, Redwood City, CA (US); Philippe Soucaille, Deyme (FR); Fernando Valle, Burlingame, CA (US)

(73) Assignees: E. I. du Pont de Nemours and Co., Wilmington, DE (US); Genencor International Inc., Palo Alto, CA (US)

( * ) Notice: Subject to any disclaimer, the term of this patent is extended or adjusted under 35 U.S.C. 154(b) by 103 days.

(21) Appl. No.: 12/053,991

(22) Filed: Mar. 24, 2008

(65) Prior Publication Data

US 2008/0176302 A1    Jul. 24, 2008

Related U.S. Application Data

(62) Division of application No. 10/680,286, filed on Oct. 6, 2003, now Pat. No. 7,371,558.

(51) Int. Cl.
   C12P 7/18       (2006.01)
   C12P 21/06      (2006.01)
   C12Q 1/68       (2006.01)
   C12N 1/21       (2006.01)
   C12N 15/74      (2006.01)
   C07H 21/04      (2006.01)

(52) U.S. Cl. ..................... 435/158; 435/6; 435/69.1; 435/252.33; 435/488; 536/23.2

(58) Field of Classification Search .............. None
See application file for complete search history.

(56) References Cited

U.S. PATENT DOCUMENTS

| 5,686,276 | A  | 11/1997 | Laffend et al. |
|---|---|---|---|
| 6,013,494 | A  | 1/2000 | Nakamura et al. |
| 6,136,576 | A  | 10/2000 | Diaz-Torres et al. |
| 6,432,686 | B1 | 8/2002 | Bulthuis et al. |
| 6,472,169 | B1 | 10/2002 | Frost et al. |
| 6,962,794 | B2 | 11/2005 | Valle et al. |
| 7,132,527 | B2 | 11/2006 | Payne et al. |
| 2002/0168654 | A1 | 11/2002 | Maranas et al. |
| 2005/0208615 | A1 | 9/2005 | Wilkins et al. |

FOREIGN PATENT DOCUMENTS

| EP | 1170376 A1 | 1/2002 |
|---|---|---|
| WO | 9634961 | 11/1996 |
| WO | 9635796 | 11/1996 |
| WO | 9821339 | 5/1998 |
| WO | 9821341 | 5/1998 |
| WO | 9928480 | 6/1999 |
| WO | 01/12833 A2 | 2/2001 |
| WO | 0112833 A2 | 2/2001 |

OTHER PUBLICATIONS

De Reuse et al., The ptsH, ptsI, and crr Genes of the *Escherichia coli* Phosphoenolpyruvate-dependent Phosphotransferase System: A Complex Operon With Several Modes of Transcription, Journal of Bacteriology, 1988, vol. 170:3827-3837.

Postma et al., Phosphoenolpyruvate: Carbohydrate Phosphotranferase Systems of Bateria, Microbiological Reviews, 1993, vol. 57:543-594.

Search Report dated Aug. 16, 2007 for Corresponding European Patent Application No. 03777548.3

NCBI, General Identification No. 15802948, Perna, N.T. et al., Genome sequence of enterohemorrhagic *Escherichia coli* O157:H7 Nature 409 (6819), 529-533 (2001).

NCBI, General Identification No. 16130341, Riley, M. et al., *Escherichia coli* K-12: a cooperatively developed annotation snapshot—2005, Nucleic Acids Res. 34(1), 1-9 (2006).

NCBI, General Identification No. 26248792, Welch R.A. et al., Proc. Natl. Acad. Scii. U.S.A. 99 (26), 17020-17024 (2002) Extensive mosaic structure revealed by the . . . .

NCBI, General Identification No. 15832541, Hayashi, T. et al., DNA Res. 8(1), 11-22 (2001), Complete genome sequence of enterohemorrhagic *Escherichia* coil . . . .

NCBI, General Identification No. 15802949, Perna, N.T. et al., Nature 409 (6819), 529-33 (2001), Genome sequence of enterohemorrhagic *Escherichia coli* O157:H7.

NCBI, General Identification No. 16130342, Riley, M. et al., Nucleic Acids Res. 34(1), 1-9 (2006), *Escherichia coli* K-12: a cooperatively developed annotation snapshot—2005.

NCBI, General Identification No. 26248793, Welch R.A. et al., Proc. Natl. Acad. Scii. U.S.A. 99 (26), 17020-17024 (2002), Extensive mosaic structure revealed by the . . . .

NCBI, General Identification No. 15832542, Hayashi, T. et al., DNA Res. 8(1), 11-22 (2001), Complete genome sequence of enterohemorrhagic *Escherichia* coil . . . .

NCBI, General Identification No. 15802950, Perna, N.T. et al., Genome sequence of enterohemorrhagic *Escherichia coli* O157:H7 Nature 409 (6819), 529-533 (2001).

(Continued)

*Primary Examiner*—Richard Hutson
*Assistant Examiner*—Iqbal H Chowdhury
(74) *Attorney, Agent, or Firm*—Lynne M. Christenbury

(57) ABSTRACT

The present invention provides a microorganism useful for biologically producing 1,3-propanediol from a fermentable carbon source at higher yield than was previously known. The complexity of the cofactor requirements necessitates the use of a whole cell catalyst for an industrial process that utilizes this reaction sequence to produce 1,3-propanediol. The invention provides a microorganism with disruptions in specified genes and alterations in the expression levels of specified genes that is useful in a higher yielding process to produce 1,3-propanediol.

4 Claims, 1 Drawing Sheet

OTHER PUBLICATIONS

Figure 1:
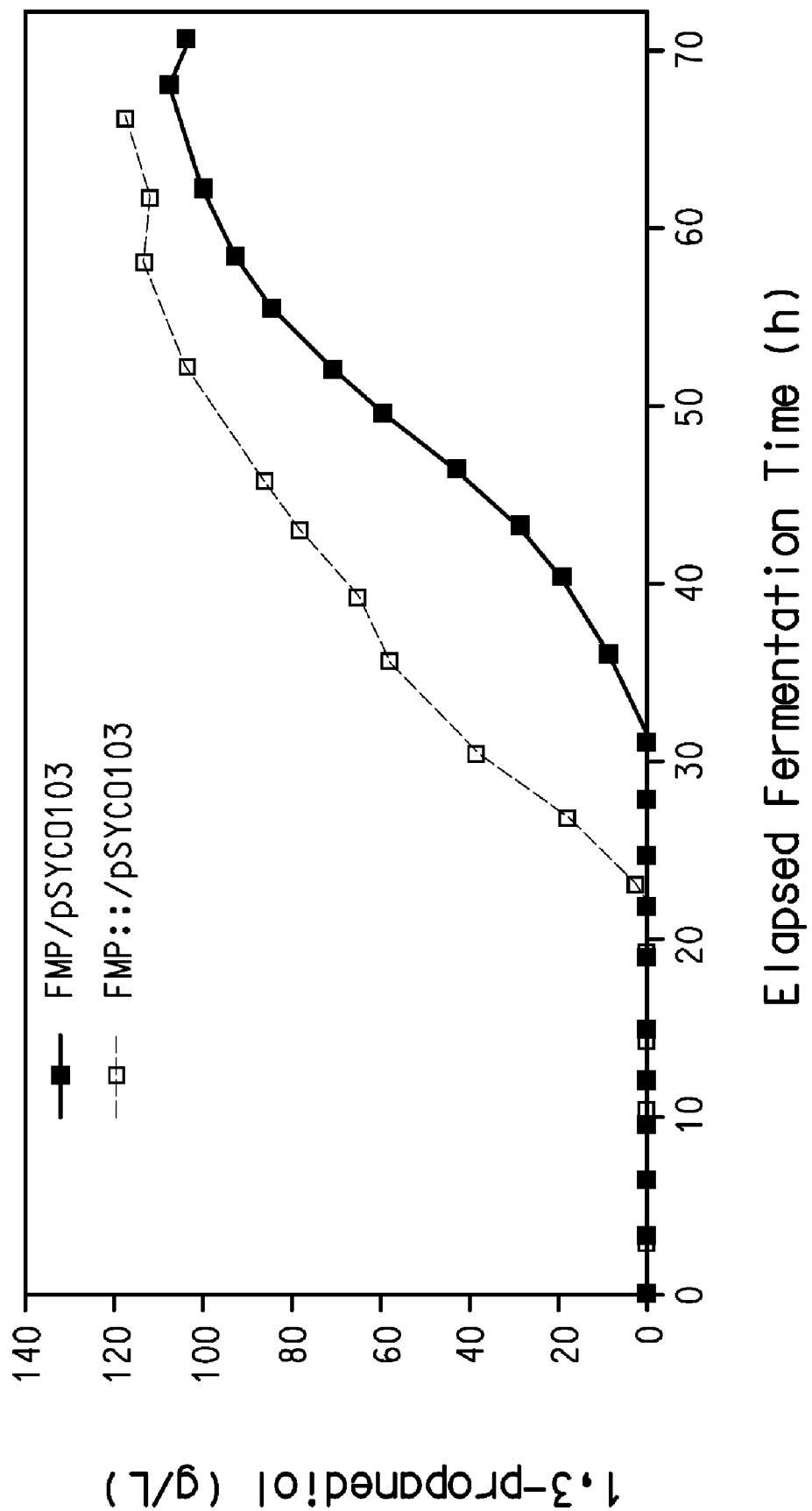

NCBI, General Identification No. 6130343, Riley, M. et al., Nucleic Acids Res. 34(1), 1-9 (2006), *Escherichia coli* K-12: a cooperatively developed annotation snapshot—20.

NCBI, General Identification No. 26248794, Welch R.A. et al., Proc. Natl. Acad. Scii. U.S.A. 99 (26), 17020-17024 (2002) Extensive mosaic structure revealed by the . . . .

NCBI, General Identification No. 15802930, Perna, N.T. et al., Genome sequence of enterohemorrhagic *Escherichia coli* 0157:H7 Nature 409 (6819), 529-533 (2001).

NCBI, General Identification No. 16130320, Riley, M. et al., Nucleic Acids Res. 34(1), 1-9 (2006), *Escherichia coli* K-12: a cooperatively developed annotation snapshot—2005.

NCBI, General Identification No. 26248769, Welch R.A. et al., Proc. Natl. Acad. Scii. U.S.A. 99 (26), 17020-17024 (2002) Extensive mosaic structure revealed by the . . . .

NCBI, General Identification No. 15832522, Hayashi, T. et al., DNA Res. 8(1), 11-22 (2001), Complete genome sequence of enterohemorrhagic *Escherichia* coil . . . .

NCBI, General Identification No. 15803482, Perna, N.T. et al., Genome sequence of enterohemorrhagic *Escherichia coli* 0157:H7 Nature 409 (6819), 529-533 (2001).

NCBI, General Identification No. 16130844, Riley, M. et al., Nucleic Acids Res. 34(1), 1-9 (2006), *Escherichia coli* K-12: a cooperatively developed annotation snapshot—2005.

NCBI, General Identification No. 26249364, Welch R.A. et al., Proc. Natl. Acad. Scii. U.S.A. 99 (26), 17020-17024 (2002) Extensive mosaic structure revealed by the . . . .

NCBI, General Identification No. 15833073, Hayashi, T. et al., DNA Res. 8(1), 11-22 (2001), Complete genome sequence of enterohemorrhagic *Escherichia* coil . . . .

NCBI, General Identification No. 15802193, Perna, N.T. et al., Genome sequence of enterohemorrhagic *Escherichia coli* 0157:H7 Nature 409 (6819), 529-533 (2001).

NCBI, General Identification No. 16129733, Riley, M. et al., *Escherichia coli* K-12: a cooperatively developed annotation snapshot—2005, Nucleic Acids Res. 34(1), 1-9 (2006).

NCBI, General Identification No. 26248038, Welch R.A. et al., Proc. Natl. Acad. Scii. U.S.A. 99 (26), 17020-17024 (2002) Extensive mosaic structure revealed by the . . . .

NCBI, General Identification No. 15831742, Hayashi, T. et al., DNA Res. 8(1), 11-22 (2001), Complete genome sequence of enterohemorrhagic *Escherichia* coil . . . .

NCBI, General Identification No. 15804972, Perna, N.T. et al., Genome sequence of enterohemorrhagic *Escherichia coli* 0157:H7 Nature 409 (6819), 529-533 (2001).

NCBI, General Identification No. 16132218, Riley, M. et al., *Escherichia coli* K-12: a cooperatively developed annotation snapshot—2005, Nucleic Acids Res. 34(1), 1-9 (2006).

NCBI, General Identification No. 26251294, Welch R.A. et al., Proc. Natl. Acad. Scii. U.S.A. 99 (26), 17020-17024 (2002) Extensive mosaic structure revealed by the . . . .

NCBI, General Identification No. 15834613, Hayashi, T. et al., DNA Res. 8(1), 11-22 (2001), Complete genome sequence of enterohemorrhagic *Escherichia* coil . . . .

NCBI, General Identification No. 15804552, Perna, N.T. et al., Genome sequence of enterohemorrhagic *Escherichia coli* 0157:H7 Nature 409 (6819), 529-533 (2001).

NCBI, General Identification No. 16131794, Riley, M. et al., *Escherichia coli* K-12: a cooperatively developed annotation snapshot—2005, Nucleic Acids Res. 34(1), 1-9 (2006).

NCBI, General Identification No. 26250729, Welch R.A. et al., Proc. Natl. Acad. Scii. U.S.A. 99 (26), 17020-17024 (2002) Extensive mosaic structure revealed by the . . . .

NCBI, General Identification No. 15834139, Hayashi, T. et al., DNA Res. 8(1), 11-22 (2001), Complete genome sequence of enterohemorrhagic *Escherichia* coil . . . .

NCBI, General Identification No. 15801909, Perna, N.T. et al., Genome sequence of enterohemorrhagic *Escherichia coli* 0157:H7 Nature 409 (6819), 529-533 (2001).

NCBI, General Identification No. 16129231, Riley, M. et al., *Escherichia coli* K-12: a cooperatively developed annotation snapshot—2005, Nucleic Acids Res. 34(1), 1-9 (2006).

NCBI, General Identification No. 26247599, Welch R.A. et al., Proc. Natl. Acad. Scii. U.S.A. 99 (26), 17020-17024 (2002) Extensive mosaic structure revealed by the . . . .

NCBI, General Identification No. 15831096, Hayashi, T. et al., DNA Res. 8(1), 11-22 (2001), Complete genome sequence of enterohemorrhagic *Escherichia* coil . . . .

NCBI, General Identification No. 5803555, Perna, N.T. et al., Genome sequence of enterohemorrhagic *Escherichia coli* 0157:H7 Nature 409 (6819), 529-533 (2001).

NCBI, General Identification No. 16130909, Riley, M. et al., *Escherichia coli* K-12: a cooperatively developed annotation snapshot—2005, Nucleic Acids Res. 34(1), 1-9 (2006).

NCBI, General Identification No. 26249576, Welch R.A. et al., Proc. Natl. Acad. Scii. U.S.A. 99 (26), 17020-17024 (2002) Extensive mosaic structure revealed by the . . . .

NCBI, General Identification No. 15833149, Hayashi, T. et al., DNA Res. 8(1), 11-22 (2001), Complete genome sequence of enterohemorrhagic *Escherichia* coil . . . .

NCBI, General Identification No. 15800822, Perna, N.T. et al., Genome sequence of enterohemorrhagic *Escherichia coli* 0157:H7 Nature 409 (6819), 529-533 (2001).

NCBI, General Identification No. 90111195, Riley, M. et al., *Escherichia coli* K-12: a cooperatively developed annotation snapshot—2005, Nucleic Acids Res. 34(1), 1-9 (2006).

NCBI, General Identification No. 26246985, Welch R.A. et al., Proc. Natl. Acad. Sci. U.S.A. 99 (26), 17020-17024 (2002) Extensive mosaic structure revealed by the . . . .

NCBI, General Identification No. 15802843, Perna, N.T. et al., Genome sequence of enterohemorrhagic *Escherichia coli* 0157:H7 Nature 409 (6819), 529-533 (2001).

NCBI, General Identification No. 16130231, Riley, M. et al., *Escherichia coli* K-12: a cooperatively developed annotation snapshot—2005, Nucleic Acids Res. 34(1), 1-9 (2006).

NCBI, General Identification No. 26248684, Welch R.A. et al., Proc. Natl. Acad. Sci. U.S.A. 99 (26), 17020-17024 (2002) Extensive mosaic structure revealed by the complete.

NCBI, General Identification No. 15833249, Hayashi, T. et al., DNA Res. 8(1), 11-22 (2001), Complete genome sequence of enterohemorrhagic *Escherichia* coil . . . .

NCBI, General Identification No. 15802844, Perna, N.T. et al., Genome sequence of enterohemorrhagic *Escherichia coli* 0157:H7 Nature 409 (6819), 529-533 (2001).

NCBI, General Identification No. 16130232, Riley, M. et al., *Escherichia coli* K-12: a cooperatively developed annotation snapshot—2005, Nucleic Acids Res. 34(1), 1-9 (2006).

NCBI, General Identification No. 26248686, Welch R.A. et al., Proc. Natl. Acad. Sci. U.S.A. 99 (26), 17020-17024 (2002) Extensive mosaic structure revealed by the . . . .

NCBI, General Identification No. 15832435, Hayashi, T. et al., DNA Res. 8(1), 11-22 (2001), Complete genome sequence of enterohemorrhagic *Escherichia* coil . . . .

NCBI, General Identification No. 15801728, Perna, N.T. et al., Genome sequence of enterohemorrhagic *Escherichia coli* 0157:H7 Nature 409 (6819), 529-533 (2001).

NCBI, General Identification No. 16129376, Riley, M. et al., *Escherichia coli* K-12: a cooperatively developed annotation snapshot—2005, Nucleic Acids Res. 34(1), 1-9 (2006).

NCBI, General Identification No. 26247703, Welch R.A. et al., Proc. Natl. Acad. Sci. U.S.A. 99 (26), 17020-17024 (2002) Extensive mosaic structure revealed by the . . . .

NCBI, General Identification No. 15831275, Hayashi, T. et al., DNA Res. 8(1), 11-22 (2001), Complete genome sequence of enterohemorrhagic *Escherichia* coil . . . .

NCBI, General Identification No. 15804128, Perna, N.T. et al., Genome sequence of enterohemorrhagic *Escherichia coli* 0157:H7 Nature 409 (6819), 529-533 (2001).

NCBI, General Identification No. 90111619, Riley, M. et al., *Escherichia coli* K-12: a cooperatively developed annotation snapshot—2005, Nucleic Acids Res. 34(1), 1-9 (2006).

NCBI, General Identification No. 26250230, Welch R.A. et al., Proc. Natl. Acad. Sci. U.S.A. 99 (26), 17020-17024 (2002) Extensive mosaic structure revealed by the . . . .

NCBI, General Identification No. 38704182, Hayashi, T. et al., DNA Res. 8(1), 11-22 (2001), Complete genome sequence of enterohemorrhagic *Escherichia* coil . . . .

NCBI, General Identification No. 15802264, Perna, N.T. et al., Genome sequence of enterohemorrhagic *Escherichia coli* 0157:H7 Nature 409 (6819), 529-533 (2001).

NCBI, General Identification No. 16129804, Riley, M. et al., *Escherichia coli* K-12: a cooperatively developed annotation snapshot—2005, Nucleic Acids Res. 34(1), 1-9 (2006).

NCBI, General Identification No. 26248116, Welch R.A. et al., Proc. Natl. Acad. Scii. U.S.A. 99 (26), 17020-17024 (2002) Extensive mosaic structure revealed by the . . . .

NCBI, General Identification No. 15804515, Perna, N.T. et al., Genome sequence of enterohemorrhagic *Escherichia coli* 0157:H7 Nature 409 (6819), 529-533 (2001).

NCBI, General Identification No. 16131764, Riley, M. et al., *Escherichia coli* K-12: a cooperatively developed annotation snapshot—2005, Nucleic Acids Res. 34(1), 1-9 (2006).

NCBI, General Identification No. 26250692, Welch R.A. et al., Proc. Natl. Acad. Sci. U.S.A. 99 (26), 17020-17024 (2002) Extensive mosaic structure revealed by the . . . .

NCBI, General Identification No. 15834105, Hayashi, T. et al., DNA Res. 8(1), 11-22 (2001), Complete genome sequence of enterohemorrhagic *Escherichia* coil . . . .

NCBI, General Identification No. 15804542, Perna, N.T. et al., Genome sequence of enterohemorrhagic *Escherichia coli* 0157:H7 Nature 409 (6819), 529-533 (2001).

NCBI, General Identification No. 90111668, Riley, M. et al., *Escherichia coli* K-12: a cooperatively developed annotation snapshot—2005, Nucleic Acids Res. 34(1), 1-9 (2006).

NCBI, General Identification No. 26250718, Welch R.A. et al., Proc. Natl. Acad. Sci. U.S.A. 99 (26), 17020-17024 (2002) Extensive mosaic structure revealed by the . . . .

NCBI, General Identification No. 38704215, Hayashi, T. et al., DNA Res. 8(1), 11-22 (2001), Complete genome sequence of enterohemorrhagic *Escherichia* coil . . . .

V. Gershanovitch et al. Repression of Inducible Enzyme Synthesis . . . , Molec. Gen. Genet. 153, 185-190, 1977.

T. Hesterkamp et al., A Reporter Gene Assay for Inhibitors . . . , J. Mol. Microbiol. Biotechnol, 1999, 1(2): 309-317.

D. W. Saffen et al., Sugar Transport by the Bacterial . . . , Journal of Biological Chemistry, vol. 262, No. 33, Issue Nov. 25, pp. 16241-16253, 1987.

Yea-Tyng Yang, Metabolic Flux Analysis of *Escherichia* coil . . . , Metabolic Engineering vol. 1, 26-34, 1999.

S. Alexeeva et al., Effects of Limited Aeration and . . . , Journal of Bacteriology, Sep. 2000, vol. 182, No. 17, pp. 4934-4940.

S. Tötemeyer et al., From famine to feast: the role of methylglyoxal . . . , Molecular Microbiology 27(3) 553-562, 1998.

C. Bausch et al., Sequence Analysis of the Gntll (Subsidiary) System for Gluconate . . . , Journal of Bacteriology, Jul. 1998, vol. 180, No. 14, pp. 3704-3710.

H. P. Schweizer et al., Structure and gene-polypeptide relationships . . . , Microbiology, 1997, 143, 1287-1297.

N. E. Altaras et al., Metabolic Engineering of a 1,2-Propanediol . . . , Applied & Environmental Microbiology, Mar. 1999, vol. 65, No. 3, pp. 1180-1185.

Rolf Daniel et al., Biochemistry of Coenzyme B12-dependent glycerol and diol dehydratases and organization of the encoding genes, FEMS Microbiology Reviews, vol. 22:553-566, 1999.

Tetsuo Toraya et al., A Reactivating Factor for Coenzyme B12-dependent Diol Dehydratase, J. Biol. Chem., vol. 274(6):3372-3377, 1999.

National Center for Biotechnology Information General Identifier No. 5069449, Accession No. AF026270, Oct. 19, 1999, The Control Region of the PDU/COB Regulon in *Salmonella typhimurium*, P. Chen et al.

Wang et al., Cloning, Sequence, and Disruption of the *Saccharomyces diastaticus* DAR1 Gene Encoding a Glycerol-3-Phosphate Dehydrogenase, J. Bact., vol. 176:7091-7095, 1994 .

Joakim Norbeck et al., Purification and Characterization of Two Isoenzymes of DL-Glycerol-3-phosphatase from *Saccharomyces cerevisiae*, J. Biol. Chem., vol. 271(23):13875-13881, 1996.

V. Hernandez-Montalvo et al., Characterization of Sugar Mixtures utilization by an *Escherichia coli* mutant devoid of the phosphotransferase system, Appl. Microbiol. Biotechnol., vol. 57:186-191, 2001.

Katrin Larsson et al., A gene encoding sn-glycerol 3-phosphate dehydrogenase (NAD+) complements an osmosensitive mutant of *Saccharomyces cerevisiae*, Mol. Microbiol., vol. 10:1101-1111, 1993.

Jacobus Albertyn et al., GPD1, Which Encodes Glycerol-3-Phosphate Dehydrogenase, Is Essential for Growth under Osmotic Stress in *Saccharomyces cerevisiae*, and Its Expression Is Regulated by the High-Osmolarity Glycerol Response Pathway, Mol. and Cellular Biology, vol. 14(6):4135-4144, 1994.

De Reuse et al., The ptsH, ptsI, and crr Genes of the *Escherichia coli* Phosphoenolpyruvate-Dependent Phosphotransferase System: A Complex Operon With Several Modes of Transcription, Journal of Bacteriology, 1988, vol. 170:3827-3837.

Postma et al., Phosphoenolpyruvate: Carbohydrate Phosphotransferase Systems of Bacteria, Microbiological Reviews, 1993, vol. 57:543-594.

Nternational Search Report Dated Mar. 14, 2006, International Application No. PCT/US03/31805, International Filing Date: Oct. 6, 2003.

PROCESS FOR THE BIOLOGICAL PRODUCTION OF 1,3-PROPANEDIOL WITH HIGH YIELD

DESCRIPTION OF RELATED APPLICATIONS

This application is a divisional of U.S. application Ser. No. 10/680,286, filed 6 Oct. 2003, which is still pending and which claims benefit of U.S. Provisional Application No. 60/416,192, filed 4 Oct. 2002, now expired.

FIELD OF INVENTION

This invention comprises a process for the bioconversion of a fermentable carbon source to 1,3-propanediol by a single microorganism.

BACKGROUND 1,3-Propanediol is a monomer having potential utility in the production of polyester fibers and the manufacture of polyurethanes and cyclic compounds.

A variety of chemical routes to 1,3-propanediol are known. For example ethylene oxide may be converted to 1,3-propanediol over a catalyst in the presence of phosphine, water, carbon monoxide, hydrogen and an acid, by the catalytic solution phase hydration of acrolein followed by reduction, or from compounds such as glycerol, reacted in the presence of carbon monoxide and hydrogen over catalysts having atoms from group VIII of the periodic table. Although it is possible to generate 1,3-propanediol by these methods, they are expensive and generate waste streams containing environmental pollutants.

It has been known for over a century that 1,3-propanediol can be produced from the fermentation of glycerol. Bacterial strains able to produce 1,3-propanediol have been found, for example, in the groups *Citrobacter, Clostridium, Enterobacter, Ilyobacter, Klebsiella, Lactobacillus*, and *Pelobacter*. In each case studied, glycerol is converted to 1,3-propanediol in a two step, enzyme catalyzed reaction sequence. In the first step, a dehydratase catalyzes the conversion of glycerol to 3-hydroxypropionaldehyde (3-HPA) and water, Equation 1. In the second step, 3-HPA is reduced to 1,3-propanediol by a NAD⁺-linked oxidoreductase, Equation 2. The 1,3-propanediol is not metabolized further and, as a result,

$$\text{Glycerol} \rightarrow \text{3-HPA} + \text{H}_2\text{O} \quad \text{(Equation 1)}$$

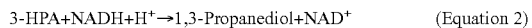

$$\text{3-HPA} + \text{NADH} + \text{H}^+ \rightarrow \text{1,3-Propanediol} + \text{NAD}^+ \quad \text{(Equation 2)}$$

accumulates in the media. The overall reaction consumes a reducing equivalent in the form of a cofactor, reduced β-nicotinamide adenine dinucleotide (NADH), which is oxidized to nicotinamide adenine dinucleotide (NAD⁺).

In *Klebsiella pneumonia, Citrobacter freundii*, and *Clostridium pasteurianum*, the genes encoding the three structural subunits of glycerol dehydratase (dhaB1-3 or dhaB, C and E) are located adjacent to a gene encoding a specific 1,3-propanediol oxidoreductase (dhaT). Although the genetic organization differs somewhat among these microorganisms, these genes are clustered in a group which also comprises orfX and orfZ (genes encoding a dehydratase reactivation factor for glycerol dehydratase), as well as orfY and orfW (genes of unknown function). The specific 1,3-propanediol oxidoreductases (dhaT's) of these microorganisms are known to belong to the family of type III alcohol dehydrogenases; each exhibits a conserved iron-binding motif and has a preference for the NAD⁺/NADH linked interconversion of 1,3-propanediol and 3-HPA. However, the NAD⁺/NADH linked interconversion of 1,3-propanediol and 3-HPA is also catalyzed by alcohol dehydrogenases which are not specifically linked to dehydratase enzymes (for example, horse liver and baker's yeast alcohol dehydrogenases (E.C. 1.1.1.1)), albeit with less efficient kinetic parameters. Glycerol dehydratase (E.C. 4.2.1.30) and diol [1,2-propanediol] dehydratase (E.C. 4.2.1.28) are related but distinct enzymes that are encoded by distinct genes. Diol dehydratase genes from *Klebsiella oxytoca* and *Salmonella typhimurium* are similar to glycerol dehydratase genes and are clustered in a group which comprises genes analogous to orfX and orfZ (Daniel et al., *FEMS Microbiol. Rev.* 22, 553 (1999); Toraya and Mori, *J. Biol. Chem.* 274, 3372 (1999); GenBank AF026270).

The production of 1,3-propanediol from glycerol is generally performed under anaerobic conditions using glycerol as the sole carbon source and in the absence of other exogenous reducing equivalent acceptors. Under these conditions, in e.g., strains of *Citrobacter, Clostridium*, and *Klebsiella*, a parallel pathway for glycerol operates which first involves oxidation of glycerol to dihydroxyacetone (DHA) by a NAD⁺-(or NADP⁺-) linked glycerol dehydrogenase, Equation 3. The DHA, following phosphorylation to dihydroxyacetone phosphate (DHAP) by a DHA kinase (Equation 4),

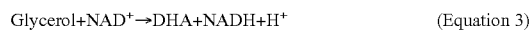

$$\text{Glycerol} + \text{NAD}^+ \rightarrow \text{DHA} + \text{NADH} + \text{H}^+ \quad \text{(Equation 3)}$$

$$\text{DHA} + \text{ATP} \rightarrow \text{DHAP} + \text{ADP} \quad \text{(Equation 4)}$$

becomes available for biosynthesis and for supporting ATP generation via e.g., glycolysis. In contrast to the 1,3-propanediol pathway, this pathway may provide carbon and energy to the cell and produces rather than consumes NADH.

In *Klebsiella pneumoniae* and *Citrobacter freundii*, the genes encoding the functionally linked activities of glycerol dehydratase (dhaB), 1,3-propanediol oxidoreductase (dhaT), glycerol dehydrogenase (dhaD), and dihydroxyacetone kinase (dhak) are encompassed by the dha regulon. The dha regulon, in *Klebsiella pneumoniae* and *Citrobacter freundii*, also encompasses a gene encoding a transcriptional activator protein (dhaR). The dha regulons from *Citrobacter* and *Klebsiella* have been expressed in *Escherichia coli* and have been shown to convert glycerol to 1,3-propanediol.

Neither the chemical nor biological methods described above for the production of 1,3-propanediol are well suited for industrial scale production since the chemical processes are energy intensive and the biological processes are limited to relatively low titer from the expensive starting material, glycerol. These drawbacks could be overcome with a method requiring low energy input and an inexpensive starting material such as carbohydrates or sugars, or by increasing the metabolic efficiency of a glycerol process. Development of either method will require the ability to manipulate the genetic machinery responsible for the conversion of sugars to glycerol and glycerol to 1,3-propanediol.

Biological processes for the preparation of glycerol are known. The overwhelming majority of glycerol producers are yeasts but some bacteria, other fungi, and algae are also known. Both bacteria and yeasts produce glycerol by converting glucose or other carbohydrates through the fructose-1,6-bisphosphate pathway in glycolysis or the Embden Meyerhof Parnas pathway. Dihydroxyacetone phosphate is converted to glycerol-3-phosphate by the action of glycerol-3-phosphate dehydrogenase, and glycerol-3-phosphate is converted to glycerol by the action of glycerol-3-phosphatase.

The gene encoding glycerol-3-phosphate dehydrogenase (DAR1, GPD1) has been cloned and sequenced from *S. dia-*

*staticus* (Wang et al., *J. Bact.* 176, 7091-7095 (1994)). The DAR1 gene was cloned into a shuttle vector and used to transform *E. coli* where expression produced active enzyme. Wang et al. (supra) recognize that DAR1 is regulated by the cellular osmotic environment but do not suggest how the gene might be used to enhance 1,3-propanediol production in a recombinant microorganism.

Other glycerol-3-phosphate dehydrogenase enzymes have been isolated: for example, sn-glycerol-3-phosphate dehydrogenase has been cloned and sequenced from *Saccharomyces cerevisiae* (Larason et al., *Mol. Microbiol.* 10, 1101 (1993)) and Albertyn et al. (*Mol. Cell. Biol.* 14, 4135 (1994)) teach the cloning of GPD1 encoding a glycerol-3-phosphate dehydrogenase from *Saccharomyces cerevisiae*. Like Wang et al. (supra), both Albertyn et al. and Larason et al. recognize the osmo-sensitivity of the regulation of this gene but do not suggest how the gene might be used in the production of 1,3-propanediol in a recombinant microorganism.

As with G3PDH, glycerol-3-phosphatase has been isolated from *Saccharomyces cerevisiae* and the protein identified as being encoded by the GPP1 and GPP2 genes (Norbeck et al., *J. Biol. Chem.* 271, 13875 (1996)). Like the genes encoding G3PDH, it appears that GPP2 is osmosensitive.

WO 9634961 and Hernandez-Montalvo et al. (*Appl. Microbiol. Biotechnol.* 57:186-191 (2001) describe *E. coli* strains that have "PTS" minus/glucose plus phenotypes. EP 1170376 A1 discloses deletion of a gene for NADH dehydratase II to improve energy efficiency. WO 2001016346 describes the utility of "aldehyde dehydrogenase A" and "aldehyde dehydrogenase B" for the production of 3-hydroxypropionic acid.

WO 9635796 (U.S. Pat. No. 5,686,276, E.I. du Pont de Nemours and Company ("DuPont")) discloses a method for the production of 1,3-propanediol from a carbon substrate other than glycerol or dihydroxyacetone (especially, e.g., glucose), using a single microorganism comprising a dehydratase activity. WO 9928480 (DuPont) discloses a similar method with advantages derived from expressing exogenous activities of one or both of glycerol-3-phosphate dehydrogenase and glycerol-3-phosphate phosphatase while disrupting one or both of endogenous activities glycerol kinase and glycerol dehydrogenase. WO 9821339 (U.S. Pat. No. 6,013,494, DuPont) describes a process for the production of 1,3-propanediol using a single microorganism comprising exogenous glycerol-3-phosphate dehydrogenase, glycerol-3-phosphate phosphatase, dehydratase, and 1,3-propanediol oxidoreductase (e.g., dhaT). WO 9821341 (U.S. Pat. No. 6,136,576, DuPont) discloses a method for the production of 1,3-propanediol comprising a recombinant microorganism further comprising a dehydratase and protein X (later identified as being a dehydratase reactivation factor peptide). WO 2001012833 (DuPont) describes an improvement to the process where a significant increase in titer (grams product per liter) is obtained by virtue of a non-specific catalytic activity (distinguished from 1,3-propanediol oxidoreductase encoded by dhaT) to convert 3-hydroxypropionaldehyde to 1,3-propanediol. U.S. Ser. No. 10/420,587 (2003) (U.S. 60/374,931 (2002) DuPont)) discloses vectors and plasmids useful for the production of 1,3-propanediol. The DuPont applications are incorporated by reference in the instant specification as though set forth in their entirety herein.

The biological production of 1,3-propanediol requires glycerol as an intermediate substrate for a two-step sequential reaction in which a dehydratase enzyme (typically a coenzyme $B_{12}$-dependent dehydratase) converts glycerol to 3-hydroxypropionaldehyde, which is then reduced to 1,3-propanediol by a NADH- (or NADPH-) dependent oxidoreductase. The complexity of the cofactor requirements necessitates the use of a whole cell catalyst for an industrial process that utilizes this reaction sequence for the production of 1,3-propanediol.

A specific deficiency in the biological processes leading to the production of 1,3-propanediol from glucose has been the low yield of the product achieved via fermentation. WO 2001012833 (DuPont) describes weight yields of 1,3-propanediol from glucose within the range of 24% and 35%. The problem that remains to be solved is how to biologically produce 1,3-propanediol, with high yield and by a single microorganism, from an inexpensive carbon substrate such as glucose or other sugars.

SUMMARY OF THE INVENTION

Applicants have solved the stated problem. The present invention provides for bioconverting a fermentable carbon source to 1,3-propanediol at higher yield than previously obtained and with the use of a single microorganism. The yield obtained is greater than 35%, and preferably greater than 40%. Glucose is used as a model substrate and *Escherichia coli* is used as the model host microorganism with the useful genetic modifications and disruptions detailed herein.

Applicants have provided an *E. coli* strain comprising:
  a) a disrupted endogenous phosphoenolpyruvate-glucose phosphotransferase system preventing expression of active PEP-glucose phosphotransferase system proteins;
  b) an up regulated endogenous galP gene encoding active galactose-proton symporter;
  c) an up regulated endogenous glk gene encoding active glucokinase; and
  d) a down regulated endogenous gapA gene encoding active glycerolaldehyde 3-phosphate dehydrogenase.

Applicants have also provided an *E. coli* strain described above wherein the disrupted endogenous phosphoenolpyruvate-glucose phosphotransferase system comprises one or more of
  a1) a disrupted endogenous ptsH gene preventing expression of active phosphocarrier protein;
  a2) a disrupted endogenous ptsI gene preventing expression of active phosphoenolpyruvate-protein phosphotransferase; and
  a3) a disrupted endogenous crr gene preventing expression of active glucose-specific IIA component.

The *E. coli* embodiments described above can further comprise one or more of
  e) a disrupted endogenous arcA gene preventing expression of active aerobic respiration control protein;
  f) an up regulated endogenous ppc gene encoding active phosphoenolpyruvate carboxylase;
  g) an up regulated endogenous btuR gene encoding active cob(I)alamin adenosyltransferase; and
  h) an up regulated yqhD gene encoding active alcohol dehydrogenase.

The *E. coli* embodiments described above can further comprise one or more of
  i) a disrupted endogenous mgsA gene preventing the expression of active methylglyoxal synthase;
  j) a disrupted endogenous ackA gene preventing the expression of active acetate kinase;
  k) a disrupted endogenous pta gene preventing the expression of active phosphotrasacetylase;
  l) a disrupted endogenous aldA gene preventing the expression of active aldehyde dehydrogenase A; and m) a disrupted endogenous aldB gene preventing the expression of active aldehyde dehydrogenase B.

The *E. coli* embodiments described above can further comprise one or more of:

n) a disrupted endogenous edd gene preventing expression of active phosphogluconate dehydratase;
o) a disrupted endogenous glpK gene preventing expression of active glycerol kinase; and
p) a disrupted endogenous gldA gene preventing expression of active NADH-dependent glycerol dehydrogenase.

Additionally, 1,3-propanediol can be bioproduced by contacting an *E. coli* strain described herein with a suitable carbon substrate such as glucose under suitable conditions for fermentation. In addition, 1,3-propanediol can be bioproduced by contacting an *E. coli* strain described herein, the *E. coli* strain further comprising an active:

(i) glycerol-3-phosphate dehydrogenase;
(ii) glycerol-3-phosphatase;
(iii) dehydratase; and
(iv) dehydratase reactivating activity;

with a suitable carbon substrate under suitable conditions.

Additionally, any of the embodiments disclosed above may also include the constructs pSYCO101, pSYCO103, pSYCO106, pSYCO109 or their corresponding nucleotide sequences SEQ ID NOs:65, 66, 67, or 68.

BRIEF DESCRIPTION OF THE DRAWINGS SEQUENCE DESCRIPTIONS, AND BIOLOGICAL DEPOSITS

The invention can be more fully understood from the following detailed description, the FIG. 1, the accompanying sequence listing and descriptions, and biological deposits that form parts of this application.

FIG. 1 shows 1,3-propanediol production compared as between two fermentations run essentially as described in GENERAL METHODS. In one case, the strain used was FMP'::Km/pSYCO103. In the other case, the strain used was FMP/pSYCO103.

The 68 sequence descriptions and the sequence listing attached hereto comply with the rules governing nucleotide and/or amino acid sequence disclosures in patent applications as set forth in 37 C.F.R. §1.821-1.825 ("Requirements for patent Applications Containing Nucleotide Sequences and/or Amino Acid Sequence Disclosures—the Sequence Rules") and will be consistent with World Intellectual Property Organization (WIPO) Standard ST.25 (1998) and the sequence listing requirements of the EPO and PCT (Rules 5.2 and 49.5 (a-bis), and Section 208 and Annex C of the Administration Instructions). The Sequence Descriptions contain the one letter code for nucleotide sequence characters and the three letter codes for amino acids as defined in conformity with the IUPAC-IYUB standards described in *Nucleic Acids Res.* 13, 3021-3030 (1985) and in the *Biochemical Journal* 219, 345-373 (1984) which are herein incorporated by reference.

SEQ ID NO:1 is the partial nucleotide sequence of pLox-Cat27 encoding the loxP511-Cat-loxP511 cassette.

SEQ ID NO:2-3 are oligonucleotide primers used to construct the arcA disruption.

SEQ ID NOs:4-5 are oligonucleotide primers used to confirm disruption of arcA.

SEQ ID NO:6 is the partial nucleotide sequence of pLox-Cat1 encoding the loxP-Cat-loxP cassette.

SEQ ID NOs:7-8 are oligonucleotide primers used to construct pR6KgalP, the template plasmid for trc promoter replacement of the chromosomal galP promoter.

SEQ ID NOs:9-10 are oligonucleotide primers used to construct pR6Kglk, the template plasmid for trc promoter replacement of the chromosomal glk promoter.

SEQ ID NO:11 is the nucleotide sequence of the loxP-Cat-loxP-Trc cassette.

SEQ ID NOs:12-13 are oligonucleotide primers used to confirm integration of SEQ ID NO:11 for replacement of the chromosomal galP promoter.

SEQ ID NOs:14-15 are oligonucleotide primers used to confirm integration of SEQ ID NO:11 for replacement of the chromosomal glk promoter.

SEQ ID NOs:16-17 are oligonucleotide primers used to construct the edd disruption.

SEQ ID NOs:18-19 are oligonucleotide primers used to confirm disruption of edd.

SEQ ID NOs:20 is the nucleotide sequence for the selected trc promoter controlling glk expression.

SEQ ID NOs:21 is the partial nucleotide sequence for the standard trc promoter.

SEQ ID NOs:22-23 are the oligonucleotide primers used for amplification of gapA.

SEQ ID NOs:24-25 are the oligonucleotide primers used to alter the start codon of gapA to GTG.

SEQ ID NOs:26-27 are the oligonucleotide primers used to alter the start codon of gapA to TTG.

SEQ ID NO:28 is the nucleotide sequence for the short 1.5 GI promoter.

SEQ ID NOs:29-30 are oligonucleotide primers used for replacement of the chromosomal gapA promoter with the short 1.5 GI promoter.

SEQ ID NO:31 is the nucleotide sequence for the short 1.20 GI promoter.

SEQ ID NO:32 is the nucleotide sequence for the short 1.6 GI promoter.

SEQ ID NOs:33-34 are oligonucleotide primers used for replacement of the chromosomal gapA promoter with the short 1.20 GI promoter.

SEQ ID NO:35 is the oligonucleotide primer with SEQ ID NO 33 that is used for replacement of the chromosomal gapA promoter with the short 1.6 GI promoter.

SEQ ID NOs:36-37 are oligonucleotide primers used to construct the mgsA disruption.

SEQ ID NOs:38-39 are oligonucleotide primers used to confirm disruption of mgsA.

SEQ ID NOs:40-41 are oligonucleotide primers used for replacement of the chromosomal ppc promoter with the short 1.6 GI promoter.

SEQ ID NO:42 is an oligonucleotide primer used to confirm replacement of the ppc promoter.

SEQ ID NOs:43-44 are oligonucleotide primers used for replacement of the chromosomal yciK-btuR promoter with the short 1.6 GI promoter.

SEQ ID NOs:45-46 are oligonucleotide primers used to confirm replacement of the yciK-btuR promoter.

SEQ ID NOs:47-48 are oligonucleotide primers used for replacement of the chromosomal yqhD promoter with the short 1.6 GI promoter.

SEQ ID NO:49 is an oligonucleotide primer used to confirm replacement of the yqhD promoter.

SEQ ID NOs:50-51 are oligonucleotide primers used to construct the pta-ackA disruption.

SEQ ID NOs:52-53 are oligonucleotide primers used to confirm disruption of pta-ackA.

SEQ ID NOs:54-55 are oligonucleotide primers used to construct the ptsHIcrr disruption.

SEQ ID NO:56 is an oligonucleotide primer used to confirm disruption of ptsHIcrr.

SEQ ID NOs:57-58 are oligonucleotide primers used to construct the aldA disruption.

SEQ ID NOs:59-60 are oligonucleotide primers used to confirm disruption of aldA.

SEQ ID NOs:61-62 are oligonucleotide primers used to construct the aldB disruption.

SEQ ID NOs:63-64 are oligonucleotide primers used to confirm disruption of aldB.

SEQ ID NO:65 is the nucleotide sequence for the pSYCO101 plasmid.

SEQ ID NO:66 is the nucleotide sequence for the pSYCO103 plasmid.

SEQ ID NO:67 is the nucleotide sequence for the pSYCO106 plasmid.

SEQ ID NO:68 is the nucleotide sequence for the pSYCO109 plasmid.

Applicants have made the following biological deposits under the terms of the Budapest Treaty on the International Recognition of the Deposit of Microorganisms for the Purpose of patent Procedure.

| Depositor Identification Reference | Int'l Depository Designation | Date of Deposit |
|---|---|---|
| Transformed *E. coli* DH5α containing a portion of the *Klebsiella* genome encoding the glycerol dehydratase enzyme | ATCC 69789 | 18 Apr. 1995 |
| Transformed *E. coli* DH5α containing cosmid pKP4 containing a portion of *Klebsiella* genome encoding a diol dehydratase enzyme | ATCC 69790 | 18 Apr. 1995 |
| *E. coli* MSP33.6 | ATCC 98598 | 25 Nov. 1997 |
| glpK mutant *E. coli* RJF10m | ATCC 98597 | 25 Nov. 1997 |
| *Escherichia coli*: RJ8n | ATCC PTA4216 | 9 Apr. 2002 |
| *Escherichia coli*: FMP'::Km | ATCC PTA-4732 | 28 Sep. 2002 |

The deposit(s) will be maintained in the indicated international depository for at least 30 years and will be made available to the public upon the grant of a patent disclosing it. The availability of a deposit does not constitute a license to practice the subject invention in derogation of patent rights granted by government action.

As used herein, "ATCC" refers to the American Type Culture Collection international depository located 10801 University Blvd., Manassas, Va. 20110-2209 U.S.A. The "ATCC No." is the accession number to cultures on deposit with the ATCC.

DETAILED DESCRIPTION OF THE INVENTION

The present invention provides for an improved process for bioconverting a fermentable carbon source directly to 1,3-propanediol using a single microorganism. The method is characterized by improved 1,3-propanediol yield at levels not previously obtained.

The disclosed production host strains have been engineered to maximize the metabolic efficiency of the pathway by incorporating various deletion mutations that prevent the diversion of carbon to non-productive compounds. It is contemplated that transformations and mutations can be combined so as to control particular enzyme activities for the enhancement of 1,3-propanediol production. Thus, it is within the scope of the present invention to anticipate modifications of a whole cell catalyst which lead to an increased production of 1,3-propanediol.

Terms And Definitions

The invention can be more fully understood with reference to the following terms and definitions used in the claims and specifications.

Genes that are Deleted:

The terms "NADH dehydrogenase II", "NDH II" and "Ndh" refer to the type II NADH dehydrogenase, a protein that catalyzed the conversion of ubiquinone-8+NADH+H$^+$ to ubiquinol-8+NAD$^+$. Typical of NADH dehydrogenase II is EC 1.6.99.3. NADH dehydrogenase II is encoded by ndh in *E. coli*.

The terms "aerobic respiration control protein" and "ArcA" refer to a global regulatory protein. The aerobic respiration control protein is encoded by arcA in *E. coli*.

The terms "phosphogluconate dehydratase" and "Edd" refer to a protein that catalyzed the conversion of 6-phosphogluconate to 2-keto-3-deoxy-6-phospho-gluconate+H$_2$O. Typical of phosphogluconate dehydratase is EC 4.2.1.12. Phosphogluconate dehydratase is encoded by edd in *E. coli*.

The terms "phosphocarrier protein HPr" and "PtsH" refer to the phosphocarrier protein encoded by ptsH in *E. coli*. The terms "phosphoenolpyruvate-protein phosphotransferase" and "PtsI" refer to the phosphotransferase, EC 2.7.3.9, encoded by ptsI in *E. coli*. The terms "PTS system", "glucose-specific IIA component", and "Crr" refer to EC 2.7.1.69, encoded by crr in *E. coli*. PtsH, PtsI, and Crr comprise the PTS system.

The term "phosphoenolpyruvate-sugar phosphotransferase system", "PTS system", or "PTS" refers to the phosphoenolpyruvate-dependent sugar uptake system.

The terms "methylglyoxal synthase" and "MgsA" refer to a protein that catalyzed the conversion of dihydroxy-acetone-phosphate to methyl-glyoxal+phosphate. Typical of methylglyoxal synthase is EC 4.2.3.3. Methylglyoxal synthase is encoded by mgsA in *E. coli*.

The terms "aldehyde dehydrogenase A" and "AldA" refer to a protein that catalyzed the conversion of H$_2$O+NAD$^+$+aldehyde to NADH+alcohol. Typical of aldehyde dehydrogenase A is EC 1.2.1.22. Aldehyde dehydrogenase A is encoded by aldA in *E. coli*.

The terms "aldehyde dehydrogenase B" and "AldB" refer to a protein that catalyzed the conversion of H$_2$O+NAD$^+$+aldehyde to NADH+alcohol. Typical of aldehyde dehydrogenase B is EC 1.2.1.22. Aldehyde dehydrogenase B is encoded by aldB in *E. coli*.

Genes Whose Expression has been Modified:

The terms "galactose-proton symporter" and "GalP" refer to a protein that catalyses the transport of a sugar and a proton from the periplasm to the cytoplasm. D-glucose is a preferred substrate for GalP. Galactose-proton symporter is encoded by galP in *E. coli*.

The terms "glucokinase" and "Glk" refer to a protein that catalyses the conversion of D-glucose+ATP to glucose-6-phosphate+ADP. Typical of glucokinase is EC 2.7.1.2. Glucokinase is encoded by glk in *E. coli*.

The terms "glyceraldehyde 3-phosphate dehydrogenase" and "GapA" refer to a protein that catalyses the conversion of glyceraldehyde-3-phosphate+phosphate+NAD$^+$ to 3-phospho-D-glyceroyl-phosphate+NADH+H$^+$. Typical of glyceraldehyde 3-phosphate dehydrogenase is EC 1.2.1.12. Glyceraldehyde 3-phosphate dehydrogenase is encoded by gapA in *E. coli*.

The terms "phosphoenolpyruvate carboxylase" and "Ppc" refer to a protein that catalyses the conversion of phosphoenolpyruvate+H$_2$O+CO$_2$ to phosphate+oxalacetic acid. Typical of phosphoenolpyruvate carboxylase is EC 4.1.1.31. Phosphoenolpyruvate carboxylase is encoded by ppc in *E. coli*.

The term "YciK" refers to a putative enzyme encoded by ycik which is translationally coupled to btuR, the gene encoding Cob(I)alamin adenosyltransferase in *Escherichia coli*.

The term "cob(I)alamin adenosyltransferase" refers to an enzyme responsible for the transfer of a deoxyadenosyl moiety from ATP to the reduced corrinoid. Typical of cob(I) alamin adenosyltransferase is EC 2.5.1.17. Cob(I)alamin adenosyltransferase is encoded by the gene "btuR" (GenBank M21528) in *Escherichia coli*, "cobA" (GenBank L08890) in *Salmonella typhimurium*, and "cobO" (GenBank M62866) in *Pseudomonas denitrificans*.

Additional Definitions:

The term "short 1.20 GI promoter" refers to SEQ ID NO:31. The term "short 1.5 GI promoter" refers to SEQ ID NO:28. The terms "short 1.6 GI promoter" and "short wild-type promoter" are used interchangeably and refer to SEQ ID NO:32.

The terms "glycerol-3-phosphate dehydrogenase" and "G3PDH" refer to a polypeptide responsible for an enzyme activity that catalyzes the conversion of dihydroxyacetone phosphate (DHAP) to glycerol-3-phosphate (G3P). In vivo G3PDH may be NADH; NADPH; or FAD-dependent. When specifically referring to a cofactor specific glycerol-3-phosphate dehydrogenase, the terms "NADH-dependent glycerol-3-phosphate dehydrogenase", "NADPH-dependent glycerol-3-phosphate dehydrogenase" and "FAD-dependent glycerol-3-phosphate dehydrogenase" will be used. As it is generally the case that NADH-dependent and NADPH-dependent glycerol-3-phosphate dehydrogenases are able to use NADH and NADPH interchangeably (for example by the gene encoded by gpsA), the terms NADH-dependent and NADPH-dependent glycerol-3-phosphate dehydrogenase will be used interchangeably. The NADH-dependent enzyme (EC 1.1.1.8) is encoded, for example, by several genes including GPD1 (GenBank Z74071×2), or GPD2 (GenBank Z35169×1), or GPD3 (GenBank G984182), or DAR1 (GenBank Z74071× 2). The NADPH-dependent enzyme (EC 1.1.1.94) is encoded by gpsA (GenBank U321643, (cds 197911-196892) G466746 and L45246). The FAD-dependent enzyme (EC 1.1.99.5) is encoded by GUT2 (GenBank Z47047×23), or glpD (GenBank G147838), or glpABC (GenBank M20938) (see WO 9928480 and references therein, which are herein incorporated by reference).

The terms "glycerol-3-phosphatase", "sn-glycerol-3-phosphatase", or "d,l-glycerol phosphatase", and "G3P phosphatase" refer to a polypeptide responsible for an enzyme activity that catalyzes the conversion of glycerol-3-phosphate and water to glycerol and inorganic phosphate. G3P phosphatase is encoded, for example, by GPP1 (GenBank Z47047×125), or GPP2 (GenBank U18813×11) (see WO 9928480 and references therein, which are herein incorporated by reference).

The term "glycerol kinase" refers to a polypeptide responsible for an enzyme activity that catalyzes the conversion of glycerol and ATP to glycerol-3-phosphate and ADP. The high-energy phosphate donor ATP may be replaced by physiological substitutes (e.g., phosphoenolpyruvate). Glycerol kinase is encoded, for example, by GUT1 (GenBank U11583×19) and glpk (GenBank L19201) (see WO 9928480 and references therein, which are herein incorporated by reference).

The term "glycerol dehydrogenase" refers to a polypeptide responsible for an enzyme activity that catalyzes the conversion of glycerol to dihydroxyacetone (E.C. 1.1.1.6) or glycerol to glyceraldehyde (E.C. 1.1.1.72). A polypeptide responsible for an enzyme activity that catalyzes the conversion of glycerol to dihydroxyacetone is also referred to as a "dihydroxyacetone reductase". Glycerol dehydrogenase may be dependent upon NADH (E.C. 1.1.1.6), NADPH (E.C. 1.1.1.72), or other cofactors (e.g., E.C. 1.1.99.22). A NADH-dependent glycerol dehydrogenase is encoded, for example, by gldA (GenBank U00006) (see WO 9928480 and references therein, which are herein incorporated by reference).

The term "dehydratase enzyme" or "dehydratase" will refer to any enzyme activity that catalyzes the conversion of a glycerol molecule to the product 3-hydroxypropionaldehyde. For the purposes of the present invention the dehydratase enzymes include a glycerol dehydratase (E.C. 4.2.1.30) and a diol dehydratase (E.C. 4.2.1.28) having preferred substrates of glycerol and 1,2-propanediol, respectively. Genes for dehydratase enzymes have been identified in *Klebsiella pneumoniae*, *Citrobacter freundii*, *Clostridium pasteurianum*, *Salmonella typhimurium*, and *Klebsiella oxytoca*. In each case, the dehydratase is composed of three subunits: the large or "α" subunit, the medium or "β" subunit, and the small or "γ" subunit. Due to the wide variation in gene nomenclature used in the literature, a comparative chart is given in Table 1 to facilitate identification. The genes are also described in, for example, Daniel et al. (*FEMS Microbiol. Rev.* 22, 553 (1999)) and Toraya and Mori (*J. Biol. Chem.* 274, 3372 (1999)). Referring to Table 1, genes encoding the large or "α" subunit of glycerol dehydratase include dhaB1, gldA and dhaB; genes encoding the medium or "β" subunit include dhaB2, gldB, and dhac; genes encoding the small or "γ" subunit include dhaB3, gldC, and dhaE. Also referring to Table 1, genes encoding the large or "α" subunit of diol dehydratase include pduC and pddA; genes encoding the medium or "β" subunit include pduD and pddB; genes encoding the small or "γ" subunit include pduE and pddC.

TABLE 1

Comparative chart of gene names and GenBank references for dehydratase and dehydratase linked functions.

| | GENE FUNCTION: | | | | | | | | |
|---|---|---|---|---|---|---|---|---|---|
| | regulatory | | unknown | | reactivation | | 1,3-PD dehydrogenase | | unknown |
| ORGANISM (GenBank Reference) | gene | base pairs | gene | base pairs | Geme | base pairs | gene | base pairs | gene | base pairs |
| *K. pneumoniae* (SEQ ID NO: 1) | dhaR | 2209-4134 | orfW | 4112-4642 | OrfX | 4643-4996 | dhaT | 5017-6108 | orfY | 6202-6630 |
| *K. pneumoniae* (U30903) | | | orf2c | 7116-7646 | orf2b | 6762-7115 | dhaT | 5578-6741 | orf2a | 5125-5556 |

TABLE 1-continued

Comparative chart of gene names and GenBank references
for dehydratase and dehydratase linked functions.

| | | | | | | GdrB | | | | | |
|---|---|---|---|---|---|---|---|---|---|---|---|
| K. pneumoniae (U60992) | | | | | | | | | | | |
| C. freundii (U09771) | dhaR | 3746-5671 | orfW | 5649-6179 | OrfX | 6180-6533 | dhaT | 6550-7713 | orfY | 7736-8164 |
| C. pasteurianum (AF051373) | | | | | | | | | | | |
| C. pasteurianum (AF006034) | | | orfW | 210-731 | OrfX | 1-196 | dhaT | 1232-2389 | orfY | 746-1177 |
| S. typhimurium (AF026270) | | | | | PduH | 8274-8645 | | | | |
| K. oxytoca (AF017781) | | | | | DdrB | 2063-2440 | | | | |
| K. oxytoca (AF051373) | | | | | | | | | | |

| | GENE FUNCTION: | | | | | | | |
|---|---|---|---|---|---|---|---|---|
| | dehydratase, α | | dehydratase, β | | dehydratase, γ | | reactivation | |
| ORGANISM (GenBank Reference) | gene | base pairs | gene | base pairs | Gene | base pairs | gene | base pairs |
| K. pneumoniae (SEQ ID NO: 1) | dhaB1 | 7044-8711 | dhaB2 | 8724-9308 | dhaB3 | 9311-9736 | orfZ | 9749-11572 |
| K. pneumoniae (U30903) | dhaB1 | 3047-4714 | dhaB2 | 2450-2890 | dhaB3 | 2022-2447 | dhaB4 | 186-2009 |
| K. pneumoniae (U60992) | gldA | 121-1788 | gldB | 1801-2385 | GldC | 2388-2813 | gdrA | |
| C. freundii (U09771) | dhaB | 8556-10223 | dhaC | 10235-10819 | DhaE | 10822-11250 | orfZ | 11261-13072 |
| C. pasteurianum (AF051373) | dhaB | 84-1748 | dhaC | 1779-2318 | DhaE | 2333-2773 | orfZ | 2790-4598 |
| C. pasteurianum (AF006034) | | | | | | | | |
| S. typhimurium (AF026270) | pduC | 3557-5221 | pduD | 5232-5906 | PduE | 5921-6442 | pduG | 6452-8284 |
| K. oxytoca (AF017781) | | | | | | | ddrA | 241-2073 |
| K. oxytoca (AF051373) | pddA | 121-1785 | pddB | 1796-2470 | PddC | 2485-3006 | | |

Glycerol and diol dehydratases are subject to mechanism-based suicide inactivation by glycerol and some other substrates (Daniel et al., *FEMS Microbiol. Rev.* 22, 553 (1999)). The term "dehydratase reactivation factor" refers to those proteins responsible for reactivating the dehydratase activity. The terms "dehydratase reactivating activity", "reactivating the dehydratase activity" or "regenerating the dehydratase activity" refers to the phenomenon of converting a dehydratase not capable of catalysis of a substrate to one capable of catalysis of a substrate or to the phenomenon of inhibiting the inactivation of a dehydratase or the phenomenon of extending the useful half-life of the dehydratase enzyme in vivo. Two proteins have been identified as being involved as the dehydratase reactivation factor (see WO 9821341 (US 6013494) and references therein, which are herein incorporated by reference; Daniel et al., supra; Toraya and Mori, *J. Biol. Chem.* 274, 3372 (1999); and Tobimatsu et al., *J. Bacteriol.* 181, 4110 (1999)). Referring to Table 1, genes encoding one of the proteins include orfZ, dhaB4, gdrA, pduG and ddrA. Also referring to Table 1, genes encoding the second of the two proteins include orfX, orf2b, gdrB, pduH and ddrB.

The terms "1,3-propanediol oxidoreductase", "1,3-propanediol dehydrogenase" or "DhaT" refer to the polypeptide(s) responsible for an enzyme activity that is capable of catalyzing the interconversion of 3-HPA and 1,3-propanediol provided the gene(s) encoding such activity is found to be physically or transcriptionally linked to a dehydratase enzyme in its natural (i.e., wild type) setting; for example, the gene is found within a dha regulon as is the case with dhaT from *Klebsiella pneumoniae*. Referring to Table 1, genes encoding a 1,3-propanediol oxidoreductase include dhaT from *Klebsiella pneumoniae*, *Citrobacter freundii*, and *Clostridium pasteurianum*. Each of these genes encode a polypeptide belonging to the family of type III alcohol dehydrogenases, exhibits a conserved iron-binding motif, and has a preference for the $NAD^+$/NADH linked interconversion of 3-HPA and 1,3-propanediol (Johnson and Lin, *J. Bacteriol.* 169, 2050 (1987); Daniel et al., *J. Bacteriol.* 177, 2151 (1995); and Leurs et al., *FEMS Microbiol. Lett.* 154, 337 (1997)). Enzymes with similar physical properties have been isolated from *Lactobacillus brevis* and *Lactobacillus buchneri* (Veiga da Dunha and Foster, *Appl. Environ. Microbiol.* 58, 2005 (1992)).

The term "dha regulon" refers to a set of associated genes or open reading frames encoding various biological activities, including but not limited to a dehydratase activity, a reactivation activity, and a 1,3-propanediol oxidoreductase. Typically a dha regulon comprises the open reading frames dhaR, orfY, dhaT, orfX, orfW, dhaB1, dhaB2, dhaB3, and orfZ as described herein.

The term "non-specific catalytic activity" refers to the polypeptide(s) responsible for an enzyme activity that is sufficient to catalyze the interconversion of 3-HPA and 1,3-propanediol and specifically excludes 1,3-propanediol oxidoreductase(s). Typically these enzymes are alcohol dehydrogenases. Such enzymes may utilize cofactors other than $NAD^+$/NADH, including but not limited to flavins such as FAD or FMN. A gene for a non-specific alcohol dehydrogenase (yqhD) is found, for example, to be endogenously encoded and functionally expressed within *E. coli* $K_{12}$ strains.

The terms "function" or "enzyme function" refer to the catalytic activity of an enzyme in altering the energy required to perform a specific chemical reaction. It is understood that such an activity may apply to a reaction in equilibrium where the production of either product or substrate may be accomplished under suitable conditions.

The terms "polypeptide" and "protein" are used interchangeably.

The terms "carbon substrate" and "carbon source" refer to a carbon source capable of being metabolized by host microorganisms of the present invention and particularly carbon sources selected from the group consisting of monosaccharides, oligosaccharides, polysaccharides, and one-carbon substrates or mixtures thereof.

The terms "host cell" or "host microorganism" refer to a microorganism capable of receiving foreign or heterologous genes and of expressing those genes to produce an active gene product.

The terms "foreign gene", "foreign DNA", "heterologous gene" and "heterologous DNA" refer to genetic material native to one organism that has been placed within a host microorganism by various means. The gene of interest may be a naturally occurring gene, a mutated gene, or a synthetic gene.

The terms "transformation" and "transfection" refer to the acquisition of new genes in a cell after the incorporation of nucleic acid. The acquired genes may be integrated into chromosomal DNA or introduced as extrachromosomal replicating sequences. The term "transformant" refers to the product of a transformation.

The term "genetically altered" refers to the process of changing hereditary material by transformation or mutation.

The terms "recombinant microorganism" and "transformed host" refer to any microorganism having been transformed with heterologous or foreign genes or extra copies of homologous genes. The recombinant microorganisms of the present invention express foreign genes encoding glycerol-3-phosphate dehydrogenase (GPD1), glycerol-3-phosphatase (GPP2), glycerol dehydratase (dhaB1, dhaB2 and dhaB3), dehydratase reactivation factor (orfZ and orfX), and optionally 1,3-propanediol oxidoreductase (dhaT) for the production of 1,3-propanediol from suitable carbon substrates. A preferred embodiment is an E. coli transformed with these genes but lacking a functional dhaT. A host microorganism, other than E. coli, may also be transformed to contain the disclosed genes and the gene for the non-specific catalytic activity for the interconversion of 3-HPA and 1,3-propanediol, specifically excluding 1,3-propanediol oxidoreductase(s) (dhaT).

"Gene" refers to a nucleic acid fragment that expresses a specific protein, including regulatory sequences preceding (5' non-coding) and following (3' non-coding) the coding region. The terms "native" and "wild-type" refer to a gene as found in nature with its own regulatory sequences.

The terms "encoding" and "coding" refer to the process by which a gene, through the mechanisms of transcription and translation, produces an amino acid sequence. It is understood that the process of encoding a specific amino acid sequence includes DNA sequences that may involve base changes that do not cause a change in the encoded amino acid, or which involve base changes which may alter one or more amino acids, but do not affect the functional properties of the protein encoded by the DNA sequence. It is therefore understood that the invention encompasses more than the specific exemplary sequences.

The term "isolated" refers to a protein or DNA sequence that is removed from at least one component with which it is naturally associated.

An "isolated nucleic acid molecule" is a polymer of RNA or DNA that is single- or double-stranded, optionally containing synthetic, non-natural or altered nucleotide bases. An isolated nucleic acid molecule in the form of a polymer of DNA may be comprised of one or more segments of cDNA, genomic DNA or synthetic DNA.

"Substantially similar" refers to nucleic acid molecules wherein changes in one or more nucleotide bases result in substitution of one or more amino acids, but do not affect the functional properties of the protein encoded by the DNA sequence. "Substantially similar" also refers to nucleic acid molecules wherein changes in one or more nucleotide bases do not affect the ability of the nucleic acid molecule to mediate alteration of gene expression by antisense or co-suppression technology. "Substantially similar" also refers to modifications of the nucleic acid molecules of the instant invention (such as deletion or insertion of one or more nucleotide bases) that do not substantially affect the functional properties of the resulting transcript vis-à-vis the ability to mediate alteration of gene expression by antisense or co-suppression technology or alteration of the functional properties of the resulting protein molecule. The invention encompasses more than the specific exemplary sequences.

For example, it is well known in the art that alterations in a gene which result in the production of a chemically equivalent amino acid at a given site, but do not effect the functional properties of the encoded protein are common. For the purposes of the present invention substitutions are defined as exchanges within one of the following five groups:

1. Small aliphatic, nonpolar or slightly polar residues: Ala, Ser, Thr (Pro, Gly);
2. Polar, negatively charged residues and their amides: Asp, Asn, Glu, Gln;
3. Polar, positively charged residues: His, Arg, Lys;
4. Large aliphatic, nonpolar residues: Met, Leu, Ile, Val (Cys); and
5. Large aromatic residues: Phe, Tyr, Trp.

Thus, a codon for the amino acid alanine, a hydrophobic amino acid, may be substituted by a codon encoding another less hydrophobic residue (such as glycine) or a more hydrophobic residue (such as valine, leucine, or isoleucine). Similarly, changes which result in substitution of one negatively charged residue for another (such as aspartic acid for glutamic acid) or one positively charged residue for another (such as lysine for arginine) can also be expected to produce a functionally equivalent product.

In many cases, nucleotide changes which result in alteration of the N-terminal and C-terminal portions of the protein molecule would also not be expected to alter the activity of the protein.

Each of the proposed modifications is well within the routine skill in the art, as is determination of retention of biological activity of the encoded products. Moreover, the skilled artisan recognizes that substantially similar sequences encompassed by this invention are also defined by their ability to hybridize, under stringent conditions (0.1×SSC, 0.1% SDS, 65° C. and washed with 2×SSC, 0.1% SDS followed by 0.1×SSC, 0.1% SDS), with the sequences exemplified herein. Preferred substantially similar nucleic acid fragments of the instant invention are those nucleic acid fragments whose DNA sequences are at least 80% identical to the DNA sequence of the nucleic acid fragments reported herein. More preferred nucleic acid fragments are at least 90% identical to the DNA sequence of the nucleic acid fragments reported herein. Most preferred are nucleic acid fragments that are at least 95% identical to the DNA sequence of the nucleic acid fragments reported herein.

A nucleic acid fragment is "hybridizable" to another nucleic acid fragment, such as a cDNA, genomic DNA, or RNA, when a single stranded form of the nucleic acid fragment can anneal to the other nucleic acid fragment under the appropriate conditions of temperature and solution ionic strength. Hybridization and washing conditions are well known and exemplified in Sambrook, J., Fritsch, E. F. and Maniatis, T. *Molecular Cloning: A Laboratory Manual*, Second Edition, Cold Spring Harbor Laboratory Press, Cold Spring Harbor (1989), particularly Chapter 11 and Table 11.1 therein (entirely incorporated herein by reference). The conditions of temperature and ionic strength determine the "stringency" of the hybridization. For preliminary screening for homologous nucleic acids, low stringency hybridization conditions, corresponding to a Tm of 55°, can be used, e.g., 5×SSC, 0.1% SDS, 0.25% milk, and no formamide; or 30% formamide, 5×SSC, 0.5% SDS. Moderate stringency hybridization conditions correspond to a higher Tm, e.g., 40% formamide, with 5× or 6×SSC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridization decreases in the following order: RNA:RNA, DNA:RNA, DNA:DNA. For hybrids of greater than 100 nucleotides in length, equations for calculating Tm have been derived (see Sambrook et al., supra, 9.50-9.51). For hybridization with shorter nucleic acids, i.e., oligonucleotides, the position of mismatches becomes more important, and the length of the oligonucleotide determines its specificity (see Sambrook et al., supra, 11.7-11.8). In one embodiment the length for a hybridizable nucleic acid is at least about 10 nucleotides. Preferable a minimum length for a hybridizable nucleic acid is at least about 15 nucleotides; more preferably at least about 20 nucleotides; and most preferably the length is at least 30 nucleotides. Furthermore, the skilled artisan will recognize that the temperature and wash solution salt concentration may be adjusted as necessary according to factors such as length of the probe.

A "substantial portion" refers to an amino acid or nucleotide sequence which comprises enough of the amino acid sequence of a polypeptide or the nucleotide sequence of a gene to afford putative identification of that polypeptide or gene, either by manual evaluation of the sequence by one skilled in the art, or by computer-automated sequence comparison and identification using algorithms such as BLAST (Basic Local Alignment Search Tool; Altschul et al., *J. Mol. Biol.* 215:403-410 (1993); see also www.ncbi.nlm.nih.gov/BLAST/). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene-specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid molecule comprising the primers. Accordingly, a "substantial portion" of a nucleotide sequence comprises enough of the sequence to afford specific identification and/or isolation of a nucleic acid molecule comprising the sequence. The instant specification teaches partial or complete amino acid and nucleotide sequences encoding one or more particular proteins. The skilled artisan, having the benefit of the sequences as reported herein, may now use all or a substantial portion of the disclosed sequences for the purpose known to those skilled in the art. Accordingly, the instant invention comprises the complete sequences as reported in the accompanying Sequence Listing, as well as substantial portions of those sequences as defined above.

The term "complementary" describes the relationship between nucleotide bases that are capable to hybridizing to one another. For example, with respect to DNA, adenosine is complementary to thymine and cytosine is complementary to guanine. Accordingly, the instant invention also includes isolated nucleic acid molecules that are complementary to the complete sequences as reported in the accompanying Sequence Listing as well as those substantially similar nucleic acid sequences.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: *Computational Molecular Biology*; Lesk, A. M., Ed.; Oxford University Press: New York, 1988; *Biocomputing: Informatics and Genome Projects*; Smith, D. W., Ed.; Academic Press: New York, 1993; *Computer Analysis of Sequence Data, Part I*; Griffin, A. M. and Griffin, H. G., Eds.; Humana Press: New Jersey, 1994; *Sequence Analysis in Molecular Biology*; von Heinje, G., Ed.; Academic Press: New York, 1987; and *Sequence Analysis Primer*; Gribskov, M. and Devereux, J., Eds.; Stockton Press: New York, 1991. Preferred methods to determine identity are designed to give the largest match between the sequences tested.

Methods to determine identity and similarity are codified in publicly available computer programs. Preferred computer program methods to determine identity and similarity between two sequences include, but are not limited to, the GCG Pileup program found in the GCG program package, using the Needleman and Wunsch algorithm with their standard default values of gap creation penalty=12 and gap extension penalty=4 (Devereux et al., *Nucleic Acids Res.* 12:387-395 (1984)), BLASTP, BLASTN, and FASTA (Pearson et al., *Proc. Natl. Acad. Sci. USA* 85:2444-2448 (1988). The BLASTX program is publicly available from NCBI and other sources (*BLAST Manual*, Altschul et al., Natl. Cent. Biotechnol. Inf., Natl. Library Med. (NCBI NLM) NIH, Bethesda, Md. 20894; Altschul et al., *J. Mol. Biol.* 215:403-410 (1990); Altschul et al., "Gapped BLAST and PSI-BLAST: a new generation of protein database search programs", *Nucleic Acids Res.* 25:3389-3402 (1997)). Another preferred method to determine percent identity, is by the method of DNASTAR protein alignment protocol using the Jotun-Hein algorithm (Hein et al., *Methods Enzymol.* 183:626-645 (1990)). Default parameters for the Jotun-Hein method for alignments are: for multiple alignments, gap penalty=11, gap length penalty=3; for pairwise alignments ktuple=6. As an illustration, by a polynucleotide having a nucleotide sequence having at least, for example, 95% "identity" to a reference nucleotide sequence it is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having an amino acid sequence having at least, for example, 95% identity to a reference amino acid sequence is intended that the amino acid sequence of the polypeptide is identical to the reference sequence except that the polypeptide sequence may include up to five amino acid alterations per each 100 amino acids of the reference amino acid. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

The term "homologous" refers to a protein or polypeptide native or naturally occurring in a given host cell. The invention includes microorganisms producing homologous proteins via recombinant DNA technology.

The term "percent homology" refers to the extent of amino acid sequence identity between polypeptides. When a first amino acid sequence is identical to a second amino acid sequence, then the first and second amino acid sequences exhibit 100% homology. The homology between any two polypeptides is a direct function of the total number of matching amino acids at a given position in either sequence, e.g., if half of the total number of amino acids in either of the two sequences are the same then the two sequences are said to exhibit 50% homology.

"Codon degeneracy" refers to divergence in the genetic code permitting variation of the nucleotide sequence without effecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

Modifications to the sequence, such as deletions, insertions, or substitutions in the sequence which produce silent changes that do not substantially affect the functional properties of the resulting protein molecule are also contemplated. For example, alteration in the gene sequence which reflect the degeneracy of the genetic code, or which result in the production of a chemically equivalent amino acid at a given site, are contemplated. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a biologically equivalent product. Nucleotide changes which result in alteration of the N-terminal and C-terminal portions of the protein molecule would also not be expected to alter the activity of the protein. In some cases, it may in fact be desirable to make mutants of the sequence in order to study the effect of alteration on the biological activity of the protein. Each of the proposed modifications is well within the routine skill in the art, as is determination of retention of biological activity in the encoded products. Moreover, the skilled artisan recognizes that sequences encompassed by this invention are also defined by their ability to hybridize, under stringent conditions (0.1×SSC, 0.1% SDS, 65° C.), with the sequences exemplified herein.

The term "expression" refers to the transcription and translation to gene product from a gene coding for the sequence of the gene product.

The terms "plasmid", "vector", and "cassette" refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitates transformation of a particular host cell. "Expression cassette" refers to a specific vector containing a foreign gene and having elements in addition to the foreign gene that allow for enhanced expression of that gene in a foreign host.

Construction of Recombinant Organisms

Recombinant organisms containing the necessary genes that will encode the enzymatic pathway for the conversion of a carbon substrate to 1,3-propanediol may be constructed using techniques well known in the art. Genes encoding glycerol-3-phosphate dehydrogenase (GPD1), glycerol-3-phosphatase (GPP2), glycerol dehydratase (dhaB1, dhaB2, and dhaB3), dehydratase reactivation factor (orfZ and orfX) and 1,3-propanediol oxidoreductase (dhaT) were isolated from a native host such as *Klebsiella* or *Saccharomyces* and used to transform host strains such as *E. coli* DH5α, ECL707, AA200, or KLP23.

Isolation of Genes

Methods of obtaining desired genes from a bacterial genome are common and well known in the art of molecular biology. For example, if the sequence of the gene is known, suitable genomic libraries may be created by restriction endonuclease digestion and may be screened with probes complementary to the desired gene sequence. Once the sequence is isolated, the DNA may be amplified using standard primer directed amplification methods such as polymerase chain reaction (PCR) (U.S. Pat. No. 4,683,202) to obtain amounts of DNA suitable for transformation using appropriate vectors.

Alternatively, cosmid libraries may be created where large segments of genomic DNA (35-45 kb) may be packaged into vectors and used to transform appropriate hosts. Cosmid vectors are unique in being able to accommodate large quantities of DNA. Generally cosmid vectors have at least one copy of the cos DNA sequence which is needed for packaging and subsequent circularization of the foreign DNA. In addition to the cos sequence these vectors will also contain an origin of replication such as ColE1 and drug resistance markers such as a gene resistant to ampicillin or neomycin. Methods of using cosmid vectors for the transformation of suitable bacterial hosts are well described in Sambrook, J. et al., supra.

Typically to clone cosmids, foreign DNA is isolated using the appropriate restriction endonucleases and ligated, adjacent to the cos region of the cosmid vector using the appropriate ligases. Cosmid vectors containing the linearized foreign DNA are then reacted with a DNA packaging vehicle such as bacteriophage. During the packaging process the cos sites are cleaved and the foreign DNA is packaged into the head portion of the bacterial viral particle. These particles are then used to transfect suitable host cells such as *E. coli*. Once injected into the cell, the foreign DNA circularizes under the influence of the cos sticky ends. In this manner large segments of foreign DNA can be introduced and expressed in recombinant host cells.

Isolation And Cloning of Genes Encoding Glycerol Dehydratase (dhaB1, dhaB2, and dhaB3), Dehydratase Reactivating Factors (orfZ and orfX), and 1,3-propanediol dehydrogenase (dhaT)

Cosmid vectors and cosmid transformation methods were used within the context of the present invention to clone large segments of genomic DNA from bacterial genera known to possess genes capable of processing glycerol to 1,3-propanediol. Specifically, genomic DNA from *K. pneumoniae* was isolated by methods well known in the art and digested with the restriction enzyme Sau3A for insertion into a cosmid vector Supercos 1 and packaged using GigapackII packaging extracts. Following construction of the vector *E. coli* XL1-Blue MR cells were transformed with the cosmid DNA. Transformants were screened for the ability to convert glycerol to 1,3-propanediol by growing the cells in the presence of glycerol and analyzing the media for 1,3-propanediol formation.

Two of the 1,3-propanediol positive transformants were analyzed and the cosmids were named pKP1 and pKP2. DNA sequencing revealed extensive homology to the glycerol dehydratase gene from *C. freundii*, demonstrating that these transformants contained DNA encoding the glycerol dehydratase gene. Other 1,3-propanediol positive transformants were analyzed and the cosmids were named pKP4 and pKP5. DNA sequencing revealed that these cosmids carried DNA encoding a diol dehydratase gene.

Although the instant invention utilizes the isolated genes from within a *Klebsiella* cosmid, alternate sources of dehydratase genes and dehydratase reactivation factor genes include, but are not limited to, *Citrobacter*, *Clostridia* and *Salmonella* (see Table 1).

Genes Encoding G3PDH and G3P Phosphatase

The present invention provides genes suitable for the expression of G3PDH and G3P phosphatase activities in a host cell.

Genes encoding G3PDH are known. For example, GPD1 has been isolated from *Saccharomyces* (Wang et al., supra). Similarly, G3PDH activity has also been isolated from *Saccharomyces* encoded by GPD2 (Eriksson et al., *Mol. Microbiol.* 17, 95 (1995)).

For the purposes of the present invention it is contemplated that any gene encoding a polypeptide responsible for NADH-dependent G3PDH activity is suitable wherein that activity is capable of catalyzing the conversion of dihydroxyacetone phosphate (DHAP) to glycerol-3-phosphate (G3P). Further, it is contemplated that any gene encoding the amino acid sequence of NADH-dependent G3PDH's corresponding to the genes DAR1, GPD1, GPD2, GPD3, and gpsA will be functional in the present invention wherein that amino acid sequence may encompass amino acid substitutions, deletions or additions that do not alter the function of the enzyme. The skilled person will appreciate that genes encoding G3PDH isolated from other sources will also be suitable for use in the present invention. Genes encoding G3P phosphatase are known. For example, GPP2 has been isolated from *Saccharomyces cerevisiae* (Norbeck et al., *J. Biol. Chem.* 271, 13875 (1996)).

For the purposes of the present invention, any gene encoding a G3P phosphatase activity is suitable for use in the method wherein that activity is capable of catalyzing the conversion of glycerol-3-phosphate plus $H_2O$ to glycerol plus inorganic phosphate. Further, any gene encoding the amino acid sequence of G3P phosphatase corresponding to the genes GPP2 and GPP1 will be functional in the present invention including any amino acid sequence that encompasses amino acid substitutions, deletions or additions that do not alter the function of the G3P phosphatase enzyme. The skilled person will appreciate that genes encoding G3P phosphatase isolated from other sources will also be suitable for use in the present invention.

Host Cells

Suitable host cells for the recombinant production of 1,3-propanediol may be either prokaryotic or eukaryotic and will be limited only by the host cell ability to express the active enzymes for the 1,3-propanediol pathway. Suitable host cells will be microorganisms such as *Citrobacter, Enterobacter, Clostridium, Klebsiella, Aerobacter, Lactobacillus, Aspergillus, Saccharomyces, Schizosaccharomyces, Zygosaccharomyces, Pichia, Kluyveromyces, Candida, Hansenula, Debaryomyces, Mucor, Torulopsis, Methylobacter, Escherichia, Salmonella, Bacillus, Streptomyces*, and *Pseudomonas*. Preferred in the present invention are *Escherichia coli, Escherichia blattae, Klebsiella, Citrobacter*, and *Aerobacter*. Most preferred is *E. coli* (KLP23 (WO 2001012833 A2), RJ8.n (ATCC PTA-4216), *E. coli*: FMP'::Km (ATCC PTA4732), MG 1655 (ATCC 700926)).

Vectors and Expression Cassettes

The present invention provides a variety of vectors and transformation and expression cassettes suitable for the cloning, transformation and expression of G3PDH, G3P phosphatase, dehydratase, and dehydratase reactivation factor into a suitable host cell. Suitable vectors will be those which are compatible with the microorganism employed. Suitable vectors can be derived, for example, from a bacterium, a virus (such as bacteriophage T7 or a M-13 derived phage), a cosmid, a yeast or a plant. Protocols for obtaining and using such vectors are known to those in the art (Sambrook et al., supra).

Initiation control regions, or promoters, which are useful to drive expression of the G3PDH and G3P phosphatase genes (DAR1 and GPP2, respectively) in the desired host cell are numerous and familiar to those skilled in the art. Virtually any promoter capable of driving these genes is suitable for the present invention including but not limited to CYC1, HIS3, GAL1, GAL10, ADH1, PGK, PHO5, GAPDH, ADC1, TRP1, URA3, LEU2, ENO, and TPI (useful for expression in *Saccharomyces*); AOX1 (useful for expression in *Pichia*); and lac, trp, $\lambda P_L$, $\lambda P_R$, T7, tac, and trc (useful for expression in *E. coli*).

Termination control regions may also be derived from various genes native to the preferred hosts. Optionally, a termination site may be unnecessary; however, it is most preferred if included.

For effective expression of the instant enzymes, DNA encoding the enzymes are linked operably through initiation codons to selected expression control regions such that expression results in the formation of the appropriate messenger RNA.

Particularly useful in the present invention are the vectors pSYCO101, pSYCO103, pSYCO106, and pSYCO109. The essential elements are derived from the dha regulon isolated from *Klebsiella pneumoniae* and from *Saccharomyces cerevisiae*. Each contains the open reading frames dhaB1, dhaB2, dhaB3, dhaX, orfX, DAR1, and GPP2 arranged in three separate operons, nucleotide sequences of which are given in SEQ ID NO:65, SEQ ID NO:66, SEQ ID NO:67, and SEQ ID NO:68, respectively. The differences between the vectors are illustrated in the chart below [the prefix "p-" indicates a promoter; the open reading frames contained within each "( )" represent the composition of an operon]:

pSYCO101 (SEQ ID NO:65):
 p-trc (Dar1_GPP2) in opposite orientation compared to the other 2 pathway operons,
 p-1.6 long GI (dhaB1_dhaB2_dhaB3_dhaX), and
 p-1.6 long GI (orfY_orX_orfW).
pSYCO103 (SEQ ID NO:66):
 p-trc (Dar1_GPP2) same orientation compared to the other 2 pathway operons,
 p-1.5 long GI (dhaB1_dhaB2_dhaB3_dhaX), and
 p-1.5 long GI (orfY_orfX_orfW).
pSYCO106 (SEQ ID NO:67):
 p-trc (Dar1_GPP2) same orientation compared to the other 2 pathway operons,
 p-1.6 long GI (dhaB1_dhaB2_dhaB3_dhaX), and
 p-1.6 long GI (orfY_orfX_orfW).
pSYCO109 (SEQ ID NO:68):
 p-trc (Dar1_GPP2) same orientation compared to the other 2 pathway operons,
 p-1.6 long GI (dhaB1_dhaB2_dhaB3_dhaX), and
 p-1.6 long GI (orfY_orfX).

Transformation of Suitable Hosts and Expression of Genes for the Production of 1,3-propanediol Once suitable cassettes are constructed they are used to transform appropriate host cells. Introduction of the cassette containing the genes encoding G3PDH, G3P phosphatase, dehydratase, and dehydratase reactivation factor into the host cell may be accomplished by known procedures such as by transformation (e.g., using calcium-permeabilized cells, electroporation), or by transfection using a recombinant phage virus (Sambrook et al., supra).

In the present invention cassettes were used to transform the *E. coli* as fully described in the GENERAL METHODS and EXAMPLES.

Mutants

In addition to the cells exemplified, it is contemplated that the present method will be able to make use of cells having single or multiple mutations specifically designed to enhance the production of 1,3-propanediol. Cells that normally divert a carbon feed stock into non-productive pathways, or that exhibit significant catabolite repression could be mutated to avoid these phenotypic deficiencies. For example, many wild-type cells are subject to catabolite repression from glucose and by-products in the media and it is contemplated that mutant strains of these wild-type organisms, capable of 1,3-propanediol production that are resistant to glucose repression, would be particularly useful in the present invention.

Methods of creating mutants are common and well known in the art. For example, wild-type cells may be exposed to a variety of agents such as radiation or chemical mutagens and then screened for the desired phenotype. When creating mutations through radiation either ultraviolet (UV) or ionizing radiation may be used. Suitable short wave UV wavelengths for genetic mutations will fall within the range of 200 nm to 300 nm where 254 nm is preferred. UV radiation in this wavelength principally causes changes within nucleic acid sequence from guanidine and cytosine to adenine and thymidine. Since all cells have DNA repair mechanisms that would repair most UV induced mutations, agents such as caffeine and other inhibitors may be added to interrupt the repair process and maximize the number of effective mutations. Long wave UV mutations using light in the 300 nm to 400 nm range are also possible but are generally not as effective as the short wave UV light unless used in conjunction with various activators such as psoralen dyes that interact with the DNA.

Mutagenesis with chemical agents is also effective for generating mutants and commonly used substances include chemicals that affect nonreplicating DNA such as $HNO_2$ and $NH_2OH$, as well as agents that affect replicating DNA such as acridine dyes, notable for causing frameshift mutations. Specific methods for creating mutants using radiation or chemical agents are well documented in the art. See, for example, Thomas D. Brock in Biotechnology: *A Textbook of Industrial Microbiology*, Second Edition (1989) Sinauer Associates, Inc., Sunderland, MA., or Deshpande, Mukund V., *Appl. Biochem. Biotechnol.* 36, 227 (1992), herein incorporated by reference.

After mutagenesis has occurred, mutants having the desired phenotype may be selected by a variety of methods. Random screening is most common where the mutagenized cells are selected for the ability to produce the desired product or intermediate. Alternatively, selective isolation of mutants can be performed by growing a mutagenized population on selective media where only resistant colonies can develop. Methods of mutant selection are highly developed and well known in the art of industrial microbiology. See for example Brock, Supra; DeMancilha et al., *Food Chem*. 14, 313 (1984).

In addition to the methods for creating mutants described above, selected genes involved in converting carbon substrate to 1,3-propanediol may be up-regulated or down-regulated by a variety of methods which are known to those skilled in the art. It is well understood that up-regulation or down-regulation of a gene refers to an alteration in the activity of the protein encoded by that gene relative to a control level of activity, for example, by the activity of the protein encoded by the corresponding (or non-altered) wild-type gene.

Up-Regulation:

Specific genes involved in an enzyme pathway may be up-regulated to increase the activity of their encoded function(s). For example, additional copies of selected genes may be introduced into the host cell on multicopy plasmids such as pBR322. Such genes may also be integrated into the chromosome with appropriate regulatory sequences that result in increased activity of their encoded functions. The target genes may be modified so as to be under the control of non-native promoters or altered native promoters. Endogenous promoters can be altered in vivo by mutation, deletion, and/or substitution.

Down-Regulation:

Alternatively, it may be useful to reduce or eliminate the expression of certain genes relative to a given activity level.

For the purposes of this invention, it is useful to distinguish between reduction and elimination. The terms "down regulation" and "down-regulating" of a gene refers to a reduction, but not a total elimination, of the activity of the encoded protein. Methods of down-regulating and disrupting genes are known to those of skill in the art.

Down-regulation can occur by deletion, insertion, or alteration of coding regions and/or regulatory (promoter) regions. Specific down regulations may be obtained by random mutation followed by screening or selection, or, where the gene sequence is known, by direct intervention by molecular biology methods known to those skilled in the art. A particularly useful, but not exclusive, method to effect down-regulation is to alter promoter strength.

Disruption:

Disruptions of genes may occur, for example, by 1) deleting coding regions and/or regulatory (promoter) regions, 2) inserting exogenous nucleic acid sequences into coding regions and/regulatory (promoter) regions, and 3) altering coding regions and/or regulatory (promoter) regions (for example, by making DNA base pair changes). Such changes would either prevent expression of the protein of interest or result in the expression of a protein that is non-functional. Specific disruptions may be obtained by random mutation followed by screening or selection, or, in cases where the gene sequences in known, specific disruptions may be obtained by direct intervention using molecular biology methods know to those skilled in the art. A particularly useful method is the deletion of significant amounts of coding regions and/or regulatory (promoter) regions.

Methods of altering recombinant protein expression are known to those skilled in the art, and are discussed in part in Baneyx, *Curr. Opinion Biotech.* (1999) 10:411; Ross, et al., *J. Bacteriol.* (1998) 180:5375; deHaseth, et al., *J. Bacteriol.* (1998) 180:3019; Smolke and Keasling, *Biotech. And Bioengineeering* (2002) 80:762; Swartz, *Curr. Opinions Biotech.* (2001) 12:195; and Ma, et al., *J. Bacteriol.* (2002) 184: 5733.

Alterations in the 1,3-propanediol Production Pathway

Representative Enzyme Pathway. The production of 1,3-propanediol from glucose can be accomplished by the following series of steps. This series is representative of a number of pathways known to those skilled in the art. Glucose is converted in a series of steps by enzymes of the glycolytic pathway to dihydroxyacetone phosphate (DHAP) and 3-phosphoglyceraldehyde (3-PG). Glycerol is then formed by either hydrolysis of DHAP to dihydroxyacetone (DHA) followed by reduction, or reduction of DHAP to glycerol 3-phosphate (G3P) followed by hydrolysis. The hydrolysis step can be catalyzed by any number of cellular phosphatases, which are known to be non-specific with respect to their substrates, or the activity can be introduced into the host by recombination. The reduction step can be catalyzed by a $NAD^+$ (or $NADP^+$) linked host enzyme or the activity can be introduced into the host by recombination. It is notable that the dha regulon contains a glycerol dehydrogenase (E.C. 1.1.1.6) that catalyzes the reversible reaction of Equation 3.

Glycerol→3-HPA+H$_2$O  (Equation 1)

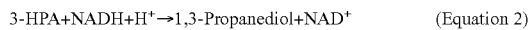
3-HPA+NADH+H$^+$→1,3-Propanediol+NAD$^+$  (Equation 2)

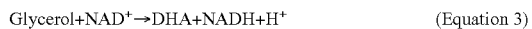
Glycerol+NAD$^+$→DHA+NADH+H$^+$  (Equation 3)

Glycerol is converted to 1,3-propanediol via the intermediate 3-hydroxy-propionaldehyde (3-HPA) as has been described in detail above. The intermediate 3-HPA is produced from glycerol, Equation 1, by a dehydratase enzyme that can be encoded by the host or can be introduced into the host by recombination. This dehydratase can be glycerol dehydratase (E.C. 4.2.1.30), diol dehydratase (E.C. 4.2.1.28) or any other enzyme able to catalyze this transformation. Glycerol dehydratase, but not diol dehydratase, is encoded by the dha regulon. 1,3-Propanediol is produced from 3-HPA, Equation 2, by a $NAD^+$-(or $NADP^+$) linked host enzyme or the activity can be introduced into the host by recombination. This final reaction in the production of 1,3-propanediol can be catalyzed by 1,3-propanediol dehydrogenase (E.C. 1.1.1.202) or other alcohol dehydrogenases.

Mutations and transformations that affect carbon channeling. A variety of mutant microorganisms comprising variations in the 1,3-propanediol production pathway will be useful in the present invention. Mutations which block alternate pathways for intermediates of the 1,3-propanediol production pathway would also be useful to the present invention. For example, the elimination of glycerol kinase prevents glycerol, formed from G3P by the action of G3P phosphatase, from being re-converted to G3P at the expense of ATP. Also, the elimination of glycerol dehydrogenase (for example, gldA) prevents glycerol, formed from DHAP by the action of NADH-dependent glycerol-3-phosphate dehydrogenase, from being converted to dihydroxyacetone. Mutations can be directed toward a structural gene so as to impair or improve the activity of an enzymatic activity or can be directed toward a regulatory gene, including promoter regions and ribosome binding sites, so as to modulate the expression level of an enzymatic activity.

It is thus contemplated that transformations and mutations can be combined so as to control particular enzyme activities for the enhancement of 1,3-propanediol production. Thus, it is within the scope of the present invention to anticipate modifications of a whole cell catalyst which lead to an increased production of 1,3-propanediol.

The present invention utilizes a preferred pathway for the production of 1,3-propanediol from a sugar substrate where the carbon flow moves from glucose to DHAP, G3P, Glycerol, 3-HPA, and finally to 1,3-propanediol. The present production strains have been engineered to maximize the metabolic efficiency of the pathway by incorporating various deletion mutations that prevent the diversion of carbon to non-productive compounds. Glycerol may be diverted from conversion to 3HPA by transformation to either DHA or G3P via glycerol dehydrogenase or glycerol kinase as discussed above. Accordingly, the present production strains contain deletion mutations in the gldA and glpK genes. Similarly DHAP may be diverted to 3-PG by triosephosphate isomerase, thus the present production microorganism also contains a deletion mutation in this gene. The present method additionally incorporates a dehydratase enzyme for the conversion of glycerol to 3HPA, which functions in concert with the reactivation factor, encoded by orfX and orfZ of the dha regulon. Although conversion of the 3HPA to 1,3-propanediol is typically accomplished via a 1,3-propanediol oxidoreductase, the present method utilizes a non-specific catalytic activity that produces greater titers and yields of the final product, 1,3-propanediol. In such a process, titers of 1,3-propanediol of at least 10 g/L are achieved, where titers of 200 g/L are expected.

Alternatively, an improved process for 1,3-propanediol production may utilize glycerol or dihydroxyacetone as a substrate where the pathway comprises only the last three substrates, glycerol→3HPA→1,3-propanediol. In such a process, the oxidoreductase is again eliminated in favor of the non-specific catalytic activity (expected to be an alcohol dehydrogenase), however the need for deletion mutations are nullified by the energy considerations of adding glycerol to the culture. In such as process titers of 1,3-propanediol of at least 71 g/L are achieved where titers of 200 g/L are expected.

Similarly it is within the scope of the invention to provide mutants of wild-type microorganisms that have been modified by the deletion or mutation of the dhaT activity to create improved 1,3-propandiol producers. For example, microorganisms, which naturally contain all the elements of the dha regulon, may be manipulated so as to inactivate the dhaT gene encoding the 1,3-propanediol oxidoreductase activity. These microorganisms will be expected to produce higher yields and titers of 1,3-propanediol, mediated by the presence of an endogenous catalytic activity, expected to be an alcohol dehydrogenase. Examples of such microorganisms include but are not limited to *Klebsiella* sp., *Citrobacter* sp., and *Clostridium* sp.

Media and Carbon Substrates

Fermentation media in the present invention must contain suitable carbon substrates. Suitable substrates may include but are not limited to monosaccharides such as glucose and fructose and oligosaccharides such as lactose or sucrose.

In the present invention, the preferred carbon substrate is glucose.

In addition to an appropriate carbon source, fermentation media must contain suitable minerals, salts, cofactors, buffers and other components, known to those skilled in the art, suitable for the growth of the cultures and promotion of the enzymatic pathway necessary for 1,3-propanediol production. Particular attention is given to Co(II) salts and/or vitamin $B_{12}$ or precursors thereof.

Adenosyl-cobalamin (coenzyme $B_{12}$) is an essential cofactor for dehydratase activity. Synthesis of coenzyme $B_{12}$ is found in prokaryotes, some of which are able to synthesize the compound de novo, for example, *Escherichia blattae*, *Klebsiella* species, *Citrobacter* species, and *Clostridium* species, while others can perform partial reactions. *E. coli*, for example, cannot fabricate the corrin ring structure, but is able to catalyze the conversion of cobinamide to corrinoid and can introduce the 5'-deoxyadenosyl group. Thus, it is known in the art that a coenzyme $B_{12}$ precursor, such as vitamin $B_{12}$, need be provided in *E. coli* fermentations.

Vitamin $B_{12}$ additions to *E. coli* fermentations may be added continuously, at a constant rate or staged as to coincide with the generation of cell mass, or may be added in single or multiple bolus additions. Preferred ratios of vitamin $B_{12}$ (mg) fed to cell mass (OD550) are from 0.06 to 0.60. Most preferred ratios of vitamin $B_{12}$ (mg) fed to cell mass (OD550) are from 0.12 to 0.48.

Although vitamin $B_{12}$ is added to the transformed *E. coli* of the present invention it is contemplated that other microorganisms, capable of de novo $B_{12}$ biosynthesis will also be suitable production cells and the addition of $B_{12}$ to these microorganisms will be unnecessary.

Culture Conditions:

Typically cells are grown at 35° C. in appropriate media. Preferred growth media in the present invention are common commercially prepared media such as Luria Bertani (LB) broth, Sabouraud Dextrose (SD) broth or Yeast medium (YM) broth. Other defined or synthetic growth media may also be used and the appropriate medium for growth of the particular microorganism will be known by someone skilled in the art of microbiology or fermentation science. The use of agents known to modulate catabolite repression directly or indirectly, e.g., cyclic adenosine 2':3'-monophosphate, may also be incorporated into the reaction media. Similarly, the use of agents known to modulate enzymatic activities (e.g., methyl viologen) that lead to enhancement of 1,3-propanediol production may be used in conjunction with or as an alternative to genetic manipulations.

Suitable pH ranges for the fermentation are between pH 5.0 to pH 9.0, where pH 6.0 to pH 8.0 is preferred as the initial condition.

Reactions may be performed under aerobic or anaerobic conditions where aerobic, anoxic, or anaerobic conditions are preferred based on the requirements of the microorganism.

Fed-batch fermentations may be performed with carbon feed, for example, glucose, limited or excess.

Batch and Continuous Fermentations:

The present process employs a batch method of fermentation. Classical batch fermentation is a closed system where the composition of the media is set at the beginning of the fermentation and is not subject to artificial alterations during the fermentation. Thus, at the beginning of the fermentation the media is inoculated with the desired microorganism or microorganisms and fermentation is permitted to occur adding nothing to the system. Typically, however, "batch" fermentation is batch with respect to the addition of carbon source and attempts are often made at controlling factors such as pH and oxygen concentration. In batch systems the metabolite and biomass compositions of the system change constantly up to the time the fermentation is stopped. Within batch cultures cells moderate through a static lag phase to a high growth log phase and finally to a stationary phase where growth rate is diminished or halted. If untreated, cells in the stationary phase will eventually die. Cells in log phase generally are responsible for the bulk of production of end product or intermediate.

A variation on the standard batch system is the Fed-Batch system. Fed-Batch fermentation processes are also suitable in the present invention and comprise a typical batch system with the exception that the substrate is added in increments as the fermentation progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen and the partial pressure of waste gases such as $CO_2$. Batch and Fed-Batch fermentations are common and well known in the art and examples may be found in Brock, supra.

Although the present invention is performed in batch mode it is contemplated that the method would be adaptable to continuous fermentation methods. Continuous fermentation is an open system where a defined fermentation media is added continuously to a bioreactor and an equal amount of conditioned media is removed simultaneously for processing. Continuous fermentation generally maintains the cultures at a constant high density where cells are primarily in log phase growth.

Continuous fermentation allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Continuous systems strive to maintain steady state growth conditions and thus the cell loss due to media being drawn off must be balanced against the cell growth rate in the fermentation.

Methods of modulating nutrients and growth factors for continuous fermentation processes as well as techniques for maximizing the rate of product formation are well known in the art of industrial microbiology and a variety of methods are detailed by Brock, supra.

It is contemplated that the present invention may be practiced using batch, fed-batch or continuous processes and that any known mode of fermentation would be suitable. Additionally, it is contemplated that cells may be immobilized on a substrate as whole cell catalysts and subjected to fermentation conditions for 1,3-propanediol production.

Identification and Purification of 1,3-propanediol:

Methods for the purification of 1,3-propanediol from fermentation media are known in the art. For example, propanediols can be obtained from cell media by subjecting the reaction mixture to extraction with an organic solvent, distillation, and column chromatography (U.S. Pat. No. 5,356,812). A particularly good organic solvent for this process is cyclohexane (U.S. Pat. No. 5,008,473).

1,3-Propanediol may be identified directly by submitting the media to high pressure liquid chromatography (HPLC) analysis. Preferred in the present invention is a method where fermentation media is analyzed on an analytical ion exchange column using a mobile phase of 0.01 N sulfuric acid in an isocratic fashion.

General Methods and Materials

Procedures for phosphorylations, ligations and transformations are well known in the art. Techniques suitable for use in the following examples may be found in Sambrook, J. et al., supra.

Materials and methods suitable for the maintenance and growth of bacterial cultures are well known in the art. Techniques suitable for use in the following examples may be found in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994) or Thomas D. Brock in *Biotechnology: A Textbook of Industrial Microbiology*, Second Edition (1989) Sinauer Associates, Inc., Sunderland, Mass. All reagents and materials used for the growth and maintenance of bacterial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.) unless otherwise specified.

The meaning of abbreviations is as follows: "hr" means hour(s), "min" means minute(s), "sec" means second(s), "d" means day(s), "mL" means milliliters, "L" means liters, 50 amp is 50 µg/mL ampicillin, and LB-50 amp is Luria-Bertani broth containing 50 µg/mL ampicillin.

Within the tables the following abbreviations are used. "Con." is conversion, "Sel." is selectivity based on carbon, and "nd" is not detected.

Strains and vectors used and constructed in the following examples are listed in the chart below:

| Name | Alternate name | Phenotype |
|---|---|---|
| FM5 | | |
| RJF10 | | FM5 glpK- |
| KLP23 | | FM5 glpK- gldA- |
| WO2001012833 A2 | | |
| KLndh81 | | FM5 glpk- gldA- ndh- |
| KLpts7 | | FM5 glpk- gldA- ndh- ptsHlcrr- KmR |
| KlgalP-trc | | FM5 glpk- gldA- ndh- ptsHlcrr- KmR galPp-trc |
| KLGG | | FM5 glpk- gldA- ndh- ptsHlcrr- KmR galPp-trc glkp-trc |
| KLGG ΔarcA | | FM5 glpk- gldA- ndh- ptsHlcrr- KmR galPp-trc glkp-trc arcA- |
| KLGG ΔarcA Δedd | FMP | FM5 glpk- gldA- ndh- ptsHlcrr- KmR galPp-trc glkp-trc arcA- edd- |
| Selected FMP | FMP'::Km | FM5 glpk- gldA- ndh- ptsHlcrr- KmR galPp-trc glkp-trc* arcA- edd- |
| FMP'::Km 1.5gapA | | FM5 glpk- gldA- ndh- ptsHlcrr- KmR galPp-trc glkp-trc* arcA- edd- gapAp-1.5 |
| FMP' 1.5 gapA | | FM5 glpk- gldA- ndh- ptsHlcrr- galPp-trc glkp-trc* arcA- edd- gapAp-1.5 |
| FMP' 1.5 gapA ΔmgsA | | FM5 glpk- gldA- ndh- ptsHlcrr- galPp-trc glkp-trc* arcA- edd- gapAp-1.5 mgsA- |
| FMP' 1.5 gap Δmgs 1.6ppc | Triple | FM5 glpk- gldA- ndh- ptsHlcrr- galPp-trc glkp-trc* arcA- edd- gapAp-1.5 mgsA- ppcp-1.6 |
| Triple 1.6 btuR | | FM5 glpk- gldA- ndh- ptsHlcrr- galPp-trc glkp-trc* arcA- edd- gapAp-1.5 mgsA- ppcp-1.6 yciK- btuRp-1.6 |
| Triple 1.6 btuR 1.6yqhD | | FM5 glpk- gldA- ndh- ptsHlcrr- galPp-trc glkp-trc* arcA- edd- gapAp-1.5 mgsA- ppcp-1.6 yciK- btuRp-1.6 yqhC- yqhDp-1.6 |
| Triple 1.6 btuR 1.6yqhD ΔackA-pta | Triple Triple | FM5 glpk- gldA- ndh- ptsHlcrr- galPp-trc glkp-trc* arcA- edd- gapAp-1.5 mgsA- ppcp-1.6 yciK- btuRp-1.6 yqhC- yqhDp-1.6 ackA- pta- |
| Triple Triple ΔaldA | | FM5 glpk- gldA- ndh- ptsHlcrr- galPp-trc glkp-trc* arcA- edd- gapAp-1.5 mgsA- ppcp-1.6 yciK- btuRp-1.6 yqhC- yqhDp-1.6 ackA- pta- aldA- |
| Triple Triple ΔaldB | | FM5 glpk- gldA- ndh- ptsHlcrr- galPp-trc glkp-trc* arcA- edd- gapAp-1.5 mgsA- ppcp-1.6 yciK- btuRp-1.6 yqhC- yqhDp-1.6 ackA- pta- aldB- |
| Triple Triple ΔaldA ΔaldB | | FM5 glpk- gldA- ndh- ptsHlcrr- galPp-trc glkp-trc* arcA- edd- gapAp-1.5 mgsA- ppcp-1.6 yciK- btuRp-1.6 yqhC- yqhDp-1.6 ackA- pta- aldA- aldB- |

Strains:

KLP23 (WO 2001012833 A2),

RJ8.n (ATCC PTA-4216),

MG 1655 ATCC 700926 (commercially available)

| Plasmids: | |
|---|---|
| pAH48 | WO 9821340 A1 |
| pDT29 | WO 2001012833 A2 |
| pKP32 | WO 2001012833 A2 |
| pSYCO101 | SEQ ID NO: 65. |
| pSYCO103 | SEQ ID NO: 66. |
| pSYCO106 | SEQ ID NO: 67. |
| pSYCO109 | SEQ ID NO: 68. |

The plasmids pKD3, pKD4, pKD13 and pKD46, and pCP20 have been described (Datsenko and Wanner, supra). The plasmids pLoxCat2 and pJW168 have been described (Palmeros et al., supra).

Chromosomal Integration for Gene Knockouts, Promoter Replacements and Introduction of Chromosomal Mutations.

To integrate DNA into a specific region of the chromosome, homology of the inserting DNA to the targeted chromosomal site and a selectable marker are required. It is advantageous if the marker can be easily removed after integration. The loxP/Cre recombinase system from P1 phage and the FRT/Flp recombinase system from yeast provide a mechanism to remove the marker. The loxP and FRT sites are recognition sites for the Cre and Flp recombinases. Cre and Flp are site specific recombinases, which excise the intervening DNA from the directly repeated recognition sites.

The integration cassette containing homologous arms to the targeted chromosomal site and encoding a selectable marker flanked by loxP [Palmeros et al. *Gene* 247, 255-264 (2000)] or FRT [Datsenko and Wanner, *Proc. Natl. Acad. Sci. USA* 97, 6640-6645 (2000)] sites is transformed into target cells harboring pKD46 (Datsenko and Wanner, supra). Successful integrants are selected by growth of the cells in the presence of the antibiotic. Subsequently, pKD46 is cured from the cells and the recombinase plasmids are then introduced into the integrants for removal of the antibiotic gene. Strains integrated with a loxP cassette are transformed with pJW168 that encodes Cre recombinase (Palmeros et al, supra). Strains containing a FRT cassette are transformed with pCP20 that encodes Flp recombinase (Datsenko and Wanner, supra). After removal of the integrated marker, the recombinase plasmids are cured from the strain.

P1 vir transduction were performed as previously described [Miller, J. H., A short course in bacterial genetics. A laboratory manual and handbook for *Escherchia coli* and related bacteria (1992), Cold Spring Harbor Laboratory, Cold Spring Harbor, N.Y.].

Enzyme Assays

Assays for Glucokinase (Glk) Activity:

Glucokinase (Glk) activity was assayed by following the conversion of glucose to glucose-6-phosphate spectrophotometrically at 340 nm by coupling the glucokinase reaction with that of glucose-6-phosphate dehydrogenase (E.C. 1.1.1.49). The assay contained 0.5 mM NADP, 5 mM ATP, 5 mM MgCl, and 2 units of glucose-6-phosphate dehydrogenase in 100 mM phosphate buffer, pH 7.2. Alternative assays may be found in T. E. Barman, Enzyme Handbook (1985), Springer-Verlag, Berlin.

Assay for Glyceraldehyde-3-phosphate dehydrogenase Activity:

Assay for Glyceraldehyde-3-phosphate dehydrogenase activity was measured in cell-free extracts by the appearance of NADH. An ultracentrifuged (50,000×g, 1 h, 4° C.) cell-free supernatant was partially purified using an ion exchange column prior to assay. The assay contained 0.2 mM glyceraldehyde 3-phosphate, 2.5 mM NAD$^+$, 2 mM EDTA, 5 mM cysteamine, 20 mM potassium phosphate and 40 mM triethanolamine at pH 8.9. Alternative assays may be found in T. E. Barman, supra.

Assay for Phosphoenolpyruvate Carboxylase (Ppc) Activity:

Phosphoenolpyruvate carboxylase (Ppc) activity was measured in cell-free extracts by a coupled assay (Flores and Gancedo, *FEBS Lett.* 412, 531-534 (1997)). This method involved incubating at room temperature a ultracentrifuged (50,000×g, 1 h, 4° C.) cell-free extract sample in a cuvette that contained 0.22 mM NADH, 1.1 mM phosphoenolpyruvate (PEP), 0.25 mM acetyl-CoA, and 6 U of malate dehydrogenase (MDH) in 0.1 M Tris/HCl buffer, pH 8.5, with 11 mM sodium bicarbonate and 11 mM magnesium sulfate, in a total volume of 1.0 mL. A background rate of the reaction of enzyme and NADH was first determined at 340 nm in the absence of PEP. The second substrate, PEP, was subsequently added and the absorbance change over time was further monitored. Ppc activity was defined by subtracting the background rate from the gross rate. Alternative assays may be found in T. E. Barman, supra.

Assays for Dehydratase Enzymes:

Dehydratase activity in cell-free extracts was determined using either glycerol or 1,2-propanediol as substrate. Typically, cell-free extracts were prepared by cell disruption using a french press followed by centrifugation of the cellular debris. The assay, based on the reaction of aldehydes with methylbenzo-2-thiazolone hydrazone, has been described by Forage and Foster (*Biochim. Biophys. Acta* 569, 249 (1979)).

Honda et al. (*J. Bacteriol.* 143, 1458 (1980)) disclose an assay that measures the reactivation of dehydratases. Dehydratase activity was determined in toluenized whole cells, with and without ATP, using either glycerol or 1,2-propanediol as substrate. Reactivation was determined by the ratio of product formation with versus without the ATP addition. Product formation (3-HPA or propionaldehyde when glycerol or 1,2-propanediol is used as substrate, respectively) was measured directly, using HPLC, or indirectly, using the methylbenzo-2-thiazolone hydrazone reagent. Alternatively, product formation was determined by coupling the conversion of the aldehyde to its respective alcohol using a NADH linked alcohol dehydrogenase and monitoring the disappearance of NADH.

Assays for 1,3-propanediol oxidoreductase:

The activity of 1,3-propanediol oxidoreductase, sometimes referred to as 1,3-propanediol dehydrogenase, was determined for cell-free extracts in solution or in slab gels using 1,3-propanediol and NAD$^+$ as substrates has been described (Johnson and Lin, *J. Bacteriol.* 169, 2050 (1987)). Alternatively, the conversion of 3-HPA and NADH to 1,3-propanediol and NAD$^+$ was determined by the disappearance of NADH. The slab gel assay has the potential advantage of separating the activity of 1,3-propanediol oxidoreductase (dhaT) from that of non-specific alcohol dehydrogenases by virtue of size separation. The native molecular weights of 1,3-propanediol oxidoreductases (dhaT) from *Citrobacter frendii*, *Klebsiella pneumoniae*, and *Clostridium pasteurianum* are unusually large, on the order of 330,000 to 440,000 daltons. *Lactobacillus brevis* and *Lactobacillus buchneri* contain dehydratase associated 1,3-propanediol oxidoreductases with properties similar to those of known 1,3-propanediol oxidoreductases (dhaT).

Assays for Glycerol 3-phosphate dehydrogenase Activity:

A procedure was used as modified below from a method published by Bell et al., (*J. Biol. Chem.* 250, 7153 (1975)). This method involved incubating a cell-free extract sample in a cuvette that contained 0.2 mM NADH, 2.0 mM dihydroxyacetone phosphate (DHAP), and enzyme in 0.1 M Tris/HCl, pH 7.5 buffer with 5 mM DTT, in a total volume of 1.0 mL at 30° C. A background rate of the reaction of enzyme and NADH was first determined at 340 nm for at least 3 min. The second substrate, DHAP, was subsequently added and the absorbance change over time was further monitored for at least 3 min. G3PDH activity was defined by subtracting the background rate from the gross rate.

Assay for glycerol-3-phosphatase Activity:

The assay for enzyme activity was performed by incubating the extract with an organic phosphate substrate in a bis-Tris or MES and magnesium buffer, pH 6.5. The substrate used was either l-α-glycerol phosphate, or d,l-α-glycerol phosphate. The final concentrations of the reagents in the assay are: buffer (20 mM, bis-Tris or 50 mM MES); $MgCl_2$ (10 mM); and substrate (20 mM). If the total protein in the sample was low and no visible precipitation occurs with an acid quench, the sample was conveniently assayed in the cuvette. This method involved incubating an enzyme sample in a cuvette that contained 20 mM substrate (50 μL, 200 mM), 50 mM MES, 10 mM $MgCl_2$, pH 6.5 buffer. The final phosphatase assay volume was 0.5 mL. The enzyme-containing sample was added to the reaction mixture; the contents of the cuvette were mixed and then the cuvette was placed in a circulating water bath at T=37° C. for 5 to 120 min, the length of time depending on whether the phosphatase activity in the enzyme sample ranged from 2 to 0.02 U/mL. The enzymatic reaction was quenched by the addition of the acid molybdate reagent (0.4 mL). After the Fiske SubbaRow reagent (0.1 mL) and distilled water (1.5 mL) were added, the solution was mixed and allowed to develop. After 10 min, to allow full color development, the absorbance of the samples was read at 660 nm using a Cary 219 UV/vis spectrophotometer. The amount of inorganic phosphate released was compared to a standard curve that was prepared by using a stock inorganic phosphate solution (0.65 mM) and preparing 6 standards with final inorganic phosphate concentrations ranging from 0.026 to 0.130 μmol/mL.

Assay for Glycerol Kinase Activity:

An appropriate amount of enzyme, typically a cell-free crude extract, was added to a reaction mixture containing 40 mM ATP, 20 mM $MgSO_4$, 21 mM uniformly $^{13}C$ labeled glycerol (99%, Cambridge Isotope Laboratories), and 0.1 M Tris-HCl, pH 9 for 75 min at 25° C. The conversion of glycerol to glycerol 3-phosphate was detected by $^{13}C$-NMR (125 MHz): glycerol (63.11 ppm, 6, J=41 Hz and 72.66 ppm, t, J=41 Hz); glycerol 3-phosphate (62.93 ppm, 6, J=41 Hz; 65.31 ppm, br d, J=43 Hz; and 72.66 ppm, dt, J=6, 41 Hz).

NADH-linked Glycerol Dehydrogenase Assay:

NADH-linked glycerol dehydrogenase activity (gldA) in cell-free extracts from *E. coli* strains was determined after protein separation by non-denaturing polyacrylamide gel electrophoresis. The conversion of glycerol plus $NAD^+$ to dihydroxyacetone plus NADH was coupled with the conversion of 3-[4,5-dimethylthiazol-2-yl]-2,5-diphenyltetrazolium bromide (MTT) to a deeply colored formazan, using phenazine methosulfate (PMS) as mediator (Tang et al., *J. Bacteriol.* 140, 182 (1997)).

Electrophoresis was performed in duplicate by standard procedures using native gels (8-16% TG, 1.5 mm, 15 lane gels from Novex, San Diego, Calif.). Residual glycerol was removed from the gels by washing 3× with 50 mM Tris or potassium carbonate buffer, pH 9 for 10 min. The duplicate gels were developed, with and without glycerol (approximately 0.16 M final concentration), in 15 mL of assay solution containing 50 mM Tris or potassium carbonate, pH 9, 60 mg ammonium sulfate, 75 mg $NAD^+$, 1.5 mg MTT, and 0.5 mg PMS.

The presence or absence of NADH-linked glycerol dehydrogenase activity in *E. coli* strains (gldA) was also determined, following polyacrylamide gel electrophoresis, by reaction with polyclonal antibodies raised to purified *K. pneumoniae* glycerol dehydrogenase (dhaD).

Isolation and Identification of 1,3-propanediol:

HPLC analysis of fermentation products. The conversion of glucose to 1,3-propanediol was monitored by HPLC. Analyses were performed using standard chromatography. One suitable method utilized a Waters Alliance HPLC system using R1 detection. Samples were injected onto a Aminex HPX87H column (7.8 mm×300 mm, Biorad, Hercules, Calif.) equipped with a Cation H Refill Cartridge precolumn (4.6 mm×30 mm, Biorad, Hercules, Calif.), temperature controlled at 50° C., using 5 mM $H_2SO_4$ as mobile phase at a flow rate of 0.4 mL/min. The system was calibrated weekly against standards of known concentration. Typically, the retention times of glucose, glycerol, 1,3-propanediol, and acetic acid were 12.7 min, 19.0 min, 25.2 min, and 21.5 min, respectively.

GC/MS Analysis of Fermentation Methods.

Production of 1,3-propanediol was confirmed by GC/MS. Analyses were performed using standard techniques and materials available to one of skill in the art of GC/MS. One suitable method utilized a Hewlett Packard 5890 Series II gas chromatograph coupled to a Hewlett Packard 5971 Series mass selective detector (EI) and a HP-INNOWax column (30 m length, 0.25 mm i.d., 0.25 micron film thickness). The retention time and mass spectrum of 1,3-propanediol generated were compared to that of authentic 1,3-propanediol (m/e: 57, 58).

An alternative method for GC/MS involved derivatization of the sample. To 1.0 mL of sample (e.g., culture supernatant) was added 30 μL of concentrated (70% v/v) perchloric acid. After mixing, the sample was frozen and lyophilized. A 1:1 mixture of bis(trimethylsilyl)trifluoroacetamide:pyridine (300 μL) was added to the lyophilized material, mixed vigorously and placed at 65° C. for one h. The sample was clarified of insoluble material by centrifugation. The resulting liquid partitioned into two phases, the upper of which was used for analysis. The sample was chromatographed on a DB-5 column (48 m, 0.25 mm I.D., 0.25 μm film thickness; from J&W Scientific) and the retention time and mass spectrum of the 1,3-propanediol derivative obtained from culture supernatants were compared to that obtained from authentic standards. The mass spectra of TMS-derivatized 1,3-propanediol contains the characteristic ions of 205, 177, 130 and 115 AMU.

Medium Composition

TM2 medium (TM2) is a base recipe to which carbon source (typically glucose, at 20 g/L or 40 g/L), appropriate antibiotics, and other components are added. TM2 medium contains the following components: $K_2HPO_4$ (13.6 g/L), $KH_2PO4$ (13.6 g/L), $MgSO_4.7H_2O$ (2 g/L), citric acid monohydrate (2 g/L), ferric ammonium citrate (0.3 g/L), $(NH_4)_2SO_4$ (3.2 g/L), yeast extract (5 g/L), solution of trace elements (1 ml). The pH is adjusted to 6.8. The solution of trace elements contains: citric acid $H_2O$ (4.0 g/L), $MnSO_4.H_2O$ (3.0 g/L), NaCl (1.0 g/L), $FeSO_4.7H_2O$ (0.10 g/L), $CoCl_2.6H_2O$ (0.10 g/L), $ZnSO_4.7H_2O$ (0.10 g/L), $CuSO_4.5H_2O$ (0.010 g/L), $H_3BO_3$ (0.010 g/L), and $Na_2MoO_4.2H_2O$ (0.010 g/L).

TM3 medium (TM3) is identical to TM2 medium except that it contains 0.5 g/L yeast extract.

LB medium (LB) contains 5 g/L yeast extract, 10 g/L tryptone, and 10 g/L NaCl. LB plates (or LA) are LB medium+2% agar. 2YT medium (2YT) contains 10 g/L yeast extract, 16 g/L tryptone, and 10 g/L NaCl. Soy broth with glucose (SBG1%) contains 10 g/L Soytone (Difco), 5 g/L yeast extract, 10 g/L NaCl, and 10 g/L glucose.

Fermentation Protocol (14 L)

Shake flask cultures of all strains described (KLP23, RJ8.n, MB 1655) were grown on either 2YT medium or LB containing the appropriate antibiotics as detailed in the examples to make the pre-culture for inoculation of the fermenters. Cultures were started from either frozen seed vials prepared with 15% glycerol as a cryoprotectant or from a single colony grown on fresh LA plates with 50 mg/L spectinomycin. Cultures started with a frozen vial were grown in 500 mL of the specified medium in a 2 L flask; when a single colony was used to start the pre-culture, it was placed in 30 mL of the specified medium in a 250 mL baffled flask. The cultures were incubated at 34° C. and 300 rpm shaking to an $OD_{550}$ of approximately 1.0 AU was reached and used to seed the fermenter. In some cases, a seed fermenter was used to provide a larger pre-culture for inoculating a production fermenter. Seed fermenters were generally identical to production fermenters except that vitamin $B_{12}$ was not added to the seed tank. Details about the procedures for using seed fermenters are described in the pertinent examples.

Seed and production fermenters were prepared with the same medium, containing $KH_2PO_4$ (7.5 g/L), $MgSO_4.7H_2O$ (2 g/L), citric acid monohydrate (2 g/L), ferric ammonium citrate (0.3 g/L), $CaCl_2.2H_2O$ (0.2 g/L), sulfuric acid (98%; 1.2 mL/L), Mazu DF204 (0.4 mL/L) as antifoam, yeast extract (5 g/L), solution of trace elements (10 ml/L). The solution of trace elements contains: citric acid $H_2O$ (4.0 g/L), $MnSO_4.H_2O$ (3.0 g/L), NaCl (1.0 g/L), $FeSO_4.7H_2O$ (0.10 g/L), $COCl_2.6H_2O$ (0.10 g/L), $ZnSO_4. 7H_2O$ (0.10 g/L), $CuSO_4.5H_2O$ (0.010 g/L), $H_3BO_3$ (0.010 g/L), and $Na_2MoO_4.2H_2O$ (0.010 g/L). After sterilization, the pH was adjusted to 6.8 with 20-28% $NH_4OH$ and additions of glucose (to 10-25 g/L from a 60-67% (w/w) solution) and the appropriate antibiotics (see specific examples for details) were made. The fermenter volume after inoculation was 6 liters.

A 14 L stirred tank fermenter was prepared with the medium described above. The temperature was controlled at 34° C. and aqueous ammonia (20-28 weight %) was used to control pH at 6.8. Backpressure was controlled at 0.5 barg and dO control set at 5%. Except for minor excursions, glucose concentration was maintained between 0 g/L and 25 g/L with a 60-67% (w/w) feed. Vitamin $B_{12}$ additions and any other changes to the general procedure described here are noted in the examples.

Molar yield, as either fraction or %, represents (mol glycerol produced+mol 1,3-propanediol produced)/(mol glucose consumed). Weight yield, generally given as %, represents (g 1,3-propanediol produced)/(g glucose consumed).

EXAMPLE 1

Construction of NADH Dehydrogenase II Minus (Δndh) E. coli Strains for the Production of 1,3-propanediol Construction of KLndh81.

An ndh mutation was obtained by interrupting the coding region with a loxP511 cassette. The ndh gene (for reference, see GenBank, Accession # U00096), with upstream and downstream flanking regions, was PCR amplified from E. coli MG1655 and cloned. The ndh cassette was digested with Stu I, cutting roughly in the middle of the gene, and a loxP511-Cat-loxP511 cassette was cloned into this site with the cat gene in the opposite orientation relative to the ndh gene. The loxP511-Cat-loxP511 cassette was obtained from the plasmid pLoxCat27 [SEQ ID NO:1] by digestion with Spe I and EcoR V, followed by fill-in to generate blunt ends, and gel purification of the 1.1 kb fragment. The loxP511 site is a variant of the loxP site (Palmeros et al., supra). The ndh::Cat cassette was PCR amplified and electroporated into KLP23 competent cells creating strain KLndh81::Cm. The chloramphenicol marker was removed by the Cre recombinase (Palmeros et al., supra) leaving 96 bp of interrupting sequence containing one loxP511 site. This strain was designated KLndh81. Alternatively, an ndh mutation was obtained by interrupting the coding region with a Cat cassette without loxP sites to give strain KLNDH413.

Construction of RJ8.n.

A cassette containing ndh flanking sequence and loxP511-Cat-loxP511 from Klndh81::Cm was PCR amplified and cloned into pUni/V5-His TOPO [Invitrogen] to create pAH111. The ndh-loxP511-Cat-loxP511 cassette from pAH111 was integrated into strain RJ8/pKD46. Recombinant strains were selected for chloramphenicol resistance. Successful integration of the cassette into ndh was confirmed by PCR. The chloramphenicol marker was removed by using Cre recombinase (Palmeros et al., supra) creating strain RJ8.n.

EXAMPLE 2

Comparison of 1,3-Propanediol and Glycerol Production with E. coli Strains KLP23/pAH48/pDT29 and KLP23/pAH48/pKP32

Strain KLP23 was transformed with plasmids pAH48 and pDT29 or pKP32. Production of 1,3-propanediol (and glycerol) was determined in 14 L fermenters as described in General Methods. Pre-cultures for each fermentation were prepared using frozen vials thawed and grown in 500 mL 2YT with 200 mg/L carbenicillin and 50 mg/L spectinomycin. The full contents of the flask were used to inoculate the fermenter. The fermenter was operated at 35° C. and a d6 set-point of 10%; all other control parameters are as described in General Methods. The vitamin $B_{12}$ strategy for each fermentation is detailed below.

Fermentation with KLP23/pAH48/pDT29.

In this example, vitamin $B_{12}$ (0.075 g/L, 500 mL) was fed, starting 3 h after inoculation, at a rate of 16 mL/h. A representative fermentation summary of the conversion of glucose to 1,3-propanediol (1,3-PD) using E. coli strain KLP23/pAH48/pDT29 is given in Table 2.1. The yield of 1,3-propanediol was 24 wt % (g 1,3-propanediol/g glucose consumed) and a titer of 68 g/L 1,3-propanediol was obtained.

TABLE 2.1

Representative fermentation summary of the conversion of glucose to 1,3-propanediol (1,3-PD) using E. coli strain KLP23/pAH48/pDT29

| Time (h) | OD550 (AU) | DO (%) | Glucose (g/L) | Glycerol (g/L) | 1,3-PD (g/L) |
|---|---|---|---|---|---|
| 0 | 0 | 150 | 12.9 | 0.0 | 0 |
| 6 | 17 | 80 | 8.3 | 3.1 | 1 |
| 12 | 42 | 53 | 2.8 | 12.5 | 9 |
| 18 | 98 | 9 | 5.7 | 12.6 | 32 |
| 24 | 136 | 11 | 32.8 | 12.0 | 51 |
| 30 | 148 | 10 | 12.3 | 13.3 | 62 |
| 32 | 152 | 11 | 12.5 | 14.3 | 65 |
| 38 | 159 | 11 | 1.5 | 17.2 | 68 |

Similar results were obtained with an identical vitamin $B_{12}$ feed at twice the concentration or bolus additions of vitamin $B_{12}$ across the time course of the fermentation. The highest titer obtained was 77 g/L.

Improved Fermentation with KLP23/pAH48/pKP32.

A representative fermentation summary of the conversion of glucose to 1,3-propanediol (1,3-PD) using *E. coli* strain KLP23/pAH48/pKP32 is given in Table 2.2. Vitamin $B_{12}$ (0.150 g/L, 500 mL) was fed, starting 3 h after inoculation, at a rate of 16 mL/h. After 36 h, approximately 2 L of fermentation broth was purged in order to allow for the continued addition of glucose feed. The yield of 1,3-propanediol was 26 wt % (g 1,3-propanediol/g glucose consumed) and a titer of 112 g/L 1,3-propanediol was obtained.

TABLE 2.2

Representative fermentation summary of the improved conversion of glucose to 1,3-propanediol (1,3-PD) using *E. coli* strain KLP23/pAH48/pKP32

| Time (h) | OD550 (AU) | DO (%) | Glucose (g/L) | Glycerol (g/L) | 1,3-PD (g/L) |
|---|---|---|---|---|---|
| 0  | 0   | 148 | 12.8 | 0.0  | 0 |
| 6  | 22  | 84  | 6.9  | 3.3  | 0 |
| 12 | 34  | 90  | 9.7  | 10.4 | 7 |
| 18 | 66  | 43  | 9.3  | 5.9  | 24 |
| 24 | 161 | 9   | 0.2  | 2.5  | 46 |
| 30 | 200 | 10  | 0.2  | 6.0  | 67 |
| 36 | 212 | 10  | 1.2  | 9.7  | 88 |
| 42 | 202 | 2   | 0.1  | 15.5 | 98 |
| 48 | 197 | 12  | 1.2  | 23.8 | 112 |

Similar results were obtained with an identical vitamin $B_{12}$ feed at half the concentration or bolus additions of vitamin $B_{12}$ across the time course of the fermentation. The highest titer obtained was 114 g/L.

EXAMPLE 2A

Comparison of 1,3-Propanediol and Glycerol Production with *E. coli* Strains RJ8/pAH48/pDT29 and RJ8/pAH48/pKP32

RJ8/pAH48pDT29 and RJ8/pAH48/pKP32 pre-cultures were prepared using frozen vials thawed and grown in 500 mL 2YT with 200 mg/L carbenicillin and 50 mg/L spectinomycin. The full contents of the flask were used to inoculate the fermenter. The fermenter was operated at 35° C. and a d6 set-point of 10%; all other control parameters are as described in General Methods. RJ8/pAH48/pKP32 is identical to RJ8/pAH48/pDT29 except that dhaT is deleted. The vitamin $B_{12}$ strategy for each fermentation is detailed below.

Fermentation with RJ8/pAH48/pDT29.

A representative fermentation summary of the conversion of glucose to 1,3-propanediol (1,3-PD) using *E. coli* strain RJ8/pAH48/pDT29 is given in Table 2A.1. Vitamin $B_{12}$ was provided as bolus additions of 2, 16 and 16 mg at 2, 8, and 26 h, respectively. The yield of 1,3-propanediol was 35 wt % (g 1,3-propanediol/g glucose consumed) and a titer of 50.1 g/L 1,3-propanediol was obtained.

TABLE 2A.1

Representative fermentation summary of the conversion of glucose to 1,3-propanediol (1,3-PD) using *E. coli* strain RJ8/pAH48/pDT29

| Time (h) | OD550 (AU) | DO (%) | Glucose (g/L) | Glycerol (g/L) | 1,3-PD (g/L) |
|---|---|---|---|---|---|
| 0  | 0  | 140 | 10.6 | 0.1 | 0.0  |
| 6  | 5  | 107 | 11.1 | 0.5 | 0.4  |
| 10 | 16 | 90  | 8.5  | 1.7 | 1.3  |
| 14 | 25 | 86  | 1.8  | 2.4 | 5.9  |
| 19 | 38 | 53  | 3.5  | 5.9 | 15.4 |
| 25 | 53 | 38  | 0.1  | 9.2 | 26.7 |
| 31 | 54 | 10  | 4.5  | 7.4 | 39.0 |
| 37 | 37 | 23  | 17.2 | 6.0 | 45.0 |
| 43 | 21 | 13  | 9.9  | 7.7 | 50.1 |

Improved Fermentation with RJ8/pAH48/pKP32.

A representative fermentation summary of the conversion of glucose to 1,3-propanediol (1,3-PD) using *E. coli* strain RJ8/pAH48/pKP32 is given in Table 2A.2. Vitamin $B_{12}$ was provided as bolus additions of 48 and 16 mg at approximately 26 and 44 hr, respectively. The yield of 1,3-propanediol was 34 wt % (g 1,3-propanediol/g glucose consumed) and a titer of 129 g/L 1,3-propanediol was obtained.

TABLE 2A.2

Representative fermentation summary of the improved conversion of glucose to 1,3-propanediol (1,3-PD) using *E. coli* strain RJ8/pAH48/pKP32.

| Time (h) | OD550 (AU) | DO (%) | Glucose (g/L) | Glycerol (g/L) | 1,3-PD (g/L) |
|---|---|---|---|---|---|
| 0  | 0   | 150 | 12.6 | 0.1  | 0   |
| 6  | 12  | 113 | 6.0  | 2.6  | 0   |
| 12 | 24  | 99  | 0.0  | 10.6 | 0   |
| 18 | 51  | 76  | 2.4  | 28.9 | 0   |
| 24 | 78  | 82  | 2.4  | 44.2 | 5   |
| 30 | 114 | 70  | 3.8  | 26.9 | 33  |
| 36 | 111 | 72  | 0.0  | 20.0 | 57  |
| 42 | 139 | 65  | 0.1  | 21.9 | 69  |
| 48 | 157 | 36  | 0.1  | 22.4 | 79  |
| 55 | 158 | 25  | 0.2  | 21.4 | 94  |
| 64 | 169 | 14  | 0.1  | 15.8 | 113 |
| 72 | 169 | 12  | 0.1  | 13.4 | 119 |
| 74 | 162 | 14  | 0.1  | 14.8 | 129 |

1,3-Propanediol and Glycerol Production with *E. coli* Strain RJ8.n/pAH48/pKP32.

Strain RJ8.n was transformed with plasmids pAH48 and pKP32. Production of 1,3-propanediol (and glycerol) was determined in 14 L fermenters as described in General Methods. A thawed frozen vial of RJ8.n/pAH48/pKP32 was transferred to 500 mL LB with 200 mg/L carbenicillin and 50 mg/L spectinomycin to prepare the pre-culture. The culture was transferred to a seed fermenter and grown for 16 h before 1 L of the culture was transferred to the production fermenter. At that time, the OD550 had reached over 50 AU and 30 g/L glycerol had accumulated in the broth. Both the seed and production fermenters were operated at 35° C. and a d6 set-point of 10%; all other control parameters are as described in General Methods.

Vitamin $B_{12}$ was added to the production tank in 16 mg boluses at 12 h, 17.3 h, 22.8 h, and 27.5 h. The final titer was 112.7 g/L 3G and the mass yield was 31.6%.

EXAMPLE 3

Construction and Shake Flask Performance of an *E. coli* Strain with a Deletion in the arcA Global Regulator An arcA deletion [for reference, see GenBank, Accession # U00096] was made by replacing 0.6 kb of the coding region with the FRT-CmR-FRT cassette of pKD3. A replacement cassette was amplified with the primer pair SEQ ID NO:2 and SEQ ID NO:3 using pKD3 as the template. The primer SEQ ID NO:2 contains 41 bp of homology to the 5' end of arcA and 20 bp of homology to pKD3. Primer SEQ ID NO:3 contains 42 bp of homology to the 3' end of arcA and 20 bp of homology to pKD3. The PCR product was gel-purified and electroporated into MG1655/pKD46 competent cells. Recombinant strains were selected on LB plates with 12.5 mg/L of chloramphenicol. The deletion of the arcA gene was confirmed by PCR, using the primer pair SEQ ID NO:4 and SEQ ID NO:5. The wild-type strain gives a 0.7 kb PCR product while the recombinant strain gives a characteristic 1.1 kb PCR product. The strain has been designated MG1655 ΔarcA::Cm. A P1 lysate was prepared and used to move the mutation into the strain KLndh81 to form KLndh81 ΔarcA::Cm.

The KLndh81 ΔarcA::Cm strain and KLndh81 control strain were electrotransformed with plasmid pSYCO101. One colony of each strain was incubated 10 h in LB medium with 50 mg/L spectinomycin. A 200 μL volume of these cultures was then transferred to a 250 mL baffled Erlenmeyer flask containing 10 mL TM2 medium with 40 g/L glucose, 50 mg/L spectinomycin, and 2 mg/L vitamin $B_{12}$. The flasks were incubated at 300 rpm and 34° C. for 40 hrs. The results in Table 3 show that the arcA mutation improves the molar yield of glycerol and 1, 3 propanediol production.

TABLE 3

Glycerol and 1,3-propanediol production in
*E. coli* control and ΔarcA::Cm strains

| Strain | Glycerol (g/L) | 1,3 Propanediol (g/L) | OD 550 nm | Molar Yield (mol/mol) |
|---|---|---|---|---|
| KLndh81 pSYCO101 | 5.8 | 10.7 | 29.2 | 0.87 |
| KLndh81 ΔarcA pSYCO101 | 6.8 | 11.4 | 25.9 | 0.95 |

EXAMPLE 4

Construction of Phosphotranserase System Minus (PTS) *E. coli* Strains with TRC Promoters Controlling Expression Levels of Galactose-Proton Symporter (galP) and Glucokinase (glk)

Construction of a loxP-CAT-loxP-Trc Cassette (pTrCm42).

Linear DNA was obtained from plasmid pTrc99a (Pharmacia) digested with HindIII and NcoI, filled with T4 DNA polymerase, circularized and transformed into *E. coli* TOP-10 (Invitrogen, Carlsbad, Calif.). Following selection on Luria-agar plates containing 50 mg/L of carbenicillin, the resulting plasmid (ptrc1) was purified and subjected to restriction enzyme analysis to confirm that the DNA region originally present between HindIII and NcoI was absent.

The unique BspM1 site in ptrc1 (upstream of the −35 region of the trc promoter) was used to insert a cassette containing a chloramphenicol resistance gene (CAT) flanked by loxP sites. Linear DNA was obtained from pTrc1 digested with BspM1, gel-purified using a QIAquick gel extraction kit (QIAGEN), filled in with T4 DNA polymerase, and ligated to a loxP-Cat-loxP cassette. The loxP-Cat-loxP cassette was obtained from the plasmid pLoxCat1, see SEQ ID NO:6, by digestion with Stu1 and BamH1. pLoxCat1 is similar to pLoxCat2 (Palmeros et al, supra]. The ligation mixture was transformed into *E. coli* TOP-10 (Invitrogen) and selection was performed on Luria-agar plates containing 50 mg/L of carbenicillin and 20 mg/L of chloramphenicol. Plasmid was obtained and restriction enzyme analysis performed. Two plasmids, containing loxP-Cat-loxP-Trc with the loxP-Cat-loxP cassette in the same and in the opposite orientation relative to the trc promoter, were designated pTrCm41 and pTrCm42, respectively.

Construction of a trc Promoter Replacement Template for galP (pR6KqalP).

A DNA cassette containing the trc promoter and lac operator with an upstream loxP-CAT-loxP cassette was PCR amplified from pTrCm42 using the primer pair SEQ ID NO:7 and SEQ ID NO:8. The primer pair incorporates 40 bp of homology to the galP upstream region to each end of the PCR product. PCR parameters were 95° C. for 1 min; 55° C. for 1 min; 72° C. for 2 min, 30 cycles using Taq polymerase (Roche). The product was subcloned into Echo pUni/His5 R6K (Invitrogen) to generate the plasmid pR6KgalP.

Construction of a trc Promoter Replacement Template for glk (pR6Kglk).

A DNA cassette containing the trc promoter and lac operator with an upstream loxP-CAT-loxP cassette was amplified from pTrCm42 by PCR using the primer pair SEQ ID NO:9 and SEQ ID NO:10. The primer pair SEQ ID NO:9 and SEQ ID NO:10 incorporates 39 (with a one base deletion) and 40 bp of homology, respectively, to the glk upstream region to each end of the PCR product. PCR parameters were 95° C. for 1 min; 55° C. for 1 min; 72° C. for 2 min, 30 cycles using Taq polymerase (Roche). The product was subcloned into Echo pUni/His5 R6K (Invitrogen) to generate the plasmid pR6Kglk.

Construction of an *E. coli* ΔptsHIcrr Strain (KLpts7).

A PTS minus derivative (ΔptsHIcrr) of *E. coli* strain KLndh81 was obtained by P1 vir transduction using a derivative of *E. coli* strain NF9 as donor (Flores et al., *Nature Biotechnology* 14, 620-623 (1996)). The transduction replaces the operon comprising ptsH, ptsI and crr with a kanamycin antibiotic resistance marker (Levy et al., *Gene* 86, 27-33 (1990)) to give strain KLpts7. Plated on MacConkey (lactose⁻) agar+1% glucose, KLpts7 exhibits a white colony phenotype.

Replacement of the Natural galP Promoter with the Synthetic trc Promoter (KLgalP-trc).

A PCR amplification product comprising a loxP-Cat-loxP-Trc cassette and incorporating 40 bp of homology to the galP upstream region [for reference, see GenBank, Accession # U00096] to each end was generated using rTth RNA polymerase (Perkin Elmer), pR6KgalP as the template and the primer pair SEQ ID NO:7 and SEQ ID NO:8. The PCR amplified integration cassette was transformed into electrocompetent KLpts7 cells containing pKD46 for integration using the lambda Red system as described in Datsenko and Wanner, supra. Selection was performed on LB plates containing 10 mg/L chloramphenicol. Successful integration of this cassette replaces the region 38 to 181 bp upstream of the galP ATG start codon (for reference, see GenBank, Accession # U00096) with a loxP-Cat-loxP-Trc cassette (SEQ ID NO:11) to provide strain KLpts::galP-trc. Integration was confirmed by PCR analysis using the primer pair SEQ ID NO:7 and SEQ ID NO:8 (amplifying the integration site to give a 1.4 kb product) and the primer pair SEQ ID NO:12 and SEQ ID NO:13 (amplifying the integration site, including upstream and downstream regions, to give a 2.1 kb product). PCR parameters were 95° C. for 1 min; 55° C. for 1 min; 72° C. for 2 min, 30 cycles using Taq polymerase or rTth polymerase. KLpts::galP-trc, plated on MacConkey (lactose⁻) agar+1% glucose, exhibits a light red colony phenotype. The chloramphenicol marker was removed as described by Palmeros et al., supra. The removal was confirmed by PCR analysis using the primer pair SEQ ID NO:12 and SEQ ID NO:13 (to give a 1.1 kb product) and the resulting strain was designated KLgalP-trc.

Replacement of the Natural glk Promoter with the Synthetic trc Promoter (KLGG)

A PCR amplification product comprising a loxP-Cat-loxP-Trc cassette and incorporating approximately 40 bp of homology to the glk upstream region [for reference, see GenBank, Accession # U00096] to each end was generated using rTth RNA polymerase (Perkin Elmer), pR6Kglk as the template, and the primer pair SEQ ID NO:9 and SEQ ID NO:10. The PCR amplified integration cassette was transformed into electro-competent KLgalP-trc cells containing pKD46 for integration using the lambda Red system as described above. Selection was performed on LB plates containing 10 mg/L chloramphenicol. Successful integration of this cassette replaces the region 40 to 137 bp upstream of the glk ATG start codon (for reference, see GenBank, Accession # U00096) with a loxP-Cat-loxP-Trc cassette (SEQ ID NO:11). Integration was confirmed by PCR analysis using the primer pair SEQ ID NO:14 and SEQ ID NO:15 (amplifying the integration site, including upstream and downstream regions, to give a 2.4 kb product). Plated onto MacConkey (lactose⁻) agar+ 1% glucose, colonies exhibit a deep red color, indicating an increase in the conversion of glucose to acid compared to the parent (KLgalP-trc). The chloramphenicol marker was removed as described above and subsequent PCR analysis (using the primer pair SEQ ID NO:14 and SEQ ID NO:15 to give a 1.3 kb product) gave the strain KLGG.

Deletion of the arcA Gene, Encoding a Global Regulator (KLGG ΔarcA).

A P1 lysate of the MG1655 ΔarcA::Cm strain was prepared and used to move the mutation to strain KLGG. A resulting chloramphenicol resistant clone, KLGG ΔarcA::Cm, was checked by genomic PCR to insure that the mutation was present. The chloramphenicol resistance marker was removed using the FLP recombinase (Datsenko and Wanner, supra) and this strain has been designated KLGG ΔarcA.

Deletion of the edd Gene, Encoding 6-Phosphogluconate Dehydrase Gene (KLGG ΔarcA Δedd, also Designated FMP)

An edd deletion [for reference, see GenBank, Accession # U00096] was obtained by replacing 1.7 kb of the coding region with a loxP-cat-loxP cassette from pLoxCat2. A replacement cassette was amplified with the primer pair SEQ ID NO:16 and SEQ ID NO:17. The primer SEQ ID NO:16 contains 80 bp of homology to the 5' end of edd and 18 bp of homology to the template pLoxCat2. The primer SEQ ID NO:17 contains 78 bp of homology to the 3' end of edd and 19 bp of homology to pLoxCat2. The PCR product was gel-purified and electroporated into KLGG ΔarcA/pKD46 competent cells. Recombinant strains were selected on LB plates with 12.5 mg/L chloramphenicol. The deletion of the edd gene was confirmed by PCR using primer pair SEQ ID NO:18 and SEQ ID NO:19. The wild-type strain gives a 2.2 kb PCR product while the recombinant gives a characteristic 1.6 kb PCR product. This strain has been designated KLGG ΔarcA Δedd::cat. The chloramphenicol marker was removed using the Cre recombinase (Palmeros et al., supra) and this strain has been designated KLGG ΔarcA Δedd or, alternatively, FMP.

Selection and Characterization of an FMP Strain Exhibiting an Enhanced Rate of Glucose Consumption Invariably, cells comprising ΔptsHIcrr, the trc promoter replacement of the natural galP promoter, and the trc promoter replacement of the natural glk promoter (all three modifications as described in Example 4) initially exhibited slow growth. Also invariably, a subsequent selection (as described below) lead to a faster growing derivative. Glucokinase activity, assayed from cell-free extracts, was typically three-fold higher for the faster growing derivative as compared to the slower growing parent.

*E. coli* strain FMP, transformed with plasmid pSYCO103, was grown in a 14 L fermenter essentially as described in Example 2. Vials for storage at −80° C. (15% glycerol stocks) were made over the course of the fermentation. A LB plate was streaked from the aliquot taken at 33 hrs ($OD_{550}$ was 30.7 AU) and single colonies were recovered and designated "selected FMP/pSYCO103". Single colonies were similarly obtained from strain FMP containing no plasmid and designated "selected FMP".

The galP and glk genes, including the introduced trc promoter region, were PCR amplified from two colonies of "selected FMP/pSYCO103" and one colony of "selected FMP" using the primer pair SEQ ID NO:12/SEQ ID NO:13 and the primer pair SEQ ID NO:14/SEQ ID NO:15, respectively. Sequence analysis on these three samples was performed using the same primers. In each case, the galP gene and promoter region remained unchanged from the parent strain while the glk gene and promoter region contained an identical, single base pair change when compared the parent strain. The two isolates of "selected FMP/pSYCO103" and one isolate of "selected FMP" contained the sequence identified as SEQ ID NO:20 in the −35 to −10 region of trc promoter controlling glk expression compared to the corresponding parent sequence SEQ ID NO:21. The strain originating from "selected FMP" from which galP and glk sequence was obtained was designated strain FMP'::Km.

EXAMPLE 5

Comparative Examples of Glucose to 1,3-Propanediol Fermentations Using Strains FMP/pSYCO103 and FMP'::Km/pSYCO103

Strains FMP and FMP'::Km were transformed with the plasmid pSYCO103. Production of 1,3-propanediol was determined in 14 L fermenters as described in General Methods with the following differences in the control parameters or the fermenter. A thawed frozen vial of FMP/pSYCO103 was transferred to 500 mL 2YT with 50 mg/L spectinomycin to prepare the pre-culture. The dO set-point was 15%. Vitamin $B_{12}$ was added to the fermenter in 16 mg boluses at 30, 43, and 51 h.

A thawed frozen vial of FMP'::Km/pSYCO103 was transferred to 500 mL SBG1% with 50 mg/L spectinomycin to prepare the pre-culture. Vitamin $B_{12}$ was added to the fermenter in 16 mg boluses at 21, 40 and 40.5 h.

FIG. 1 shows the production of 1,3-propanediol by FMP'::Km/pSYCO103 is faster than by FMP'/pSYCO103.

EXAMPLE 6

Engineering Altered Expression of Glyceraldehyde-3-Phosphate Dehydrogenase (gapA) in E. coli Strains for Production of 1,3 Propanediol from Glucose Decreasing GapA Expression by Altering the Start Condon The level of glyceraldehyde-3-phosphate dehydrogenase, GapA, was decreased by replacing the ATG start codon of the gapA gene with a GTG or TTG start codon.

The E. coli gapA gene plus upstream and downstream flanking sequence was amplified by PCR from E. coli strain MG1655 using primer pair SEQ ID NO:22 and SEQ ID NO:23. The PCR product was cloned directly from the PCR reaction into pCR-BluntII-TOPO (Invitrogen) to form pDT50. The plasmids pDT50 and pLitmus 28 (New England Biolabs, Inc.) were digested with SphI and BamH I and the gapA gene fragment and vector, respectively, were gel-purified and ligated. The resulting plasmid, pDT51, was transformed into E. coli TOP10 (Invitrogen).

The gapA mutant plasmids were constructed using the Stratagene QuickChange 1-Day Site-Directed Mutagenesis Method (Stratagene, La Jolla, Calif.). The template plasmid, pDT51, was mixed with either the primer pair SEQ ID NO:24 and SEQ ID NO:25 to create the GTG mutation or the primer pair SEQ ID NO:26 and SEQ ID NO:27 to create the TTG mutation. After the PCR amplification, the reactions were digested with DpnI to remove the template plasmid and leave only the amplified plasmids. The plasmids were then transformed into E. coli TOP10 (Invitrogen).

The gapA-GTG and gapA-TTG constructs were PCR amplified using primer pair SEQ ID NO:22 and SEQ ID NO:23. The PCR products were electroporated into the gapA knockout strain, KLP23A112. E. coli strain KLP23A112 was constructed by transducing KLP23 with a P1 phage lysate obtained from E. coli DS112 (E. coli Genetic Stock Center), a gapA deletion strain containing a CmR marker. Recombinants were selected for growth on LB plates without added glucose and sensitivity to chloramphenicol. Sequencing confirmed the successful integration of the GTG and TTG mutations. The mutated strains were named KLPAGTG and KLPATTG, respectively. Measurement of the GapA activities in the KLPAGTG and KLPATTG strains showed that the GapA levels were 4% and <1% of the control strain KLP23, respectively.

Strains KLP23, KLPAGTG, and KLPATTG were transformed with the plasmid pSYCO101 and tested for 1,3-propanediol production in TM2 medium containing 40 g/L glucose, 50 mg/L spectinomycin, and 1 mg/L vitamin $B_{12}$. The results are shown in Table 4.

TABLE 4

Representative shake flasks summary of the conversion of glucose to 1,3-propanediol using E. coli strains KLP 23/pSYCO101, KLP AGTG/pSYCO101, and KLPATTG/pSYCO101

| Strain | Glycerol (g/L) | 1,3-Propanediol (g/L) | Molar Yield (mol/mol) |
|---|---|---|---|
| KLP23 pSYCO101 | 5.8 | 10.7 | 0.87 |
| KLPAGTG pSYCO101 | 0.7 | 1.3 | 0.11 |
| KLPATTG pSYCO101 | 0.2 | 0.4 | 0.04 |

Altering GapA Expression by Replacing the Promoter

Replacement of the natural gapA promoter with the synthetic short 1.5 GI promoter (SEQ ID NO:28) was made by replacing 225 bp of upstream gapA sequence [for reference, see GenBank, Accession # U00096) with FRT-CmR-FRT and an engineered promoter. The replacement cassette was amplified by PCR with the primer pair SEQ ID NO:29 and SEQ ID NO:30 using pKD3 as a template. The primer SEQ ID NO:29 contains 39 bp of homology to gapA including the ATG start, contains the short 1.5 GI promoter and contains 20 bp of homology to template pKD3. Primer SEQ ID NO:30 contains 59 bp of homology to upstream gapA sequence and 21 bp of homology to pKD3. The PCR products were gel-purified and electroporated into MG1655/pKD46 competent cells to give MG1655 1.5gapA::Cm. Recombinant strains were selected on LB plates with 12.5 mg/L chloramphenicol. Successful integration of the cassette replaces the region 34-258 bp upstream of the gapA ATG start codon with a FRT-CmR-FRT-short 1.5 GI promoter cassette. A P1 phage lysate was prepared and used to move the mutation to FMP'::Km. This strain was designated FMP'::Km 1.5gapA::Cm.

The short 1.5 GI gapA promoter in MG1655 1.5gapA::Cm was replaced with the short 1.20 GI promoter (SEQ ID NO:31) or the short 1.6 GI promoter (SEQ ID NO:32). To create the 1.20 gapA strain, a replacement cassette was PCR amplified with primer pair SEQ ID NO:33 and SEQ ID NO:34 using genomic DNA from MG1655 1.5gapA::Cm as template. Primer SEQ ID NO:33 contains 24 bp of homology to the gapA upstream region. Primer SEQ ID NO:34 contains homology to the gapA upstream region in MG1655 1.5gapA::Cm and contains the short 1.20 GI promoter. To create the 1.6gapA strain, a replacement cassette was PCR amplified with primer pair SEQ ID NO:33 and SEQ ID NO:35 using genomic DNA from MG1655 1.5gapA::Cm as template. The primer SEQ ID NO:35 contains homology to the gapA upstream region in MG1655 1.5gapA::Cm and contains the short 1.6 GI promoter. The short 1.20 GI promoter replacement cassette and the short 1.6 GI promoter replacement cassette were used to replace the natural gapA promoter of MG1655 as described above to give strains MG1655 1.20gapA::Cm and MG1655 1.6gapA::Cm, respectively. MG1655 1.20gapA::Cm and MG1655 1.6gapA::Cm were used to replace the natural gapA promoter of strain FMP'::Km (using P1 transduction as described above) to give strains FMP'::Km 1.20gapA::Cm and FMP'::Km 1.6gapA::Cm, respectively.

Glyceraldehyde-3-phosphate dehydrogenase activities were determined using cell-free extracts prepared from the strains FMP'::Km 1.20gapA::Cm, FMP'::Km 1.5gapA::Cm, FMP'::Km 1.6gapA::Cm and FMP'::Km as control. The values obtained, compared to that of control, were 10%, 25% and 140% for strains FMP'::Km 1.20gapA::Cm, FMP'::Km 1.5gapA::Cm, FMP'::Km 1.6gapA::Cm, respectively.

The strains containing the GI promoter replacements were transformed with the plasmid pSYCO106 and compared to the parent strain for 1,3-propanediol production in TM2 medium containing 20 g/L glucose, 50 mg/L spectinomycin, and 1 mg/L vitamin $B_{12}$. The results are shown in Table 5.

TABLE 5

Representative shake flasks summary of FMP'::Km GI promoter gapA strains transformed with the plasmid pSYCO106

| Strain | Glycerol (g/L) | 1,3-Propanediol (g/L) | Molar yield (mol/mol) |
| --- | --- | --- | --- |
| FMP'::Km/pSYCO106 | 1.8 | 6.8 | 1.07 |
| FMP'::Km 1.6gapA/pSYCO106 | 4.1 | 3.3 | 0.92 |
| FMP'::Km 1.5gapA/pSYCO106 | 6.6 | 3.6 | 1.21 |
| FMP'::Km 1.20 gapA/pSYCO106 | 7.6 | 2.8 | 1.26 |

EXAMPLE 7

Removing the Markers from FMP'::Km 1.5gapA::Cm

The chloramphenicol marker was removed from strain FMP'::Km 1.5gapA::Cm (as described in the General Methods section) to give strains FMP'::Km 1.5gapA.

The kanamycin marker introduced into FMP'::Km 1.5gapA as a consequence of making KLndh81 PTS minus (ΔptsHIcrr) was replaced with a removable FRT-Cm-FRT cassette by P1 transduction from MG1655 ΔptsHIcrr::Cm. A ptsHIcrr deletion in MG1655 was made with a replacement cassette amplified with primer pair SEQ ID NO:54 and SEQ ID NO:55 using pKD3 as template. The primer SEQ ID NO:54 contains 78 bp of homology to the remaining region of ptsH left in the chromosome of strain FMP'::Km 1.5gapA and 20 bp of homology to pKD3. The primer SEQ ID NO:55 contains 77 bp of homology to the remaining region of crr in strain FMP'::Km 1.5gapA and 20 bp of homology to pKD3. The PCR products were gel-purified and electroporated into MG1655/pKD46 competent cells. Recombinant strains were selected on LB plates with chloramphenicol 12.5 mg/L. PCR analysis confirmed the integration of the cassette. Plated on MacConkey (lactose⁻) agar+1% glucose, MG1655 ΔptsHIcrr::Cm exhibits a white colony phenotype. A P1 phage lysate was prepared and the Cm marker transduced into FMP'::Km 1.5gapA. Recombinant strains were selected on chloramphenicol and PCR analysis confirmed successful integration of the cassette. The chloramphenicol marker was removed using the Flp recombinase and sequencing (using primer SEQ ID NO:56) confirmed the removal of the chloramphenicol marker. The resulting strain was designated FMP' 1.5 gapA.

EXAMPLE 8

Demonstrating High Yield of 1,3-Propanediol from Glucose Using E. coli Strain FMP' 1.5gapA/pSYCO106

Strain FMP' 1.5gapA was transformed with the plasmid pSYCO106. Production of 1,3-propanediol and glycerol was determined in 14 L fermenters as described in General Methods with the following differences in the control parameters for the fermenter. A thawed frozen vial of FMP' 1.5gap/pSYCO106 was transferred to 500 mL SBG1% with 50 mg/L spectinomycin to prepare the pre-culture. Vitamin $B_{12}$ was added to the fermenter in 16 mg boluses prior to inoculation and at 28 hrs. Final 1,3-propanediol concentration was 129 g/L and the mass yield was 40.2%.

EXAMPLE 9

Engineering a Methylglyoxal Synthase (mgsA) Mutant in E. coli

The mgsA deletions [for reference, see GenBank, Accession # U00096] were made by replacing 0.4 kb of the coding region with the FRT-Kan-FRT cassette of pKD4. A replacement cassette was PCR amplified with the primer pair SEQ ID NO:36 and SEQ ID NO:37 using pKD4 as the template. The primer SEQ ID NO:36 contains 40 bp of homology to the 5' end of mgsA and 20 bp of homology to the template DNA, pKD4. The primer SEQ ID NO:37 contains 40 bp of homology to the 3' end of mgsA and 20 bp of homology to pKD4. The PCR product was gel-purified and electroporated into MG1655/pKD46 competent cells. Recombinant strains were selected on LB plates with 12.5 mg/L of kanamycin. The deletion of the mgsA gene was confirmed by PCR, using the primer pair SEQ ID NO:38 and SEQ ID NO:39. The wild-type strain gives a 1.3 kb PCR product while the recombinant strain gives a characteristic 2.4 kb PCR product. This strain has been designated MG1655 ΔmgsA::kan. Once the mgsA mutant was obtained in MG1655, a P1 phage lysate was prepared and used to move the mutation into FMP' 1.5gapA (Example 8). The kanamycin resistance marker was removed using the FLP recombinase (Datsenko and Wanner, supra) and this strain has been designated FMP' 1.5gapA ΔmgsA.

FMP' 1.5gapA ΔmgsA and its parent were transformed with the plasmid pSYCO106 to give FMP' 1.5gapA ΔmgsA/pSYCO106 and FMP' 1.5gapA/pSYCO106, respectively.

The strains were tested for 1,3-propanediol production in TM2 medium containing 20 g/L glucose, 50 mg/L spectinomycin, and 1 mg/L vitamin $B_{12}$. The results are shown in Table 6.

TABLE 6

Representative shake flasks summary of FMP' 1.5gapA/pSYCO106 and FMP' 1.5gapA ΔmgsA/pSYCO106 strains

| Strain | Glycerol (g/L) | 1,3-Propanediol (g/L) | Molar yield (mol/mol) |
| --- | --- | --- | --- |
| FMP'1.5gapA/pSYCO106 | 6.6 | 3.6 | 1.21 |
| FMP'1.5gapA ΔmgsA/pSYCO106 | 8.3 | 2.4 | 1.26 |

EXAMPLE 10

Fermentation of Glucose to 1,3-Propanediol Using E. coli Strain FMP' 1.5gapA ΔmgsA/pSYCO106

Strain FMP' 1.5gapA ΔmgsA was transformed with the plasmid pSYCO106. Production of 1,3-propanediol (and glycerol) was determined in 14 L fermenters as described in General Methods with the following differences in control parameters for fermenters. A single colony from a fresh plate (LA with 50 mg/L spectinomycin) of FMP' 1.5gapA ΔmgsA/pSYCO106 was transferred to 30 mL LB with 100 mg/L spectinomycin in a 250 mL flask to prepare the pre-culture. After incubation at 34° C. and 300 rpm to an $OD_{550}$ of 1 AU, 10.8 mL of the culture was transferred to the fermenter. The fermenter was run with glucose limitation during much of the run. Vitamin $B_{12}$ was added to the fermenter in 16 mg boluses prior to inoculation, at 28 hrs and at 38 hrs. Final 1,3-propanediol concentration was 130 g/L and the mass yield was 47.5%. A run with glucose maintained in excess (0-20 g/L) gave 141 g/L 1,3-propanediol and a mass yield of 43.6%.

EXAMPLE 11

Construction of an *E. coli* Strain with an Engineered Promoter for Phosphoenolpyruvate Carboxylase (ppc) by Linear DNA Transformation Replacement of the natural ppc promoter with the synthetic short 1.6 GI promoter was made by replacing 59 bp of the upstream ppc sequence cassette containing FRT-CmR-FRT and an engineered promoter. The PCR product was amplified with the primer pair SEQ ID NO:40 and SEQ ID NO:41 using pKD3 as the template. Primer SEQ ID NO:40 contains 80 bp of homology to upstream ppc sequence and 20 bp of homology to template pKD3. Primer SEQ ID NO:41 contains 39 bp of homology to upstream ppc sequence, contains the short 1.6 GI promoter sequence and contains 20 bp of homology to pKD3. The PCR products were gel-purified and electroporated into MG1655/pKD46 competent cells. Recombinant strains were selected on LB plates with 12.5 mg/L chloramphenicol to give MG1655 1.6 ppc::Cm. Successful integration of the cassette replaces the region 90 to 148 bp upstream of the ppc ATG start [for reference, see GenBank, Accession # U00096] with a FRT-CmR-FRT-short 1.6 GI promoter cassette. Integration into the upstream ppc region was confirmed by primer pair SEQ ID NO:40 and SEQ ID NO:41. The wild-type strain gives a 0.2 kb PCR product while the recombinant strain gives a characteristic 1.2 kb PCR product. This PCR product was sequenced using primer SEQ ID NO:42, which indicated that the promoter replacement effectively occurred. A P1 phage lysate was prepared and used to move the mutation to strain FMP'1.5gap ΔmgsA. This strain was designated FMP'1.5gap Δmgs 1.6 ppc::Cm. The chloramphenicol-resistance marker was removed using the FLP recombinase (Datsenko and Wanner, supra), and the resulting strain was electrotransformed with plasmid pSYCO106 to give FMP'1.5gap Δmgs 1.6 ppc/pSYCO106.

Shake flask cultures were used to assess the conversion of glucose to 1,3-propanediol in *E. coli* strains FMP'1.5gap Δmgs/pSYCO106 and FMP'1.5gap Δmgs 1.6 ppc/pSYCO106. The strains, grown in LB medium containing 50 mg/L spectinomycin for 10 hrs, were used to inoculated (200 μL) into 250 mL-baffled Erlenmeyer flasks containing 10 mL TM2 medium, 20 g/L glucose, 50 mg/L spectinomycin, and 2 mg/L vitamin $B_{12}$. The flasks were incubated at 300 rpm and 34° C. Representative results are given in Table 7. Both an increase in the molar yield and a decrease of acetate production were observed with the addition of the 1.6 ppc mutation to the parent strain.

TABLE 7

| | Shake Flasks for Conversion of Glucose to 1,3-Propanediol (1,3-PD) | | | |
|---|---|---|---|---|
| Strain | Glycerol produced (g/L) | 1,3-Propanediol produced (g/L) | Acetate produced (g/L) | Molar Yield |
| FMP'1.5gap ΔmgsA/pSYCO106 | 8.24 | 2.19 | 1.78 | 1.25 |
| FMP'1.5gap Δmgs 1.6ppc/pSYCO106 | 7.5 | 3.34 | 0.34 | 1.32 |

Phosphoenolpyruvate carboxylase (Ppc) activity was measured from cell-free extracts obtained from the shake flasks described immediately above. Aliquots of cells were harvested in mid-log phase, broken by two passages through a French press cell, centrifuged for 15 min at 14,000 rpm, and ultracentrifuged 1 hr at 50,000 rpm. The supernatant was removed and used as a source of proteins. Specific activities of PPC are reported in Table 8 below. The replacement of the natural ppc promoter with the short 1.6 GI promoter increased the Ppc enzyme activity three-fold.

TABLE 8

| PPC Enzyme Specific Activity | |
|---|---|
| Strain | Phosphoenolpyruvate carboxylase specific activity (U/mg protein) |
| FMP'1.5gap ΔmgsA, pSYCO106 | 0.28 |
| FMP'1.5gap Δmgs 1.6ppc, pSYCO106 | 0.86 |

EXAMPLE 11A

Fermentation of Glucose to 1,3-Propanediol Using *E. coli* Strain FMP' 1.5gapA ΔmgsA/pSYCO106

Production of 1,3-propanediol by FMP' 1.5gapA ΔmgsA 1.6 ppc/pSYCO106 was determined in 14 L fermenters as described in General Methods with the following differences in control parameters for fermenters. A single colony from a fresh plate (LA with 50 mg/L spectinomycin) of FMP' 1.5gapA ΔmgsA 1.6 ppc/pSYCO106 was transferred to 30 mL LB with 100 mg/L spectinomycin in a 250 mL flask to prepare the pre-culture. After incubation at 34° C. and 300 rpm to an OD550 of 1 AU, 10.8 mL of the culture was transferred to the fermenter. Vitamin $B_{12}$ was added to the fermenter in 16 mg boluses prior to inoculation, at 28 hrs, and at 38 hrs. Final 1,3-propanediol concentration was 135.3 g/L and the mass yield was 46.1%.

EXAMPLE 12

Construction of *E. coli* Strain with an Engineered Promoter for yciKlbtuR by Linear DNA Transformation The genes yciK and btuR are present within a single operon in *E. coli*. Replacement of the natural yciK-btuR promoter with the synthetic short 1.6 GI promoter was made by inserting a 1.3 kb cassette, upstream of yciK-btuR. The replacement cassette, containing FRT-CmR-FRT and an engineered promoter, was amplified by PCR with the primer pair SEQ ID NO:43 and SEQ ID NO:44 using pKD13 as the template. Primer SEQ ID NO:43 contains 70 bp of homology to upstream yciK-btuR sequence and 20 bp of homology to template pKD13. Primer SEQ ID NO:44 contains 30 bp of homology to upstream yciK-btuR sequence, contains the short 1.6 GI promoter sequence and contains 20 bp of homology to pKD13. The PCR products were gel-purified and electroporated into MG1655/pKD46 competent cells. Recombinant strains were selected on LB plates with 25.0 mg/L kanamycin to give MG1655 1.6yciK-btuR::Km. Successful integration of the cassette results in an insertion between bp 27 and bp 28 upstream of the yciK ATG start codon [for reference, see GenBank, Accession # U00096] with a FRT-CmR-FRT-short 1.6 GI promoter cassette. Integration into the upstream yciKlbtuR region was confirmed by primer pair SEQ ID NO:45 and SEQ ID NO:46. The wild-type strain gives a 1.4 kb PCR product while the recombinant strain gives a characteristic 2.8 kb PCR product. A P1 phage lysate was prepared and used to move the mutation to a derivative of strain FMP'1.5gap Δmgs 1.6 ppc named Triple. After removing the antibiotic, strain Triple 1.6btuR was obtained.

EXAMPLE 12A

Fermentation of Glucose to 1,3-Propanediol Using
E. coli Strain Triple 1.6btuR/pSYCO109

Strain Triple 1.6btuR was transformed with pSYCO109. Production of 1,3-propanediol by Triple 1.6btuR/pSYCO109 was determined in 14 L fermenters as described in General Methods with the following differences in control parameters for fermentation. A single colony from a fresh plate (LA with 50 mg/L spectinomycin) of Triple 1.6btuR/pSYCO109 was transferred to 30 mL LB with 100 mg/L spectinomycin in a 250 mL flask to prepare the pre-culture. After incubation at 34° C. and 300 rpm to an OD550 of 1 AU, 10.8 mL of the culture was transferred to the fermenter. Vitamin $B_{12}$ was added to the fermenter in 8 mg boluses prior to inoculation, at 28 hrs, and at 38 hrs. Final 1,3-propanediol concentration was 123 g/L and the mass yield was 45.7%.

EXAMPLE 13

Construction of E. coli Strain with an Engineered Promoter for yqhD by Linear DNA Transformation Replacement of the natural yqhD (alcohol dehydrogenase) promoter with the synthetic short 1.6 GI promoter was made by replacing 967 bp of upstream yqhD sequence including the yqhC gene with a cassette containing FRT-CmR-FRT and an engineered promoter. The PCR product was amplified with the primer pair SEQ ID NO:47 and SEQ ID NO:48 using pKD3 as the template. Primer SEQ ID NO:47 contains 78 bp of homology to upstream yqhD sequence and 20 bp of homology to template pKD3. Primer SEQ ID NO:48 incorporates 41 bp of homology (with a 1 bp deletion) to upstream yqhD sequence, 40 bp of homology to the short 1.6 GI promoter sequence, and 19 bp of homology to pKD3. The PCR products were gel-purified and electroporated into MG1655/pKD46 competent cells. Recombinant strains were selected on LB plates with 12.5 mg/L chloramphenicol to give MG1655 1.6yqhD::Cm. Successful integration of the cassette replaces the region 50-1016 bp upstream of the yqhD ATG start [for reference, see GenBank, Accession # U00096] with a FRT-CmR-FRT-short 1.6 GI promoter cassette. Integration into the upstream yqhD region was confirmed by sequencing with primer SEQ ID NO:49 and indicated that the promoter replacement effectively occurred. A P1 phage lysate was prepared and used to move the mutation into strain Triple 1.6btuR. After removing the antibiotic (as described above), strain Triple 1.6btuR 1.6yqhD was obtained.

EXAMPLE 13A

Fermentation of Glucose to 1,3-Propanediol Using
E. coli Strain Triple 1.6btuR 1.6yqhD/pSYCO109

Strain Triple 1.6btuR 1.6yqhD was transformed with pSYCO109. Production of 1,3-propanediol by Triple 1.6btuR 1.6yqhD/pSYCO109 was determined in 14 L fermenters as described in General Methods with the following differences in control parameters for fermentation. A single colony from a fresh plate (LA with 50 mg/L spectinomycin) of Triple 1.6btuR 1.6yqhD/pSYCO109 was transferred to 30 mL LB with 100 mg/L spectinomycin in a 250 mL flask to prepare the pre-culture. After incubation at 34° C. and 300 rpm to an OD550 of 1 AU, 10.8 mL of the culture was transferred to the fermenter. Vitamin $B_{12}$ was added to the fermenter in a single 16 mg bolus at 20.6 hrs elapsed fermentation time. Final 1,3-propanediol concentration was 113.3 g/L and the mass yield was 48.8%.

EXAMPLE 14

Construction of an E. coli Strain with a Deletion Mutation in Acetate Kinase (ack) and Phosphotransacetylase (pta) by Linear DNA Transformation The pta-ackA deletion [for reference, see GenBank, Accession # U00096] was made by replacing 3.3 kb of the coding region with the FRT-CmR-FRT cassette of pKD3. The replacement cassette was amplified with the primer pair SEQ ID NO:50 and SEQ ID NO:51 using pKD3 as the template. The primer SEQ ID NO:50 contains 80 bp of homology to the 5' end of pta and 20 bp of homology to the template DNA, pKD3. The primer SEQ ID NO:51 contains 80 bp of homology to the 3' end of ackA and 20 bp of homology to pKD3. The PCR products were gel-purified and electroporated into MG1655/pKD46 competent cells. Recombinant strains were selected on LB plates with 12.5 mg/L of chloramphenicol to give strain MG1655 ΔackA-pta::Cm. The deletion of the pta-ackA genes was confirmed by PCR, using the primer pair SEQ ID NO:52 and SEQ ID NO:53. The wild-type strain gives a 3.8 kb PCR product while the recombinant strain gives a characteristic 1.6 kb PCR product. A P1 phage lysate was prepared and used to pass the mutation to strain Triple 1.6btuR 1.6yqhD to form strain Triple 1.6btuR 1.6yqhD ΔackA-pta::Cm. The chloramphenicol resistance marker was removed using the FLP recombinase (Datsenko and Wanner, supra) to give Triple 1.6btuR 1.6yqhD ΔackA-pta (renamed TripleTriple (TT)). The Triple 1.6btuR 1.6yqhD and TT strains were electrotransformed with plasmid pSYCO109.

EXAMPLE 15

Measurement of Phosphotransacetylase (Pta)
Enzyme Activity in Strain Triple Triple/pSYCO109
Compared to Strain Triple 1.6btuR
1.6yqhD/pSYCO109

Fermentations with TT/pSYCO109 and Triple 1.6btuR 1.6yqhD/pSYCO109 were carried out in 14L fermenters as described in the General Methods with the following differences in control parameters for fermentation. A typical fermentation with Triple 1.6btuR 1.6yqhD/pSYCO106 was described in Example 13A.

A pre-culture of TT/pSYCO109 was grown in 30 mL LB with 100 mg/L spectinomycin in a 250 mL flask to an OD550 of approximately 1 AU. A seed fermenter prepared as described was inoculated with 10.8 mL of that culture. After 30.5 hrs of fermentation time, 1.2 L of the culture was transferred to a production fermenter. This fermenter received a single 16 mg bolus of vitamin $B_{12}$ 1 hr after inoculation. The final concentration of 1,3-propanediol in a typical fermentation was 114 g/L and the yield was 48%.

Samples from a typical Triple 1.6btuR 1.6yghD/pSYCO109 fermentation were analyzed for Pta enzyme activity. A specific activity of 0.4 U/mg protein was obtained. Samples assayed from a typical TT/pSYCO109 fermentation showed no detectable Pta enzyme activity.

EXAMPLE 16

Improved Stability of Molar Yields in Strain TT/pSYCO109 Compared to Triple 1.6btuR 1.6yqhD/pSYCO109

Duplicate shake flasks cultures were grown with strains Triple btuR 1.6 yqhD, pSYCO109, and TT pSYCO109. After incubating one colony for 10 hr in LB+50 mg/L spectinomycin, 100 mL of culture were transferred in 30 mL TM2 medium with 2% glucose and with or without 50 ppm spectinomycin (day 1). In order to study the stability of the yield, a 100 mL volume of the day 1 cultures was transferred after 24 hr to a fresh volume of 30 mL TM2 media containing 2% glucose with or without 50 ppm spectinomycin. This was repeated 4 times. The molar yield was calculated as in Example 2 at the end of each 24 hr period and results are given below in Table 9. The ackA-pta deletion stabilizes the molar yield, therefore improving 1,3-propanediol production.

SEQ ID NO:58 contains 80 bp of homology to the 3' end of aldA and 20 bp of homology to pKD3. The PCR products were gel-purified and electroporated into MG1655/pKD46 competent cells. Recombinant strains were selected on LB plates with 12.5 mg/L of chloramphenicol. The deletion of the aldA gene was confirmed by PCR, using the primer pair SEQ ID NO:59 and SEQ ID NO:60. The wild-type strain gives a 2.0 kb PCR product while the recombinant strain gives a characteristic 1.8 kb PCR product. A P1 lysate of that strain was prepared and used to move the mutation to the strain TT to form the TT ΔaldA::Cm strain. The chloramphenicol resistance marker was removed using the FLP recombinase (Datsenko and Wanner, supra) to create TT aldA.

An aldB deletion [for reference, see GenBank, Accession # U00096] was made by replacing 1.5 kb of the coding region with the FRT-CmR-FRT cassette of the pKD3. A replacement cassette was amplified with the primer pair SEQ ID NO:61 and SEQ ID NO:62 using pKD3 as the template. The primer SEQ ID NO:61 contains 80 bp of homology to the 5'-end of aldB and 20 bp of homology to pKD3. Primer SEQ ID NO:62 contains 80 bp of homology to the 3' end of aldB and 20 bp homology to pKD3. The PCR products were gel-purified and electroporated into MG1655/pKD46 competent cells. Recombinant strains were selected on LB plates with 12.5 mg/L of chloramphenicol. The deletion of the aldB gene was confirmed by PCR, using the primer pair SEQ ID NO:63 and SEQ ID NO:64. The wild-type strain gives a 1.5 kb PCR product while the recombinant strain gives a characteristic 1.1 kb PCR product. A P1 lysate was prepared and used to move the mutation to the TT strain to form the TT ΔaldB::Cm strain. A chloramphenicol-resistant clone was checked by genomic PCR with the primer pair SEQ ID NO:63 and SEQ ID NO:64 to insure that the mutation was present.

TABLE 9

| Strain | With (+) or Without (−) Spetinomycin | Molar Yield Day 1 | Molar Yield Day 2 | Molar Yield Day 3 | Molar Yield Day 4 | Molar Yield Day 5 |
| --- | --- | --- | --- | --- | --- | --- |
| Triple btuR, 1.6yqhD, pSYCO109 | + | 1.24 | 1.28 | 1.06 | 0.84 | 0.79 |
| TT, pSYCO109 | + | 1.15 | 1.22 | 1.24 | 1.24 | 1.07 |
| Triple btuR 1.6yqhD, pSYCO109 | − | 1.23 | 1.04 | 0.95 | 0.61 | 0.25 |
| TT, pSYCO109 | − | 1.23 | 1.22 | 1.23 | 1.13 | 1.11 |

EXAMPLE 17

Struction of *E. coli* Strain with Deletion Mutations in Aldehyde Dehydrogenases by Linear DNA Transformation An aldA deletion [for reference, see GenBank, Accession # U00096] was made by replacing 1.3 kb of the coding region with the FRT-CmR-FRT cassette of pKD3. The cassette was amplified with the primer pair SEQ ID NO:57 and SEQ ID NO:58 using pKD3 as the template. The primer SEQ ID NO:57 contains 80 bp of homology to the 5' end of aldA and 20 bp of homology to the template DNA, pKD3. The primer

EXAMPLE 17A

Production of Glycerol with Strain FMP' 1.5gap/pSYCO106

Strain FMP' 1.5gapA was transformed with the plasmid pSYCO106. Production of glycerol was determined in 14 L fermenters as described in General Methods with the following differences in control parameters for fermentation. A thawed frozen vial of FMP' 1.5gap/pSYCO106 was transferred to 500 mL SBG1% with 50 mg/L spectinomycin to prepare the pre-culture. No vitamin $B_{12}$ was added to the fermenter. A typical fermentation resulted in the production of 202 g/L glycerol with a molar yield of 115%.

EXAMPLE 17B

Production of Glycerol with Strain TT/pSYCO109

Production of glycerol was determined in 14 L fermenters as described in General Methods with the following differences in control parameters for fermentation. A single colony of TT/pSYCO109 on a LB plate with 50 mg/L spectinomycin was transferred to 30 mL LB with 100 mg/L spectinomycin in a 250 mL flask. When an OD550 of approximately 1 Au was reached, 10.8 mL of the culture was used to inoculate a fermenter prepared as described. No vitamin $B_{12}$ was added to the fermenter. A typical fermentation resulted in the production of 302 g/L glycerol with a molar yield of 137%.

---

What is claimed is:

1. A method for the bioproduction of 1,3-propanediol comprising contacting with a suitable carbon substrate under suitable conditions a *E. coli* strain comprising:
   a) a disrupted endogenous phosphoenolpyruvate-glucose phosphotransferase system comprising one or more of:
      i) a genetically disrupted endogenous ptsH gene preventing expression of active phosphocarrier protein;
      ii) a genetically disrupted endogenous ptsI gene preventing expression of active phosphoenolpyruvate-protein phosphotransferase; and
      iii) a genetically disrupted endogenous crr gene preventing expression of active glucose-specific IIA component;
   b) a genetically up regulated endogenous galP gene encoding active galactose-proton symporter, said up regulation resulting in an increased galactose-proton symporter activity, wherein the up regulation is produced by:
      i) introducing additional copies of said gene into said *E. coli* strain followed by integration; or
      ii) replacing a native regulatory sequence with a strong non-native promoter or altered native promoter;
   c) a genetically up regulated endogenous glk gene encoding active glucokinase, said up regulation resulting in an increased glucokinase activity, wherein the up regulation is produced by:
      i) introducing additional copies of said gene into said *E. coli* strain followed by integration; or
      ii) replacing a native regulatory sequence with a strong non-native promoter or altered native promoter; and
   d) a genetically down regulated endogenous gapA gene encoding active glyceraldehyde 3-phosphate dehydrogenase, said down regulation resulting in a reduced glyceraldehyde 3-phosphate dehydrogenase activity;
   whereby said *E. coil* strain is capable of bioconverting a suitable carbon source to 1,3-propanediol.

2. The method of claim 1, wherein the *E. coli* strain comprises a genetically disrupted endogenous arcA gene preventing expression of active aerobic respiration control protein.

3. The method of claim 1, wherein the *E. coil* strain further comprises:
   (i) glycerol-3-phosphate dehydrogenase;
   (ii) glycerol-3-phosphatase;
   (iii) glycerol dehydratase or diol dehydratase; and
   (iv) dehydratase reactivation factor.

4. The method of claim 2, wherein the *E. coil* strain further comprises:
   (i) glycerol-3-phosphate dehydrogenase;
   (ii) glycerol-3-phosphatase;
   (iii) glycerol dehydratase or diol dehydratase; and
   (iv) dehydratase reactivation factor.

* * * * *

SEQUENCE LISTING

<160> NUMBER OF SEQ ID NOS: 68

<210> SEQ ID NO 1
<211> LENGTH: 1137
<212> TYPE: DNA
<213> ORGANISM: Artificial Sequence
<220> FEATURE:
<223> OTHER INFORMATION: partial DNA sequence of plasmid pLoxCat27
      comprising the LoxP-Cat-LoxP cassette

<400> SEQUENCE: 1

```
ctcggatcca ctagtaacgg ccgccagtgt gctggaattc gcccttggcc gcataacttc      60
gtatagtata cattatacga agttatctag agttgcatgc ctgcaggtcc gaatttctgc     120
cattcatccg cttattatca cttattcagg cgtagcacca ggcgtttaag ggcaccaata     180
actgccttaa aaaattacg ccccgccctg ccactcatcg cagtactgtt gtaattcatt     240
aagcattctg ccgacatgga agccatcaca aacggcatga tgaacctgaa tcgccagcgg     300
catcagcacc ttgtcgcctt gcgtataata tttgcccatg gtgaaaacgg gggcgaagaa     360
gttgtccata ttggccacgt ttaaatcaaa actggtgaaa ctcacccagg gattggctga     420
gacgaaaaac atattctcaa taaaccctt agggaaatag gccaggtttt caccgtaaca     480
cgccacatct tgcgaatata tgtgtagaaa ctgccgaaa tcgtcgtggt attcactcca     540
gagcgatgaa aacgtttcag tttgctcatg gaaaacggtg taacaagggt gaacactatc     600
ccatatcacc agctcaccgt cttcattgc catacggaat tccggatgag cattcatcag     660
gcgggcaaga atgtgaataa aggccggata aaacttgtgc ttatttttct ttacggtctt     720
taaaaaggcc gtaatatcca gctgaacggt ctggttatag gtacattgag caactgactg     780
aaatgcctca aatgttctt tacgatgcca ttgggatata tcaacggtgg tatatccagt     840
gatttttttc tccatttag cttccttagc tcctgaaaat ctcgataact caaaaaatac     900
gcccggtagt gatcttattt cattatggtg aaagttggaa cctcttacgt gccgatcaac     960
gtctcatttt cgccaaaagt tggcccaggg cttcccggta tcaacaggga caccaggatt    1020
tatttattct gcgaagtgat cttccgtcac aggtatttat tcggactcta gataacttcg    1080
tatagtatac attatacgaa gttatgaagg gcgaattctg cagatatcca tcacact       1137
```

<210> SEQ ID NO 2
<211> LENGTH: 61
<212> TYPE: DNA
<213> ORGANISM: Artificial Sequence
<220> FEATURE:
<223> OTHER INFORMATION: Primer ArcA1

<400> SEQUENCE: 2

```
cacattctta tcgttgaaga cgagttggta acacgcaaca cgtgtaggct ggagctgctt      60
c                                                                      61
```

<210> SEQ ID NO 3

```
<211> LENGTH: 62
<212> TYPE: DNA
<213> ORGANISM: Artificial Sequence
<220> FEATURE:
<223> OTHER INFORMATION: Primer ArcA2

<400> SEQUENCE: 3
ttccagatca ccgcagaagc gataaccttc accgtgaatg gtcatatgaa tatcctcctt     60
ag                                                                    62

<210> SEQ ID NO 4
<211> LENGTH: 24
<212> TYPE: DNA
<213> ORGANISM: Artificial Sequence
<220> FEATURE:
<223> OTHER INFORMATION: Primer ArcA3

<400> SEQUENCE: 4
agttggtaac acgcaacacg caac                                            24

<210> SEQ ID NO 5
<211> LENGTH: 23
<212> TYPE: DNA
<213> ORGANISM: Artificial Sequence
<220> FEATURE:
<223> OTHER INFORMATION: Primer ArcA4

<400> SEQUENCE: 5
cgcagaagcg ataaccttca ccg                                             23

<210> SEQ ID NO 6
<211> LENGTH: 1320
<212> TYPE: DNA
<213> ORGANISM: Artificial Sequence
<220> FEATURE:
<223> OTHER INFORMATION: Partial sequence of pLoxCat1 comprising the
      lox-Cat-loxP cassette

<400> SEQUENCE: 6
aagcttaagg tgcacggccc acgtggccac tagtacttct cgaggtcgac ggtatcgata     60
agctggatcc ataacttcgt ataatgtatg ctatacgaag ttatctagag tccgaataaa    120
tacctgtgac ggaagatcac ttcgcagaat aaataaatcc tggtgtccct gttgataccg    180
ggaagccctg ggccaacttt tggcgaaaat gagacgttga tcggcacgta agaggttcca    240
actttcacca taatgaaata agatcactac cgggcgtatt ttttgagtta tcgagatttt    300
caggagctaa ggaagctaaa atggagaaaa aaatcactgg atataccacc gttgatatat    360
cccaatggca tcgtaaagaa catttgagg catttcagtc agttgctcaa tgtacctata    420
accagaccgt tcagctggat attacggcct ttttaaagac cgtaaagaaa aataagcaca    480
agttttatcc ggcctttatt cacattcttg cccgcctgat gaatgctcat ccggaattcc    540
gtatggcaat gaaagacggt gagctggtga tatgggatag tgttcaccct tgttacaccg    600
ttttccatga gcaaactgaa acgttttcat cgctctggag tgaataccac gacgatttcc    660
ggcagtttct acacatatat tcgcaagatg tggcgtgtta cggtgaaaac ctggcctatt    720
tccctaaagg gtttattgag aatatgtttt tcgtctcagc caatccctgg gtgagtttca    780
ccagttttga tttaaacgtg gccaatatgg acaacttctt cgccccgtt ttcaccatgg    840 gcaaatatta tacgcaaggc gacaaggtgc tgatgccgct ggcgattcag gttcatcatg    900
ccgtttgtga tggcttccat gtcggcagaa tgcttaatga attacaacag tactgcgatg    960
```

```
agtggcaggg cggggcgtaa tttttttaag gcagttattg gtgcccttaa acgcctggtg    1020
ctacgcctga ataagtgata ataagcggat gaatggcaga aattcggacc tgcaggcatg    1080
caactctaga taacttcgta taatgtatgc tatacgaagt tatgcggccg ccatatgcat    1140
cctaggccta ttaatattcc ggagtatacg tagccggcta acgttctagc atgcgaaatt    1200
taaagcgctg atatcgatcg cgcgcagatc tgtcatgatg atcattgcaa ttggatccat    1260
atatagggcc cggggttata attacctcag gtcgacgtcc catggccatt gaattcgtaa    1320

<210> SEQ ID NO 7
<211> LENGTH: 61
<212> TYPE: DNA
<213> ORGANISM: Artificial Sequence
<220> FEATURE:
<223> OTHER INFORMATION: Primer GalA

<400> SEQUENCE: 7
tcggttttca cagttgttac atttcttttc agtaaagtct ggatgcatat ggcggccgca    60
t                                                                    61

<210> SEQ ID NO 8
<211> LENGTH: 65
<212> TYPE: DNA
<213> ORGANISM: Artificial Sequence
<220> FEATURE:
<223> OTHER INFORMATION: Primer GalP2

<400> SEQUENCE: 8
catgatgccc tccaatatgg ttattttta ttgtgaatta gtctgtttcc tgtgtgaaat     60
tgtta                                                                65

<210> SEQ ID NO 9
<211> LENGTH: 60
<212> TYPE: DNA
<213> ORGANISM: Artificial Sequence
<220> FEATURE:
<223> OTHER INFORMATION: Primer GlkA

<400> SEQUENCE: 9
acttagtttg cccagcttgc aaaaggcatc gctgcaattg gatgcatatg gcggccgcat    60

<210> SEQ ID NO 10
<211> LENGTH: 67
<212> TYPE: DNA
<213> ORGANISM: Artificial Sequence
<220> FEATURE:
<223> OTHER INFORMATION: Primer Glk2

<400> SEQUENCE: 10
cattcttcaa ctgctccgct aaagtcaaaa taattctttc tcgtctgttt cctgtgtgaa    60
attgtta                                                              67

<210> SEQ ID NO 11
<211> LENGTH: 1270
<212> TYPE: DNA
<213> ORGANISM: Artificial Sequence
<220> FEATURE:
<223> OTHER INFORMATION: LoxP-cat-loxP Trc cassette "insert"

<400> SEQUENCE: 11
ggatgcatat ggcggccgca taacttcgta tagcatacat tatacgaagt tatctagagt    60
tgcatgcctg caggtccgaa tttctgccat tcatccgctt attatcactt attcaggcgt    120
```

```
agcaccaggc gtttaagggc accaataact gccttaaaaa aattacgccc cgccctgcca      180
ctcatcgcag tactgttgta attcattaag cattctgccg acatggaagc catcacaaac      240
ggcatgatga acctgaatcg ccagcggcat cagcaccttg tcgccttgcg tataatattt      300
gcccatggtg aaaacggggg cgaagaagtt gtccatattg gccacgttta aatcaaaact      360
ggtgaaactc acccagggat tggctgagac gaaaaacata ttctcaataa acccttttagg     420 gaaataggcc aggttttcac cgtaacacgc cacatcttgc gaatatatgt gtagaaactg      480
ccggaaatcg tcgtggtatt cactccagag cgatgaaaac gtttcagttt gctcatggaa      540
gttataggta cattgagcaa ctgactgaaa tgcctcaaaa tgttctttac gatgccattg      780
aacggtgtaa caagggtgaa cactatccca tatcaccagc tcaccgtctt tcattgccat      600
acggaattcc ggatgagcat tcatcaggcg ggcaagaatg tgaataaagg ccggataaaa      660
cttgtgctta tttttctta cggtctttaa aaaggccgta atatccagct gaacggtctg       720
ggatatatca acggtggtat atccagtgat tttttctcc attttagctt ccttagctcc       840
tgaaaatctc gataactcaa aaaatacgcc cggtagtgat cttatttcat tatggtgaaa      900
gttggaacct cttacgtgcc gatcaacgtc tcattttcgc caaaagttgg cccagggctt      960
cccggtatca acagggacac caggatttat ttattctgcg aagtgatctt ccgtcacagg     1020
tatttattcg gactctagat aacttcgtat agcatacatt atacgaagtt atggatcatg     1080
gctgtgcagg tcgtaaatca ctgcataatt cgtgtcgctc aaggcgcact cccgttctgg     1140
ataatgtttt ttgcgccgac atcataacgg ttctggcaaa tattctgaaa tgagctgttg     1200
acaattaatc atccggctcg tataatgtgt ggaattgtga gcggataaca atttcacaca     1260
ggaaacagac                                                            1270

<210> SEQ ID NO 12
<211> LENGTH: 30
<212> TYPE: DNA
<213> ORGANISM: Artificial Sequence
<220> FEATURE:
<223> OTHER INFORMATION: Primer GalB1

<400> SEQUENCE: 12
actttggtcg tgaacatttc ccgtgggaaa                                        30

<210> SEQ ID NO 13
<211> LENGTH: 28
<212> TYPE: DNA
<213> ORGANISM: Artificial Sequence
<220> FEATURE:
<223> OTHER INFORMATION: Primer GalC11

<400> SEQUENCE: 13
agaaagataa gcaccgagga tcccgata                                          28

<210> SEQ ID NO 14
<211> LENGTH: 26
<212> TYPE: DNA
<213> ORGANISM: Artificial Sequence
<220> FEATURE:
<223> OTHER INFORMATION: Primer GlkB1

<400> SEQUENCE: 14
aacaggagtg ccaaacagtg cgccga                                            26

<210> SEQ ID NO 15
```

<211> LENGTH: 30
<212> TYPE: DNA
<213> ORGANISM: Artificial Sequence
<220> FEATURE:
<223> OTHER INFORMATION: Primer GlkC11

<400> SEQUENCE: 15
ctattcggcg caaaatcaac gtgaccgcct                                    30

<210> SEQ ID NO 16
<211> LENGTH: 99
<212> TYPE: DNA
<213> ORGANISM: Artificial Sequence
<220> FEATURE:
<223> OTHER INFORMATION: Primer edd1

<400> SEQUENCE: 16
atgaatccac aattgttacg cgtaacaaat cgaatcattg aacgttcgcg cgagactcgc    60
tctgcttatc tcgcccggat ttatcgataa gctggatcc                          99

<210> SEQ ID NO 17
<211> LENGTH: 98
<212> TYPE: DNA
<213> ORGANISM: Artificial Sequence
<220> FEATURE:
<223> OTHER INFORMATION: Primer edd2

<400> SEQUENCE: 17
ttaaaaagtg atacaggttg cgccctgttc ggcaccggac agttttttcac gcaaggcgct   60 gaataattca cgtcctgtcg gatgcatatg gcggccgc                           98

<210> SEQ ID NO 18
<211> LENGTH: 22
<212> TYPE: DNA
<213> ORGANISM: Artificial Sequence
<220> FEATURE:
<223> OTHER INFORMATION: Primer edd3

<400> SEQUENCE: 18
taacatgatc ttgcgcagat tg                                            22

<210> SEQ ID NO 19
<211> LENGTH: 21
<212> TYPE: DNA
<213> ORGANISM: Artificial Sequence
<220> FEATURE:
<223> OTHER INFORMATION: Primer edd4

<400> SEQUENCE: 19
actgcacact cggtacgcag a                                             21

<210> SEQ ID NO 20
<211> LENGTH: 29
<212> TYPE: DNA
<213> ORGANISM: Artificial Sequence
<220> FEATURE:
<223> OTHER INFORMATION: CN1, encoding mutated trc promoter driving glk
      expression

<400> SEQUENCE: 20
ctgacaatta atcatccggc tcgtataat                                     29

<210> SEQ ID NO 21
<211> LENGTH: 29
<212> TYPE: DNA

```
<213> ORGANISM: Artificial Sequence
<220> FEATURE:
<223> OTHER INFORMATION: CN2, encoding parent trc promoter

<400> SEQUENCE: 21
ttgacaatta atcatccggc tcgtataat                                      29

<210> SEQ ID NO 22
<211> LENGTH: 25
<212> TYPE: DNA
<213> ORGANISM: Artificial Sequence
<220> FEATURE:
<223> OTHER INFORMATION: Primer gapA1

<400> SEQUENCE: 22
atgaccatct gaccatttgt gtcaa                                          25

<210> SEQ ID NO 23
<211> LENGTH: 25
<212> TYPE: DNA
<213> ORGANISM: Artificial Sequence
<220> FEATURE:
<223> OTHER INFORMATION: Primer gapA2

<400> SEQUENCE: 23
aatgcgctaa cagcgtaaag tcgtg                                          25

<210> SEQ ID NO 24
<211> LENGTH: 35
<212> TYPE: DNA
<213> ORGANISM: Artificial Sequence
<220> FEATURE:
<223> OTHER INFORMATION: Primer gapA3

<400> SEQUENCE: 24
gatacctact ttgatagtca catattccac cagct                               35

<210> SEQ ID NO 25
<211> LENGTH: 35
<212> TYPE: DNA
<213> ORGANISM: Artificial Sequence
<220> FEATURE:
<223> OTHER INFORMATION: Primer gapA4

<400> SEQUENCE: 25
agctggtgga atatgtgact atcaaagtag gtatc                               35

<210> SEQ ID NO 26
<211> LENGTH: 35
<212> TYPE: DNA
<213> ORGANISM: Artificial Sequence
<220> FEATURE:
<223> OTHER INFORMATION: Primer gapA5

<400> SEQUENCE: 26
gatacctact ttgatagtca aatattccac cagct                               35

<210> SEQ ID NO 27
<211> LENGTH: 35
<212> TYPE: DNA
<213> ORGANISM: Artificial Sequence
<220> FEATURE:
<223> OTHER INFORMATION: Primer gapA6

<400> SEQUENCE: 27
agctggtgga atatttgact atcaaagtag gtatc                               35
```

<210> SEQ ID NO 28
<211> LENGTH: 42
<212> TYPE: DNA
<213> ORGANISM: Artificial Sequence
<220> FEATURE:
<223> OTHER INFORMATION: short 1.5 GI promoter

<400> SEQUENCE: 28
gcccttgact atgccacatc ctgagcaaat aattcaacca ct                42

<210> SEQ ID NO 29
<211> LENGTH: 98
<212> TYPE: DNA
<213> ORGANISM: Artificial Sequence
<220> FEATURE:
<223> OTHER INFORMATION: Primer gapA-R1

<400> SEQUENCE: 29
agtcatatat tccaccagct atttgttagt gaataaaagt ggttgaatta tttgctcagg    60
atgtggcata gtcaagggca tatgaatatc ctccttag                          98

<210> SEQ ID NO 30
<211> LENGTH: 80
<212> TYPE: DNA
<213> ORGANISM: Artificial Sequence
<220> FEATURE:
<223> OTHER INFORMATION: Primer gapA-R2

<400> SEQUENCE: 30
gctcacatta cgtgactgat tctaacaaaa cattaacacc aactggcaaa attttgtccg    60
tgtaggctgg agctgcttcg                                              80

<210> SEQ ID NO 31
<211> LENGTH: 42
<212> TYPE: DNA
<213> ORGANISM: Artificial Sequence
<220> FEATURE:
<223> OTHER INFORMATION: short 1.20 GI promoter

<400> SEQUENCE: 31
gcccttgacg atgccacatc ctgagcaaat aattcaacca ct                42

<210> SEQ ID NO 32
<211> LENGTH: 42
<212> TYPE: DNA
<213> ORGANISM: Artificial Sequence
<220> FEATURE:
<223> OTHER INFORMATION: short 1.6 GI promoter

<400> SEQUENCE: 32
gcccttgaca atgccacatc ctgagcaaat aattcaacca ct                42

<210> SEQ ID NO 33
<211> LENGTH: 24
<212> TYPE: DNA
<213> ORGANISM: Artificial Sequence
<220> FEATURE:
<223> OTHER INFORMATION: Primer gapA-R3

<400> SEQUENCE: 33
gtcgacaaac gctggtatac ctca                                    24

<210> SEQ ID NO 34

<211> LENGTH: 98
<212> TYPE: DNA
<213> ORGANISM: Artificial Sequence
<220> FEATURE:
<223> OTHER INFORMATION: Primer gapA-R4

<400> SEQUENCE: 34
agtcatatat tccaccagct atttgttagt gaataaaagt ggttgaatta tttgctcagg    60
atgtggcatc gtcaagggca tatgaatatc ctccttag                           98

<210> SEQ ID NO 35
<211> LENGTH: 98
<212> TYPE: DNA
<213> ORGANISM: Artificial Sequence
<220> FEATURE:
<223> OTHER INFORMATION: Primer gapA-R5

<400> SEQUENCE: 35
agtcatatat tccaccagct atttgttagt gaataaaagt ggttgaatta tttgctcagg    60
atgtggcatt gtcaagggca tatgaatatc ctccttag                           98

<210> SEQ ID NO 36
<211> LENGTH: 60
<212> TYPE: DNA
<213> ORGANISM: Artificial Sequence
<220> FEATURE:
<223> OTHER INFORMATION: Primer mgsA-1

<400> SEQUENCE: 36
gtacattatg gaactgacga ctcgcacttt acctgcgcgg tgtaggctgg agctgcttcg    60

<210> SEQ ID NO 37
<211> LENGTH: 60
<212> TYPE: DNA
<213> ORGANISM: Artificial Sequence
<220> FEATURE:
<223> OTHER INFORMATION: Primer mgsA-2

<400> SEQUENCE: 37
cttcagacgg tccgcgagat aacgctgata atcggggatc catatgaata tcctccttag    60

<210> SEQ ID NO 38
<211> LENGTH: 22
<212> TYPE: DNA
<213> ORGANISM: Artificial Sequence
<220> FEATURE:
<223> OTHER INFORMATION: Primer mgsA-3

<400> SEQUENCE: 38
cttgaattgt tggatggcga tg                                            22

<210> SEQ ID NO 39
<211> LENGTH: 21
<212> TYPE: DNA
<213> ORGANISM: Artificial Sequence
<220> FEATURE:
<223> OTHER INFORMATION: Primer mgsA-4

<400> SEQUENCE: 39
cgtcacgtta ttggatgaga g                                             21

<210> SEQ ID NO 40
<211> LENGTH: 100
<212> TYPE: DNA
<213> ORGANISM: Artificial Sequence
<220> FEATURE:
<223> OTHER INFORMATION: Primer PppcF

<400> SEQUENCE: 40 cgattttta acatttccat aagttacgct tatttaaagc gtcgtgaatt taatgacgta        60
aattcctgct atttattcgt gtgtaggctg gagctgcttc                             100

<210> SEQ ID NO 41
<211> LENGTH: 100
<212> TYPE: DNA
<213> ORGANISM: Artificial Sequence
<220> FEATURE:
<223> OTHER INFORMATION: Primer PppcR

<400> SEQUENCE: 41
tcgcattggc gcgaatatgc tcgggctttg cttttcgtca gtggttgaat tatttgctca        60
ggatgtggca ttgtcaaggg catatgaata tcctccttag                              100

<210> SEQ ID NO 42
<211> LENGTH: 30
<212> TYPE: DNA
<213> ORGANISM: Artificial Sequence
<220> FEATURE:
<223> OTHER INFORMATION: Primer SeqppcR 7

<400> SEQUENCE: 42
gcggaatatt gttcgttcat attaccccag                                         30

<210> SEQ ID NO 43
<211> LENGTH: 90
<212> TYPE: DNA
<213> ORGANISM: Artificial Sequence
<220> FEATURE:
<223> OTHER INFORMATION: Primer 3G144

<400> SEQUENCE: 43
ccaggctgat tgaaatgccc ttctgtttca ggcataaagc cccaaagtca taagtacac         60 tggcagcgcg gtgtaggctg gagctgcttc                                         90

<210> SEQ ID NO 44
<211> LENGTH: 93
<212> TYPE: DNA
<213> ORGANISM: Artificial Sequence
<220> FEATURE:
<223> OTHER INFORMATION: Primer 3G145

<400> SEQUENCE: 44
gcatggctac tcctcaacga cgttgtctgt tagtggttga attatttgct caggatgtgg        60
cattgtcaag ggcattccgg ggatccgtcg acc                                     93

<210> SEQ ID NO 45
<211> LENGTH: 25
<212> TYPE: DNA
<213> ORGANISM: Artificial Sequence
<220> FEATURE:
<223> OTHER INFORMATION: Primer YClKUp

<400> SEQUENCE: 45
gataataccg cgttcatcct gggcc                                              25

<210> SEQ ID NO 46
<211> LENGTH: 25
<212> TYPE: DNA

<213> ORGANISM: Artificial Sequence
<220> FEATURE:
<223> OTHER INFORMATION: Primer YCIKDn

<400> SEQUENCE: 46
gcgagttcac ttcatgggcg tccat         25

<210> SEQ ID NO 47
<211> LENGTH: 98
<212> TYPE: DNA
<213> ORGANISM: Artificial Sequence
<220> FEATURE:
<223> OTHER INFORMATION: Primer yqhCFRTF

<400> SEQUENCE: 47
ttaattcccc tgcatcgccc gcattcttgc cgcatcttcc cccggcgtca caccgaagta      60
acgtttaaac tcacggctgt gtaggctgga gctgcttc         98

<210> SEQ ID NO 48
<211> LENGTH: 100
<212> TYPE: DNA
<213> ORGANISM: Artificial Sequence
<220> FEATURE:
<223> OTHER INFORMATION: Primer CyqhD1.6

<400> SEQUENCE: 48
ctcccttgct gggccaatat gagggcagag aacgatctgc ctggttgaat tatttgctca      60
ggatgtggca ttgtcaaggg catatgaata tcctccttag         100

<210> SEQ ID NO 49
<211> LENGTH: 46
<212> TYPE: DNA
<213> ORGANISM: Artificial Sequence
<220> FEATURE:
<223> OTHER INFORMATION: Primer yqhBF

<400> SEQUENCE: 49
atcgcccgca ttcttgccgc atcttccccc ggcgtcacac cgaagt         46

<210> SEQ ID NO 50
<211> LENGTH: 100
<212> TYPE: DNA
<213> ORGANISM: Artificial Sequence
<220> FEATURE:
<223> OTHER INFORMATION: Primer pta 1

<400> SEQUENCE: 50
atgtcgagta agttagtact ggttctgaac tgcggtagtt cttcactgaa atttgccatc      60
atcgatgcag taaatggtga tgtgtaggct ggagctgctt         100

<210> SEQ ID NO 51
<211> LENGTH: 100
<212> TYPE: DNA
<213> ORGANISM: Artificial Sequence
<220> FEATURE:
<223> OTHER INFORMATION: Primer ack-pta 2

<400> SEQUENCE: 51
ttactgctgc tgtgcagact gaatcgcagt cagcgcgatg gtgtagacga tatcgtcaac      60
cagtgcgcca cgggacaggt catatgaata tcctccttag         100

<210> SEQ ID NO 52
<211> LENGTH: 20

```
<212> TYPE: DNA
<213> ORGANISM: Artificial Sequence
<220> FEATURE:
<223> OTHER INFORMATION: Primer ack-U

<400> SEQUENCE: 52
attcattgag tcgtcaaatt                                                    20

<210> SEQ ID NO 53
<211> LENGTH: 20
<212> TYPE: DNA
<213> ORGANISM: Artificial Sequence
<220> FEATURE:
<223> OTHER INFORMATION: Primer ack-D

<400> SEQUENCE: 53
attgcggaca tagcgcaaat                                                    20

<210> SEQ ID NO 54
<211> LENGTH: 98
<212> TYPE: DNA
<213> ORGANISM: Artificial Sequence
<220> FEATURE:
<223> OTHER INFORMATION: Primer ptsHFRT1

<400> SEQUENCE: 54
atgttccagc aagaagttac cattaccgct ccgaacggtc tgcacacccg ccctgctgcc        60
cagtttgtaa aagaagctgt gtaggctgga gctgcttc                               98

<210> SEQ ID NO 55
<211> LENGTH: 97
<212> TYPE: DNA
<213> ORGANISM: Artificial Sequence
<220> FEATURE:
<223> OTHER INFORMATION: Primer crrFRT11

<400> SEQUENCE: 55
ttacttcttg atgcggataa ccggggtttc acccacggtt acgctaccgg acagtttgat        60
cagttctttg atttcgtcat atgaatatcc tccttag                                97

<210> SEQ ID NO 56
<211> LENGTH: 36
<212> TYPE: DNA
<213> ORGANISM: Artificial Sequence
<220> FEATURE:
<223> OTHER INFORMATION: Primer crrR

<400> SEQUENCE: 56
cctgttttgt gctcagctca tcagtggctt gctgaa                                 36

<210> SEQ ID NO 57
<211> LENGTH: 100
<212> TYPE: DNA
<213> ORGANISM: Artificial Sequence
<220> FEATURE:
<223> OTHER INFORMATION: Primer DaldAF

<400> SEQUENCE: 57
atgtcagtac ccgttcaaca tcctatgtat atcgatggac agtttgttac ctggcgtgga        60
gacgcatgga ttgatgtggt tgtgtaggct ggagctgctt                             100

<210> SEQ ID NO 58
<211> LENGTH: 100
<212> TYPE: DNA
```

<213> ORGANISM: Artificial Sequence
<220> FEATURE:
<223> OTHER INFORMATION: Primer DaldAR

<400> SEQUENCE: 58
ttaagactgt aaataaacca cctgggtctg cagatattca tgcaagccat gtttaccatc    60
tgcgccgcca ataccggatt catatgaata tcctccttag                         100

<210> SEQ ID NO 59
<211> LENGTH: 20
<212> TYPE: DNA
<213> ORGANISM: Artificial Sequence
<220> FEATURE:
<223> OTHER INFORMATION: Primer aldAF300

<400> SEQUENCE: 59
ttatcgttca cgttgatttt                                                20

<210> SEQ ID NO 60
<211> LENGTH: 20
<212> TYPE: DNA
<213> ORGANISM: Artificial Sequence
<220> FEATURE:
<223> OTHER INFORMATION: Primer aldAR300

<400> SEQUENCE: 60
gaaaaaagtg actgccgaag                                                20

<210> SEQ ID NO 61
<211> LENGTH: 100
<212> TYPE: DNA
<213> ORGANISM: Artificial Sequence
<220> FEATURE:
<223> OTHER INFORMATION: Primer DaldBF

<400> SEQUENCE: 61
cgtctaccct tgttatacct cacaccgcaa ggagacgatc atgaccaata atcccccttc    60
agcacagatt aagcccggcg gtgtaggctg gagctgcttc                         100

<210> SEQ ID NO 62
<211> LENGTH: 100
<212> TYPE: DNA
<213> ORGANISM: Artificial Sequence
<220> FEATURE:
<223> OTHER INFORMATION: Primer DaldBR

<400> SEQUENCE: 62
gcatcaggca atgaataccc aatgcgacca gcttcttata tcagaacagc cccaacggtt    60
tatccgagta gctcaccagc catatgaata tcctccttag                         100

<210> SEQ ID NO 63
<211> LENGTH: 22
<212> TYPE: DNA
<213> ORGANISM: Artificial Sequence
<220> FEATURE:
<223> OTHER INFORMATION: Primer aldBF

<400> SEQUENCE: 63
atgaccaata atccccttc ag                                              22

<210> SEQ ID NO 64
<211> LENGTH: 21
<212> TYPE: DNA
<213> ORGANISM: Artificial Sequence

```
<220> FEATURE:
<223> OTHER INFORMATION: Primer aldBR

<400> SEQUENCE: 64
gcttcttata tcagaacagc c                                              21

<210> SEQ ID NO 65
<211> LENGTH: 13669
<212> TYPE: DNA
<213> ORGANISM: Artificial sequence
<220> FEATURE:
<223> OTHER INFORMATION: Plasmid pSYCO101

<400> SEQUENCE: 65
tagtaaagcc ctcgctagat tttaatgcgg atgttgcgat tacttcgcca actattgcga      60
taacaagaaa aagccagcct ttcatgatat atctcccaat ttgtgtaggg cttattatgc     120
acgcttaaaa ataataaaag cagacttgac ctgatagttt ggctgtgagc aattatgtgc     180
ttagtgcatc taacgcttga gttaagccgc gccgcgaagc ggcgtcggct tgaacgaatt     240
gttagacatt atttgccgac taccttggtg atctcgcctt tcacgtagtg gacaaattct     300
tccaactgat ctgcgcgcga ggccaagcga tcttcttctt gtccaagata agcctgtcta     360
gcttcaagta tgacgggctg atactgggcc ggcaggcgct ccattgccca gtcggcagcg     420
acatccttcg gcgcgatttt gccggttact gcgctgtacc aaatgcggga caacgtaagc     480
actacatttc gctcatcgcc agcccagtcg ggcggcgagt tccatagcgt taaggtttca     540
tttagcgcct caaatagatc ctgttcagga accggatcaa agagttcctc cgccgctgga     600
cctaccaagg caacgctatg ttctcttgct tttgtcagca agatagccag atcaatgtcg     660
atcgtggctg gctcgaagat acctgcaaga atgtcattgc gctgccattc tccaaattgc     720
agttcgcgct tagctggata acgccacgga atgatgtcgt cgtgcacaac aatggtgact     780
tctacagcgc ggagaatctc gctctctcca ggggaagccg aagtttccaa aaggtcgttg     840
atcaaagctc gccgcgttgt ttcatcaagc cttacggtca ccgtaaccag caaatcaata     900
tcactgtgtg gcttcaggcc gccatccact gcggagccgt acaaatgtac ggccagcaac     960
gtcggttcga gatggcgctc gatgacgcca actacctctg atagttgagt cgatacttcg    1020
gcgatcaccg cttccctcat gatgtttaac tttgttttag ggcgactgcc ctgctgcgta    1080
acatcgttgc tgctccataa catcaaacat cgacccacgg cgtaacgcgc ttgctgcttg    1140
gatgcccgag gcatagactg taccccaaaa aaacagtcat aacaagccat gaaaaccgcc    1200
actgcgccgt taccaccgct gcgttcggtc aaggttctgg accagttgcg tgagcgcata    1260
cgctacttgc attacagctt acgaaccgaa caggcttatg tccactgggt tcgtgccttc    1320
atccgtttcc acggtgtgcg tcacccggca accttgggca gcagcgaagt cgaggcattt    1380
ctgtcctggc tggcgaacga gcgcaaggtt tcggtctcca cgcatcgtca ggcattggcg    1440
gccttgctgt tcttctacgg caaggtgctg tgcacggatc tgccctggct tcaggagatc    1500
ggaagacctc ggccgtcgcg gcgcttgccg gtggtgctga cccggatga agtggttcgc     1560 atcctcggtt ttctggaagg cgagcatcgt ttgttcgccc agcttctgta tggaacgggc    1620
atgcggatca gtgagggttt gcaactgcgg gtcaaggatc tggatttcga tcacggcacg    1680
atcatcgtgc gggagggcaa gggctccaag gatcgggcct tgatgttacc cgagagcttg    1740
gcacccagcc tgcgcgagca ggggaattaa ttcccacggg ttttgctgcc cgcaaacggg    1800
ctgttctggt gttgctagtt tgttatcaga atcgcagatc cggcttcagc cggtttgccg    1860
```

-continued

```
gctgaaagcg ctatttcttc cagaattgcc atgattttt  ccccacggga ggcgtcactg    1920
gctcccgtgt tgtcggcagc tttgattcga taagcagcat cgcctgtttc aggctgtcta    1980
tgtgtgactg ttgagctgta acaagttgtc tcaggtgttc aatttcatgt tctagttgct    2040
ttgttttact ggtttcacct gttctattag gtgttacatg ctgttcatct gttacattgt    2100
cgatctgttc atggtgaaca gctttgaatg caccaaaaac tcgtaaaagc tctgatgtat    2160 ctatctttt  tacaccgttt tcatctgtgc atatggacag ttttcccttt gatatgtaac    2220
ggtgaacagt tgttctactt tgtttgtta  gtcttgatgc ttcactgata gatacaagag    2280
ccataagaac ctcagatcct tccgtattta gccagtatgt tctctagtgt ggttcgttgt    2340
ttttgcgtga gccatgagaa cgaaccattg agatcatact tactttgcat gtcactcaaa    2400
aattttgcct caaaactggt gagctgaatt tttgcagtta aagcatcgtg tagtgttttt    2460
cttagtccgt tatgtaggta ggaatctgat gtaatggttg ttggtatttt gtcaccattc    2520
atttttatct ggttgttctc aagttcggtt acgagatcca tttgtctatc tagttcaact    2580
tggaaaatca acgtatcagt cgggcggcct cgcttatcaa ccaccaattt catattgctg    2640
taagtgttta atctttact  tattggtttc aaaacccatt ggttaagcct tttaaactca    2700
tggtagttat tttcaagcat taacatgaac ttaaattcat caaggctaat ctctatattt    2760
gccttgtgag ttttctttg  tgttagttct tttaataacc actcataaat cctcatagag    2820
tatttgtttt caaaagactt aacatgttcc agattatatt ttatgaattt ttttaactgg    2880
aaaagataag gcaatatctc ttcactaaaa actaattcta atttttcgct tgagaacttg    2940
gcatagtttg tccactggaa aatctcaaag cctttaacca aaggattcct gatttccaca    3000
gttctcgtca tcagctctct ggttgcttta gctaatacac cataagcatt ttccctactg    3060
atgttcatca tctgagcgta ttggttataa gtgaacgata ccgtccgttc tttccttgta    3120
gggttttcaa tcgtggggtt gagtagtgcc acacagcata aaattagctt ggtttcatgc    3180
tccgttaagt catagcgact aatcgctagt tcatttgctt tgaaaacaac taattcagac    3240
atacatctca attggtctag gtgattttaa tcactatacc aattgagatg ggctagtcaa    3300
tgataattac tagtcctttt cctttgagtt gtgggtatct gtaaattctg ctagacctt     3360 gctggaaaac ttgtaaattc tgctagaccc tctgtaaatt ccgctagacc tttgtgtgtt    3420
ttttttgttt atattcaagt ggttataatt tatagaataa agaaagaata aaaaagata     3480 aaaagaatag atcccagccc tgtgtataac tcactacttt agtcagttcc gcagtattac    3540
aaaaggatgt cgcaaacgct gtttgctcct ctacaaaaca gaccttaaaa ccctaaaggc    3600
ttaagtagca ccctcgcaag ctcgggcaaa tcgctgaata ttccttttgt ctccgaccat    3660
caggcacctg agtcgctgtc ttttcgtga  cattcagttc gctgcgctca cggctctggc    3720
agtgaatggg ggtaaatggc actacaggcg cctttatgg  attcatgcaa ggaaactacc    3780
cataatacaa gaaaagcccg tcacgggctt ctcagggcgt tttatggcgg gtctgctatg    3840
tggtgctatc tgactttttg ctgttcagca gttcctgccc tctgattttc cagtctgacc    3900
acttcggatt atcccgtgac aggtcattca gactggctaa tgcacccagt aaggcagcgg    3960
tatcatcaac aggcttaccc gtcttactgt cgggaattca tttaaatagt caaaagcctc    4020
cgaccggagg cttttgactg ctaggcgatc tgtgctgttt gccacggtat gcagcaccag    4080
cgcgagatta tgggctcgca cgctcgactg tcggacgggg gcactggaac gagaagtcag    4140
gcgagccgtc acgcccttga caatgccaca tcctgagcaa ataattcaac cactaaacaa    4200
atcaaccgcg tttcccggag gtaaccaagc ttgcgggaga gaatgatgaa caagagccaa    4260
```

```
caagttcaga caatcaccct ggccgccgcc cagcaaatgg cggcggcggt ggaaaaaaaa   4320
gccactgaga tcaacgtggc ggtggtgttt ccgtagttga ccgcggagg caacacgctg    4380 cttatccagc ggatggacga ggccttcgtc tccagctgcg atatttccct gaataaagcc   4440
tggagcgcct gcagcctgaa gcaaggtacc catgaaatta cgtcagcggt ccagccagga   4500
caatctctgt acggtctgca gctaaccaac caacagcgaa ttattatttt tggcggcggc   4560
ctgccagtta ttttttaatga gcaggtaatt ggcgccgtcg gcgttagcgg cggtacggtc   4620
gagcaggatc aattattagc ccagtgcgcc ctggattgtt tttccgcatt ataacctgaa    4680
gcgagaaggt atattatgag ctatcgtatg ttccgccagg cattctgagt gttaacgagg    4740
ggaccgtcat gtcgctttca ccgccaggcg tacgcctgtt ttacgatccg cgcgggcacc    4800
atgccggcgc catcaatgag ctgtgctggg ggctggagga gcaggggtc ccctgccaga    4860 ccataaccta tgacggaggc ggtgacgccg ctgcgctggg cgccctggcg gccagaagct    4920
cgcccctgcg ggtgggtatc gggctcagcg cgtccggcga gatagccctc actcatgccc    4980
agctgccggc ggacgcgccg ctggctaccg gacacgtcac cgatagcgac gatcaactgc    5040
gtacgctcgg cgccaacgcc gggcagctgg ttaaagtcct gccgttaagt gagagaaact    5100
gaatgtatcg tatctatacc cgcaccgggg ataaaggcac caccgccctg tacggcggca    5160
gccgcatcga gaaagaccat attcgcgtcg aggcctacgg caccgtcgat gaactgatat    5220
cccagctggg cgtctgctac gccacgaccc gcgacgccgg gctgcgggaa agcctgcacc    5280
atattcagca gacgctgttc gtgctggggg ctgaactggc cagcgatgcg cggggcctga    5340
cccgcctgag ccagacgatc ggcgaagagg agatcaccgc cctggagcgg cttatcgacc    5400
gcaatatggc cgagagcggc ccgttaaaac agttcgtgat cccggggagg aatctcgcct    5460
ctgcccagct gcacgtggcg cgcacccagt cccgtcggct cgaacgcctg ctgacggcca    5520
tggaccgcgc gcatccgctg cgcgacgcgc tcaaacgcta cagcaatcgc ctgtcggatg    5580
ccctgttctc catggcgcga atcgaagaga ctaggcctga tgcttgcgct tgaactggcc    5640
tagcaaacac agaaaaaagc ccgcacctga cagtgcgggc ttttttttc ctaggcgatc    5700 tgtgctgttt gccacggtat gcagcaccag cgcgagatta tgggctcgca cgctcgactg    5760
tcggacgggg gcactggaac gagaagtcag gcgagccgtc acgcccttga caatgccaca    5820
tcctgagcaa ataattcaac cactaaacaa atcaaccgcg tttcccggag gtaaccaagc    5880
ttcacctttt gagccgatga acaatgaaaa gatcaaaacg atttgcagta ctggcccagc    5940
gccccgtcaa tcaggacggg ctgattggcg agtggcctga agaggggctg atcgccatgg    6000
acagcccctt tgacccggtc tcttcagtaa aagtggacaa cggtctgatc gtcgaactgg    6060
acggcaaacg ccgggaccag tttgacatga tcgaccgatt tatcgccgat tacgcgatca    6120
acgttgagcg cacagagcag gcaatgcgcc tggaggcggt ggaaatagcc cgtatgctgg    6180
tggatattca cgtcagccgg gaggagatca ttgccatcac taccgccatc acgccggcca    6240
aagcggtcga ggtgatggcg cagatgaacg tggtggagat gatgatggcg ctgcagaaga    6300
tgcgtgcccg ccggaccccc tccaaccagt gccacgtcac caatctcaaa gataatccgg    6360
tgcagattgc cgctgacgcc gccgaggcg ggatccgcgg cttctcagaa caggagacca    6420
cggtcggtat cgcgcgctac gcgccgtta acgccctggc gctgttggtc ggttcgcagt    6480
gcggccgccc cggcgtgttg acgcagtgct cggtggaaga ggccaccgag ctggagctgg    6540
gcatgcgtgg cttaaccagc tacgccgaga cggtgtcggt ctacgcacc gaagcggtat    6600
```

```
ttaccgacgg cgatgatacg ccgtggtcaa aggcgttcct cgcctcggcc tacgcctccc    6660
gcgggttgaa aatgcgctac acctccggca ccggatccga agcgctgatg ggctattcgg    6720
agagcaagtc gatgctctac ctcgaatcgc gctgcatctt cattactaaa ggcgccgggg    6780
ttcagggact gcaaaacggc gcggtgagct gtatcggcat gaccggcgct gtgccgtcgg    6840
gcattcgggc ggtgctggcg gaaaacctga tcgcctctat gctcgacctc gaagtggcgt    6900
ccgccaacga ccagactttc tcccactcgg atattcgccg caccgcgcgc accctgatgc    6960
agatgctgcc gggcaccgac tttattttct ccggctacag cgcggtgccg aactacgaca    7020
acatgttcgc cggctcgaac ttcgatgcgg aagattttga tgattacaac atcctgcagc    7080
gtgacctgat ggttgacggc ggcctgcgtc cggtgaccga gcggaaacc attgccattc     7140
gccagaaagc ggcgcgggcg atccaggcgg ttttccgcga gctggggctg ccgccaatcg    7200
ccgacgagga ggtggaggcc gccacctacg cgcacggcag caacgagatg ccgccgcgta    7260
acgtggtgga ggatctgagt gcggtggaag agatgatgaa gcgcaacatc accggcctcg    7320
atattgtcgg cgcgctgagc cgcagcggct ttgaggatat cgccagcaat attctcaata    7380
tgctgcgcca gcgggtcacc ggcgattacc tgcagacctc ggccattctc gatcggcagt    7440
tcgaggtggt gagtgcggtc aacgacatca atgactatca ggggccgggc accggctatc    7500
gcatctctgc cgaacgctgg gcggagatca aaaatattcc gggcgtggtt cagcccgaca    7560
ccattgaata aggcggtatt cctgtgcaac agacaaccca aattcagccc tcttttaccc    7620
tgaaaacccg cgagggcggg gtagcttctg ccgatgaacg cgccgatgaa gtggtgatcg    7680
gcgtcggccc tgccttcgat aaacaccagc atcacactct gatcgatatg ccccatggcg    7740
cgatcctcaa agagctgatt gccggggtgg aagaagaggg gcttcacgcc cggtggtgc     7800
gcattctgcg cacgtccgac gtctccttta tggcctggga tgcggccaac ctgagcggct    7860
cggggatcgg catcggtatc cagtcgaagg ggaccacggt catccatcag cgcgatctgc    7920
tgccgctcag caacctggag ctgttctccc aggcgccgct gctgacgctg agacctacc     7980
ggcagattgg caaaaacgct gcgcgctatg cgcgcaaaga gtcaccttcg ccggtgccgg    8040
tggtgaacga tcagatggtg cggccgaaat ttatggccaa agccgcgcta tttcatatca    8100
aagagaccaa acatgtggtg caggacgccg agcccgtcac cctgcacatc gacttagtaa    8160
gggagtgacc atgagcgaga aaaccatgcg cgtgcaggat tatccgttag ccacccgctg    8220
cccggagcat atcctgacgc ctaccggcaa accattgacc gatattaccc tcgagaaggt    8280
gctctctggc gaggtgggcc gcaggatgt gcggatctcc cgccagaccc ttgagtacca     8340
ggcgcagatt gccgagcaga tgcagcgcca tgccggtggcg cgcaatttcc gccgcgcggc    8400
ggagcttatc gccattcctg acgagcgcat tctggctatc tataacgcgc tgcgcccgtt    8460
ccgctcctcg caggcggagc tgctggcgat cgccgacgag ctggagcaca cctggcatgc    8520
gacagtgaat gccgcctttg tccgggagtc ggcggaagtg tatcagcagc ggcataagct    8580
gcgtaaagga agctaagcgg aggtcagcat gccgttaata gccgggattg atatcggcaa    8640
cgccaccacc gaggtggcgc tggcgtccga ctacccgcag gcgagggcgt ttgttgccag    8700
cgggatcgtc gcgacgacgg gcatgaaagg gacgcgggac aatatcgccg ggaccctcgc    8760
cgcgctggag caggccctgg cgaaaacacc gtggtcgatg agcgatgtct ctcgcatcta    8820
tcttaacgaa gccgcgccgg tgattggcga tgtggcgatg gagaccatca ccgagaccat    8880
tatcaccgaa tcgaccatga tcggtcataa cccgcagacg ccgggcgggg tgggcgttgg    8940
cgtggggacg actatcgccc tcgggcggct ggcgacgctg ccggcggcgc agtatgccga    9000
```

```
ggggtggatc gtactgattg acgacgccgt cgatttcctt gacgccgtgt ggtggctcaa    9060
tgaggcgctc gaccggggga tcaacgtggt ggcggcgatc ctcaaaaagg acgacggcgt    9120
gctggtgaac aaccgcctgc gtaaaaccct gccggtggtg gatgaagtga cgctgctgga    9180
gcaggtcccc gagggggtaa tggcggcggt ggaagtggcc gcgccgggcc aggtggtgcg    9240
gatcctgtcg aatccctacg ggatcgccac cttcttcggg ctaagcccgg aagagaccca    9300
ggccatcgtc cccatcgccc gcgccctgat tggcaaccgt tccgcggtgg tgctcaagac    9360
cccgcagggg gatgtgcagt cgcgggtgat cccggcgggc aacctctaca ttagcggcga    9420
aaagcgccgc ggagaggccg atgtcgccga gggcgcggaa gccatcatgc aggcgatgag    9480
cgcctgcgct ccggtacgcg acatccgcgg cgaaccgggc acccacgccg gcggcatgct    9540
tgagcgggtg cgcaaggtaa tggcgtccct gaccggccat gagatgagcg cgatatacat    9600
ccaggatctg ctggcggtgg atacgtttat tccgcgcaag gtgcagggcg ggatggccgg    9660
cgagtgcgcc atggagaatg ccgtcgggat ggcggcgatg gtgaaagcgg atcgtctgca    9720
aatgcaggtt atcgcccgcg aactgagcgc ccgactgcag accgaggtgg tggtgggcgg    9780
cgtggaggcc aacatggcca tcgccggggc gttaaccact cccggctgtg cggcgccgct    9840
ggcgatcctc gacctcggcg ccggctcgac ggatgcggcg atcgtcaacg cggaggggca    9900
gataacggcg gtccatctcg ccggggcggg gaatatggtc agcctgttga ttaaaaccga    9960
gctgggcctc gaggatcttt cgctggcgga agcgataaaa aaatacccgc tggccaaagt   10020
ggaaagcctg ttcagtattc gtcacgagaa tggcgcggtg gagttctttc gggaagccct   10080
cagcccggcg gtgttcgcca aagtggtgta catcaaggag ggcgaactgg tgccgatcga   10140
taacgccagc ccgctggaaa aaattcgtct cgtgcgccgg caggcgaaag agaaagtgtt   10200
tgtcaccaac tgcctgcgcg cgctgcgcca ggtctcaccc ggcggttcca ttcgcgatat   10260
cgcctttgtg gtgctggtgg gcggctcatc gctggacttt gagatcccgc agcttatcac   10320
ggaagccttg tcgcactatg gcgtggtcgc cgggcagggc aatattcggg aacagaagg    10380 gccgcgcaat gcggtcgcca ccgggctgct actggccggt caggcgaatt aaacgggcgc   10440
tcgcgccagc ctctaggtac aaataaaaaa ggcacgtcag atgacgtgcc ttttttcttg   10500
tctagagtac tggcgaaagg gggatgtgct gcaaggcgat taagttgggt aacgccaggg   10560
ttttcccagt cacgacgttg taaaacgacg gccagtgaat tcgagctcgg tacccggggc   10620
ggccgcgcta gcgcccgatc cagctggagt ttgtagaaac gcaaaaaggc catccgtcag   10680
gatggccttc tgcttaattt gatgcctggc agtttatggc gggcgtcctg cccgccaccc   10740
tccgggccgt tgcttcgcaa cgttcaaatc cgctcccggc ggatttgtcc tactcaggag   10800
agcgttcacc gacaaacaac agataaaacg aaaggcccag tctttcgact gagcctttcg   10860
ttttatttga tgcctggcag ttccctactc tcgcatgggg agaccccaca ctaccatcgg   10920
cgctacggcg tttcacttct gagttcggca tggggtcagg tgggaccacc gcgctactgc   10980
cgccaggcaa attctgtttt atcagaccgc ttctgcgttc tgatttaatc tgtatcaggc   11040
tgaaaatctt ctctcatccg ccaaaacagc caagcttgca tgcctgcagc ccgggttacc   11100
atttcaacag atcgtcctta gcatataagt agtcgtcaaa aatgaattca acttcgtctg   11160
tttcggcatt gtagccgcca actctgatgg attcgtggtt tttgacaatg atgtcacagc   11220 cttttttcctt taggaagtcc aagtcgaaag tagtggcaat accatgatc ttacaaccgg   11280 cggcttttcc ggcggcaata cctgctggag cgtcttcaaa tactactacc ttagatttgg   11340
```

```
aagggtcttg ctcattgatc ggatatccta agccattcct gcccttcaga tatggttctg    11400
gatgaggctt accctgtttg acatcattag cggtaatgaa gtactttggt ctcctgattc    11460
ccagatgctc gaaccatttt tgtgccatat cacgggtacc ggaagttgcc acagcccatt    11520
tctcttttgg tagagcgttc aaagcgttgc acagcttaac tgcacctggg acttcaatgg    11580
atttttcacc gtacttgacc ggaatttcag cttctaattt gttaacatac tcttcattgg    11640
caaagtctgg agcgaactta gcaatggcat caaacgttct ccaaccatgc gagacttgga    11700
taacgtgttc agcatcgaaa taaggtttgt ccttaccgaa atccctccag aatgcagcaa    11760
tggctggttg agagatgata atggtaccgt cgacgtcgaa caaagcggcg ttaacttttca   11820 aagatagagg tttagtagtc aatcccataa ttctagtctg tttcctggat ccaataaatc    11880
taatcttcat gtagatctaa ttcttcaatc atgtccggca ggttcttcat tgggtagttg    11940
ttgtaaacga tttggtatac ggcttcaaat aatgggaagt cttcgacaga gccacatgtt    12000
tccaaccatt cgtgaacttc tttgcaggta attaaacctt gagcggattg gccattcaac    12060
aactcctttt cacattccca ggcgtcctta ccagaagtag ccattagcct agcaaccttg    12120
acgtttctac caccagcgca ggtggtgatc aaatcagcaa caccagcaga ctcttggtag    12180
tatgtttctt ctctagattc tgggaaaaac atttgaccga atctgatgat ctcacccaaa    12240
ccgactcttt ggatggcagc agaagcgttg ttaccccagc ctagaccttc gacgaaacca    12300
caacctaagg caacaacgtt cttcaaagca ccacagatgg agataccagc aacatcttcg    12360 atgcacactaa cgtggaagta aggtctgtgg aacaaggcct ttagaacctt atggtcgacg    12420
tccttgccct cgcctctgaa atcctttgga atgtggtaag caactgttgt ttcagaccag    12480
tgttcttgag cgacttcggt ggcaatgtta gcaccagata gagcaccaca ttgaataccct   12540 agttcctcag tgatgtaaga ggatagcaat tggacacctt tagcaccaac ttcaaaaccc    12600
tttagacagg agatagctct gacgtgtgaa tcaacatgac ctttcaattg gctacagata    12660
cggggcaaaa attgatgtgg aatgttgaaa acgatgatgt cgacatcctt gactgaatca    12720
atcaagtctg gattagcaac caaattgtcg ggtagagtga tgccaggcaa gtatttcacg    12780
ttttgatgtc tagtatttat gatttcagtc aattttttcac cattgatctc ttcttcgaac    12840
acccacattt gtactattgg agcgaaaact tctgggtatc ccttacaatt ttcggcaacc    12900
accttggcaa tagtagtacc ccagttacca gatccaatca cagtaacctt gaaaggcttt    12960
tcggcagcct tcaaagaaac agaagaggaa cttctctttc taccagcatt caagtggccg    13020
gaagttaagt ttaatctatc agcagcagca gccatggaat tgtcctcctt actagtcatg    13080 gtctgttttcc tgtgtgaaat tgttatccgc tcacaattcc acacattata cgagccggat    13140
gattaattgt caacagctca tttcagaata tttgccagaa ccgttatgat gtcggcgcaa    13200
aaaacattat ccagaacggg agtgcgcctt gagcgacacg aattatgcag tgatttacga    13260
cctgcacagc cataccacag cttccgatgg ctgcctgacg ccagaagcat tggtgcacgc    13320
tagccagtac atttaaatgg taccctctag tcaaggcctt aagtgagtcg tattacggac    13380
tggccgtcgt tttacaacgt cgtgactggg aaaaccctgg cgttacccaa cttaatcgcc    13440
ttgcagcaca tccccctttc gccagctggc gtaatagcga agaggcccgc accgatcgcc    13500
cttcccaaca gttgcgcagc ctgaatgcgc aatggcgcct gatgcggtat tttctcctta    13560
cgcatctgtg cggtatttca caccgcatat ggtgcactct cagtacaatc tgctctgatg    13620
ccgcatagtt aagccagccc cgacacccgc caacacccgc tgacgagct                13669
```

<210> SEQ ID NO 66
<211> LENGTH: 13543
<212> TYPE: DNA
<213> ORGANISM: artificial sequence
<220> FEATURE:
<223> OTHER INFORMATION: Plasmid pSYCO103

<400> SEQUENCE: 66

```
tagtaaagcc ctcgctagat tttaatgcgg atgttgcgat tacttcgcca actattgcga      60
taacaagaaa aagccagcct tcatgatat  atctcccaat tgtgtaggg  cttattatgc     120
acgcttaaaa ataataaaag cagacttgac ctgatagttt ggctgtgagc aattatgtgc     180
ttagtgcatc taacgcttga gttaagccgc gccgcgaagc ggcgtcggct tgaacgaatt     240
gttagacatt atttgccgac taccttggtg atctcgcctt tcacgtagtg acaaattct      300
tccaactgat ctgcgcgcga ggccaagcga tcttcttctt gtccaagata agcctgtcta     360
gcttcaagta tgacgggctg atactgggcc ggcaggcgct ccattgccca gtcggcagcg     420
acatccttcg gcgcgatttt gccggttact gcgctgtacc aaatgcggga caacgtaagc     480
actacatttc gctcatcgcc agcccagtcg ggcggcgagt tccatagcgt taaggttta     540
tttagcgcct caaatagatc ctgttcagga accggatcaa agagttcctc cgccgctgga     600
cctaccaagg caacgctatg ttctcttgct tttgtcagca agatagccag atcaatgtcg     660
atcgtggctg gctcgaagat acctgcaaga atgtcattgc gctgccattc tccaaattgc     720
agttcgcgct tagctggata cgccacggga atgatgtcgt cgtgcacaac aatggtgact     780
ctacagcgc  ggagaatctc gctctctcca ggggaagccg aagtttccaa aaggtcgttg     840
atcaaagctc gccgcgttgt ttcatcaagc cttacggtca ccgtaaccag caaatcaata     900
tcactgtgtg gcttcaggcc gccatccact gcggagccgt acaaatgtac ggccagcaac     960
gtcggttcga gatggcgctc gatgacgcca actacctctg atagttgagt cgatacttcg    1020
gcgatcaccg cttccctcat gatgtttaac tttgttttag gcgactgcc  ctgctgcgta    1080
acatcgttgc tgctccataa catcaaacat cgacccacgg cgtaacgcgc ttgctgcttg    1140
gatgcccgag gcatagactg taccccaaaa aaacagtcat aacaagccat gaaaaccgcc    1200
actgcgccgt taccaccgct gcgttcggtc aaggttctgg accagttgcg tgagcgcata    1260
cgctacttgc attacagctt acgaaccgaa caggcttatg tccactgggt tcgtgccttc    1320
atccgtttcc acggtgtgcg tcacccggca accttgggca gcagcgaagt cgaggcattt    1380
ctgtcctggc tggcgaacga gcgcaaggtt tcggtctcca cgcatcgtca ggcattggcg    1440
gccttgctgt tcttctacgg caaggtgctg tgcacggatc tgccctggct tcaggagatc    1500
ggaagacctc ggccgtcgcg gcgcttgccg gtggtgctga ccccggatga agtggttcgc    1560
atcctcggtt ttctggaagg cgagcatcgt ttgttcgccc agcttctgta tggaacgggc    1620
atgcggatca gtgagggttt gcaactgcgg gtcaaggatc tggatttcga tcacggcacg    1680
atcatcgtgc gggagggcaa gggctccaag gatcgggcct tgatgttacc cgagagcttg    1740
gcacccagcc tgcgcgagca ggggaattaa ttcccacggg ttttgctgcc cgcaaacggg    1800
ctgttctggt gttgctagtt tgttatcaga atcgcagatc cggcttcagc cggtttgccg    1860
gctgaaagcg ctatttcttc cagaattgcc atgattttt  ccccacggga ggcgtcactg    1920
gctcccgtgt tgtcggcagc tttgattcga taagcagcat cgcctgtttc aggctgtcta    1980
tgtgtgactg ttgagctgta acaagttgtc tcaggtgttc aatttcatgt tctagttgct    2040
ttgttttact ggtttcacct gttctattag gtgttacatg ctgttcatct gttacattgt    2100
```

```
cgatctgttc atggtgaaca gctttgaatg caccaaaaac tcgtaaaagc tctgatgtat   2160 ctatctttt  tacaccgttt tcatctgtgc atatggacag ttttcccttt gatatgtaac   2220
ggtgaacagt tgttctactt tgtttgtta gtcttgatgc ttcactgata gatacaagag    2280
ccataagaac ctcagatcct tccgtattta gccagtatgt tctctagtgt ggttcgttgt   2340
ttttgcgtga ccatgagaa cgaaccattg agatcatact tactttgcat gtcactcaaa    2400
aattttgcct caaaactggt gagctgaatt tttgcagtta aagcatcgtg tagtgttttt   2460
cttagtccgt tatgtaggta ggaatctgat gtaatggttg ttggtatttt gtcaccattc   2520 attttatct ggttgttctc aagttcggtt acgagatcca tttgtctatc tagttcaact    2580
tggaaaatca acgtatcagt cgggcggcct cgcttatcaa ccaccaattt catattgctg   2640
taagtgttta aatctttact tattggttc aaaacccatt ggttaagcct tttaaactca    2700
tggtagttat tttcaagcat taacatgaac ttaaattcat caaggctaat ctctatattt   2760
gccttgtgag ttttctttg tgttagtct tttaataacc actcataaat cctcatagag     2820
tatttgtttt caaaagactt aacatgttcc agattatatt ttatgaattt ttttaactgg   2880
aaaagataag gcaatatctc ttcactaaaa actaattcta atttttcgct tgagaacttg   2940
gcatagtttg tccactggaa aatctcaaag cctttaacca aaggattcct gatttccaca   3000
gttctcgtca tcagctctct ggttgcttta gctaatacac cataagcatt ttccctactg   3060
atgttcatca tctgagcgta ttggttataa gtgaacgata ccgtccgttc tttccttgta   3120
gggttttcaa tcgtggggtt gagtagtgcc acacagcata aaattagctt ggtttcatgc   3180
tccgttaagt catagcgact aatcgctagt tcatttgctt tgaaaacaac taattcagac   3240
atacatctca attggtctag gtgatttaa tcactatacc aattgagatg ggctagtcaa    3300
tgataattac tagtccttt cctttgagtt gtgggtatct gtaaattctg ctagaccttt    3360
gctgaaaaac ttgtaaattc tgctagaccc tctgtaaatt ccgctagacc tttgtgtgtt   3420
ttttttgttt atattcaagt ggttataatt tatagaataa agaaagaata aaaaaagata   3480 aaagaatag atcccagccc tgtgtataac tcactacttt agtcagttcc gcagtattac    3540
aaaaggatgt cgcaaacgct gtttgctcct ctacaaaaca gaccttaaaa ccctaaaggc   3600
ttaagtagca ccctcgcaag ctcgggcaaa tcgctgaata ttccttttgt ctccgaccat   3660
caggcacctg agtcgctgtc ttttcgtga cattcagttc gctgcgctca cggctctggc    3720
agtgaatggg ggtaaatggc actacaggcg cctttatgg attcatgcaa ggaaactacc    3780
cataatacaa gaaaagcccg tcacgggctt ctcagggcgt tttatggcgg gtctgctatg   3840
tggtgctatc tgacttttg ctgttcagca gttcctgccc tctgattttc cagtctgacc    3900
acttcggatt atcccgtgac aggtcattca gactggctaa tgcacccagt aaggcagcgg   3960
tatcatcaac aggcttaccc gtcttactgt cgggaattca tttaaatagt caaaagcctc   4020
cgaccggagg cttttgactg ctaggcgatc tgtgctgttt ccacggtat gcagcaccag    4080 cgcgagatta tgggctcgca cgctcgactg tcggacgggg gcactggaac gagaagtcag   4140
gcgagccgtc acgcccttga ctatgccaca tcctgagcaa ataattcaac cactaaacaa   4200
atcaaccgcg tttcccggag gtaaccaagc ttgcgggaga gaatgatgaa caagagccaa   4260
caagttcaga caatcaccct ggccgccgcc agcaaatgg cggcggcggt ggaaaaaaaa    4320
gccactgaga tcaacgtggc ggtggtgttt tccgtagttg accgcggagg caacacgctg   4380
cttatccagc ggatggacga ggccttcgtc tccagctgcg atatttccct gaataaagcc   4440
tggagcgcct gcagcctgaa gcaaggtacc catgaaatta cgtcagcggt ccagccagga   4500
```

```
caatctctgt acggtctgca gctaaccaac caacagcgaa ttattatttt tggcggcggc    4560
ctgccagtta tttttaatga gcaggtaatt ggcgccgtcg gcgttagcgg cggtacggtc    4620
gagcaggatc aattattagc ccagtgcgcc ctggattgtt tttccgcatt ataacctgaa    4680
gcgagaaggt atattatgag ctatcgtatg ttccgccagg cattctgagt gttaacgagg    4740
ggaccgtcat gtcgctttca ccgccaggcg tacgcctgtt ttacgatccg cgcgggcacc    4800
atgccggcgc catcaatgag ctgtgctggg gctggagga gcaggggtc ccctgccaga    4860
ccataaccta tgacggaggc ggtgacgccg ctgcgctggg cgccctggcg ccagaagct    4920
cgcccctgcg ggtgggtatc gggctcagcg cgtccggcga gatagccctc actcatgccc    4980
agctgccggc ggacgcgccg ctggctaccg gacacgtcac cgatagcgac gatcaactgc    5040
gtacgctcgg cgccaacgcc gggcagctgg ttaaagtcct gccgttaagt gagagaaact    5100
gaatgtatcg tatctatacc cgcaccgggg ataaaggcac caccgccctg tacggcggca    5160
gccgcatcga gaaagaccat attcgcgtcg aggcctacgg caccgtcgat gaactgatat    5220
cccagctggg cgtctgctac gccacgaccc gcgacgccgg gctgcgggaa agcctgcacc    5280
atattcagca gacgctgttc gtgctggggg ctgaactggc cagcgatgcg cggggcctga    5340
cccgcctgag ccagacgatc ggcgaagagg agatcaccgc cctggagcgg cttatcgacc    5400
gcaatatggc cgagagcggc ccgttaaaac agttcgtgat cccggggagg aatctcgcct    5460
ctgcccagct gcacgtggcg cgcacccagt cccgtcggct cgaacgcctg ctgacgccca    5520
tggaccgcgc gcatccgctg cgcgacgcgc tcaaacgcta cagcaatcgc ctgtcggatg    5580
ccctgttctc catggcgcga atcgaagaga ctaggcctga tgcttgcgct tgaactggcc    5640
tagcaaacac agaaaaaagc ccgcacctga cagtgcgggc tttttttttc ctaggcgatc    5700
tgtgctgttt gccacggtat gcagcaccag cgcgagatta tgggctcgca cgctcgactg    5760
tcggacgggg gcactggaac gagaagtcag gcgagccgtc acgcccttga ctatgccaca    5820
tcctgagcaa ataattcaac cactaaacaa atcaaccgcg tttccggag gtaaccaagc    5880
ttcacctttt gagccgatga acaatgaaaa gatcaaaacg atttgcagta ctggcccagc    5940
gccccgtcaa tcaggacggg ctgattggcg agtggcctga agaggggctg atcgccatgg    6000
acagccccttt tgacccggtc tcttcagtaa aagtggacaa cggtctgatc gtcgaactgg    6060
acggcaaacg ccgggaccag tttgacatga tcgaccgatt tatcgccgat tacgcgatca    6120
acgttgagcg cacagagcag gcaatgcgcc tggaggcggt ggaaatagcc cgtatgctgg    6180
tggatattca cgtcagccgg gaggagatca ttgccatcac taccgccatc acgccggcca    6240
aagcggtcga ggtgatggcg cagatgaacg tggtggagat gatgatgcg ctgcagaaga    6300
tgcgtgcccg ccggacccc tccaaccagt gccacgtcac caatctcaaa gataatccgg    6360
tgcagattgc cgctgacgcc gccgaggccg ggatccgcgg cttctcagaa caggagacca    6420
cggtcggtat cgcgcgctac gcgccgttta acgccctggc gctgttggtc ggttcgcagt    6480
gcggccgccc cggcgtgttg acgcagtgct cggtggaaga ggccaccgag ctggagctgg    6540
gcatgcgtgg cttaaccagc tacgccgaga cggtgtcggt ctacggcacc gaagcggtat    6600
ttaccgacgg cgatgatacg ccgtggtcaa aggcgttcct cgcctcggcc tacgcctccc    6660
gcgggttgaa aatgcgctac acctccggca ccggatccga agcgctgatg ggctattcgg    6720
agagcaagtc gatgctctac ctcgaatcgc gctgcatctt cattactaaa ggcgccgggg    6780
ttcagggact gcaaaacggc gcggtgagct gtatcggcat gaccggcgct gtgccgtcgg    6840
```

```
gcattcgggc ggtgctggcg gaaaacctga tcgcctctat gctcgacctc gaagtggcgt    6900
ccgccaacga ccagactttc tcccactcgg atattcgccg caccgcgcgc accctgatgc    6960
agatgctgcc gggcaccgac tttatttct ccggctacag cgcggtgccg aactacgaca     7020
acatgttcgc cggctcgaac ttcgatgcgg aagattttga tgattacaac atcctgcagc    7080
gtgacctgat ggttgacggc ggcctgcgtc cggtgaccga ggcggaaacc attgccattc    7140
gccagaaagc ggcgcgggcg atccaggcgg ttttccgcga gctggggctg ccgccaatcg    7200
ccgacgagga ggtggaggcc gccacctacg cgcacggcag caacgagatg ccgccgcgta    7260
acgtggtgga ggatctgagt gcggtggaag agatgatgaa gcgcaacatc accggcctcg    7320
atattgtcgg cgcgctgagc cgcagcggct ttgaggatat cgccagcaat attctcaata    7380
tgctgcgcca gcgggtcacc ggcgattacc tgcagacctc ggccattctc gatcggcagt    7440
tcgaggtggt gagtgcggtc aacgacatca atgactatca ggggccgggc accggctatc    7500
gcatctctgc cgaacgctgg gcggagatca aaatattcc gggcgtggtt cagcccgaca     7560
ccattgaata aggcggtatt cctgtgcaac agacaaccca aattcagccc tcttttaccc    7620
tgaaaacccg cgagggcggg gtagcttctg ccgatgaacg cgccgatgaa gtggtgatcg    7680
gcgtcggccc tgccttcgat aaacaccagc atcacactct gatcgatatg ccccatggcg    7740
cgatcctcaa agagctgatt gccggggtgg aagaagaggg gcttcacgcc cgggtggtgc    7800
gcattctgcg cacgtccgac gtctccttta tggcctggga tgcggccaac ctgagcggct    7860
cggggatcgg catcggtatc cagtcgaagg ggaccacggt catccatcag cgcgatctgc    7920
tgccgctcag caacctggag ctgttctccc aggcgccgct gctgacgctg gagacctacc    7980
ggcagattgg caaaaacgct gcgcgctatg cgcgcaaaga gtcaccttcg ccggtgccgg    8040
tggtgaacga tcagatggtg cggccgaaat ttatggccaa agccgcgcta tttcatatca    8100
aagagaccaa acatgtggtg caggacgccg agcccgtcac cctgcacatc gacttagtaa    8160
gggagtgacc atgagcgaga aaaccatgcg cgtgcaggat tatccgttag ccacccgctg    8220
cccggagcat atcctgacgc ctaccggcaa accattgacc gatattaccc tcgagaaggt    8280
gctctctggc gaggtgggcc gcaggatgt gcggatctcc cgccagaccc ttgagtacca     8340
ggcgcagatt gccgagcaga tgcagcgcca tgccgtggcg cgcaatttcc gccgcgcggc    8400
ggagcttatc gccattcctg acgagcgcat tctggctatc tataacgcgc tgcgcccgtt    8460
ccgctcctcg caggcggagc tgctggcgat cgccgacgag ctggagcaca cctggcatgc    8520
gacagtgaat gccgccttg tccgggagtc ggcggaagtg tatcagcagc ggcataagct     8580
gcgtaaagga agctaagcgg aggtcagcat gccgttaata gccgggattg atatcggcaa    8640
cgccaccacc gaggtggcgc tggcgtccga ctacccgcag gcgagggcgt ttgttgccag    8700
cgggatcgtc gcgacgacgg gcatgaaagg gacgcgggac aatatcgccg ggaccctcgc    8760
cgcgctggag caggccctgg cgaaaacacc gtggtcgatg agcgatgtct ctcgcatcta    8820
tcttaacgaa gccgcgccgg tgattggcga tgtggcgatg gagaccatca ccgagaccat    8880
tatcaccgaa tcgaccatga tcggtcataa cccgcagacg ccgggcgggg tgggcgttgg    8940
cgtggggacg actatcgccc tcgggcggct ggcgacgctg ccggcggcgc agtatgccga    9000
ggggtggatc gtactgattg acgacgccgt cgatttcctt gacgccgtgt ggtggctcaa    9060
tgaggcgctc gaccggggga tcaacgtggt ggcggcgatc ctcaaaaagg acgacggcgt    9120
gctggtgaac aaccgcctgc gtaaaaccct gccggtggtg gatgaagtga cgctgctgga    9180
gcaggtcccc gaggggtaa tggcggcggt ggaagtggcc gcgccgggcc aggtggtgcg     9240
```

```
gatcctgtcg aatccctacg ggatcgccac cttcttcggg ctaagcccgg aagagaccca    9300
ggccatcgtc cccatcgccc gcgccctgat tggcaaccgt tccgcggtgg tgctcaagac    9360
cccgcagggg gatgtgcagt cgcggtgat cccggcgggc aacctctaca ttagcggcga     9420
aaagcgccgc ggagaggccg atgtcgccga gggcgcggaa gccatcatgc aggcgatgag    9480
cgcctgcgct ccggtacgcg catccgcgg cgaaccgggc acccacgccg gcggcatgct     9540
tgagcgggtg cgcaaggtaa tggcgtccct gaccggccat gagatgagcg cgatatacat    9600
ccaggatctg ctggcggtgg atacgtttat tccgcgcaag gtgcagggcg ggatggccgg    9660
cgagtgcgcc atggagaatg ccgtcgggat ggcggcgatg gtgaaagcgg atcgtctgca    9720
aatgcaggtt atcgcccgcg aactgagcgc ccgactgcag accgaggtgg tggtgggcgg    9780
cgtggaggcc aacatggcca tcgccggggc gttaaccact cccggctgtg cggcgccgct    9840
ggcgatcctc gacctcggcg ccggctcgac ggatgcggcg atcgtcaacg cggaggggca    9900
gataacggcg gtccatctcg ccggggcggg gaatatggtc agcctgttga ttaaaaccga    9960
gctgggcctc gaggatcttt cgctggcgga agcgataaaa aaatacccgc tggccaaagt   10020
ggaaagcctg ttcagtattc gtcacgagaa tggcgcggtg gagttctttc gggaagcccT   10080
cagcccggcg gtgttcgcca aagtggtgta catcaaggag ggcgaactgg tgccgatcga   10140
taacgccagc ccgctggaaa aaattcgtct cgtgcgccgg caggcgaaag agaaagtgtt   10200
tgtcaccaac tgcctgcgcg cgctgcgcca ggtctcaccc ggcggttcca ttcgcgatat   10260
cgcctttgtg gtgctggtgg gcggctcatc gctggacttt gagatcccgc agcttatcac   10320
ggaagccttg tcgcactatg gcgtggtcgc cgggcagggc aatattcggg aacagaagg    10380
gccgcgcaat gcggtcgcca ccgggctgct actggccggt caggcgaatt aaacgggcgc   10440
tcgcgccagc ctctaggtac aaataaaaaa ggcacgtcag atgacgtgcc ttttttcttg   10500
tctagcgtgc accaatgctt ctggcgtcag gcagccatcg gaagctgtgg tatggctgtg   10560
caggtcgtaa atcactgcat aattcgtgtc gctcaaggcg cactcccgtt ctggataatg   10620
tttttttgcgc cgacatcata acggttctgg caaatattct gaaatgagct gttgacaatt   10680
aatcatccgg ctcgtataat gtgtggaatt gtgagcggat aacaatttca cacaggaaac   10740
agaccatgac tagtaaggag gacaattcca tggctgctgc tgctgataga ttaaacttaa   10800
cttccggcca cttgaatgct ggtagaaaga aagttcctc ttctgttcct ttgaaggctg    10860
ccgaaaagcc tttcaaggtt actgtgattg gatctggtaa ctgggtact actattgcca    10920
aggtggttgc cgaaaattgt aagggatacc cagaagtttt cgctccaata gtacaaatgt   10980
gggtgttcga agaagagatc aatggtgaaa aattgactga atcataaat actagacatc    11040
aaaacgtgaa atacttgcct ggcatcactc tacccgacaa tttggttgct aatccagact   11100
tgattgattc agtcaaggat gtcgacatca tcgtttttcaa cattccacat caattttttgc  11160
cccgtatctg tagccaattg aaaggtcatg ttgattcaca cgtcagagct atctcctgtc   11220
taaagggttt tgaagttggt gctaaaggtg tccaattgct atcctcttac atcactgagg   11280
aactaggtat tcaatgtggt gctctatctg gtgctaacat tgccaccgaa gtcgctcaag   11340
aacactggtc tgaaacaaca gttgcttacc acattccaaa ggatttcaga ggcgagggca   11400
aggacgtcga ccataaggtt ctaaaggcct tgttccacag accttacttc cacgttagtg   11460
tcatcgaaga tgttgctggt atctccatct gtggtgcttt gaagaacgtt gttgccttag   11520
gttgtggttt cgtcgaaggt ctaggctggg gtaacaacgc ttctgctgcc atccaaagag   11580
```

```
tcggtttggg tgagatcatc agattcggtc aaatgttttt cccagaatct agagaagaaa    11640
catactacca agagtctgct ggtgttgctg atttgatcac cacctgcgct ggtggtagaa    11700
acgtcaaggt tgctaggcta atggctactt ctggtaagga cgcctgggaa tgtgaaaagg    11760
agttgttgaa tggccaatcc gctcaaggtt taattacctg caaagaagtt cacgaatggt    11820
tggaaacatg tggctctgtc gaagacttcc cattatttga agccgtatac caaatcgttt    11880
acaacaacta cccaatgaag aacctgccgg acatgattga agaattagat ctacatgaag    11940
attagattta ttggatccag gaaacagact agaattatgg gattgactac taaacctcta    12000
tctttgaaag ttaacgccgc tttgttcgac gtcgacggta ccattatcat ctctcaacca    12060
gccattgctg cattctggag ggatttcggt aaggacaaac cttatttcga tgctgaacac    12120
gttatccaag tctcgcatgg ttggagaacg tttgatgcca ttgctaagtt cgctccagac    12180
tttgccaatg aagagtatgt taacaaatta aagctgaaa ttccggtcaa gtacggtgaa    12240
aaatccattg aagtcccagg tgcagttaag ctgtgcaacg ctttgaacgc tctaccaaaa    12300
gagaaatggg ctgtggcaac ttccggtacc cgtgatatgg cacaaaaatg gttcgagcat    12360
ctgggaatca ggagaccaaa gtacttcatt accgctaatg atgtcaaaca gggtaagcct    12420
catccagaac catatctgaa gggcaggaat ggcttaggat atccgatcaa tgagcaagac    12480
ccttccaaat ctaaggtagt agtatttgaa gacgctccag caggtattgc cgccggaaaa    12540
gccgccggtt gtaagatcat tggtattgcc actactttcg acttggactt cctaaaggaa    12600
aaaggctgtg acatcattgt caaaaaccac gaatccatca gagttggcgg ctacaatgcc    12660
gaaacagacg aagttgaatt cattttttgac gactacttat atgctaagga cgatctgttg    12720
aaatggtaac ccgggctgca ggcatgcaag cttggctgtt ttggcggatg agagaagatt    12780
ttcagcctga tacagattaa atcagaacgc agaagcggtc tgataaaaca gaatttgcct    12840
ggcggcagta gcgcggtggt cccacctgac cccatgccga actcagaagt gaaacgccgt    12900
agcgccgatg gtagtgtggg gtctccccat gcgagagtag ggaactgcca ggcatcaaat    12960
aaaacgaaag gctcagtcga aagactgggc ctttcgtttt atctgttgtt tgtcggtgaa    13020
cgctctcctg agtaggacaa atccgccggg agcggatttg aacgttgcga agcaacggcc    13080
cggagggtgg cgggcaggac gcccgccata aactgccagg catcaaatta gcagaaggc    13140
catcctgacg gatggccttt ttgcgtttct acaaactcca gctggatcgg cgctagagt    13200
atacatttaa atggtaccct ctagtcaagg ccttaagtga gtcgtattac ggactggccg    13260
tcgttttaca acgtcgtgac tgggaaaacc ctggcgttac ccaacttaat cgccttgcag    13320
cacatccccc tttcgccagc tggcgtaata gcgaagaggc ccgcaccgat cgccttccc    13380
aacagttgcg cagcctgaat ggcgaatggc gcctgatgcg gtattttctc cttacgcatc    13440
tgtgcggtat ttcacaccgc atatggtgca ctctcagtac aatctgctct gatgccgcat    13500
agttaagcca gccccgacac ccgccaacac ccgctgacga gct                     13543
```

<210> SEQ ID NO 67
<211> LENGTH: 13543
<212> TYPE: DNA
<213> ORGANISM: Artificial sequence
<220> FEATURE:
<223> OTHER INFORMATION: Plasmid pSYCO106

<400> SEQUENCE: 67

```
tagtaaagcc ctcgctagat tttaatgcgg atgttgcgat tacttcgcca actattgcga      60
taacaagaaa aagccagcct ttcatgatat atctcccaat ttgtgtaggg cttattatgc     120
```

-continued

| | |
|---|---|
| acgcttaaaa ataataaaag cagacttgac ctgatagttt ggctgtgagc aattatgtgc | 180 |
| ttagtgcatc taacgcttga gttaagccgc gccgcgaagc ggcgtcggct tgaacgaatt | 240 |
| gttagacatt atttgccgac taccttggtg atctcgcctt tcacgtagtg gacaaattct | 300 |
| tccaactgat ctgcgcgcga ggccaagcga tcttcttctt gtccaagata agcctgtcta | 360 |
| gcttcaagta tgacgggctg atactgggcc ggcaggcgct ccattgccca gtcggcagcg | 420 |
| acatccttcg gcgcgatttt gccggttact gcgctgtacc aaatgcggga caacgtaagc | 480 |
| actacatttc gctcatcgcc agcccagtcg ggcggcgagt tccatagcgt taaggtttca | 540 |
| tttagcgcct caaatagatc ctgttcagga accggatcaa agagttcctc cgccgctgga | 600 |
| cctaccaagg caacgctatg ttctcttgct tttgtcagca agatagccag atcaatgtcg | 660 |
| atcgtggctg gctcgaagat acctgcaaga atgtcattgc gctgccattc tccaaattgc | 720 |
| agttcgcgct tagctggata cgccacggaa tgatgtcgt cgtgcacaac aatggtgact | 780 |
| tctacagcgc ggagaatctc gctctctcca ggggaagccg aagtttccaa aaggtcgttg | 840 |
| atcaaagctc gccgcgttgt tcatcaagc cttacggtca ccgtaaccag caatcaata | 900 |
| tcactgtgtg gcttcaggcc gccatccact gcggagccgt acaaatgtac ggccagcaac | 960 |
| gtcggttcga gatggcgctc gatgacgcca actacctctg atagttgagt cgatacttcg | 1020 |
| gcgatcaccg cttccctcat gatgtttaac tttgttttag ggcgactgcc ctgctgcgta | 1080 |
| acatcgttgc tgctccataa catcaaacat cgacccacgg cgtaacgcgc ttgctgcttg | 1140 |
| gatgcccgag gcatagactg tacccccaaaa aaacagtcat aacaagccat gaaaaccgcc | 1200 |
| actgcgccgt taccaccgct gcgttcggtc aaggttctgg accagttgcg tgagcgcata | 1260 |
| cgctacttgc attacagctt acgaaccgaa caggcttatg tccactgggt tcgtgccttc | 1320 |
| atccgtttcc acggtgtgcg tcacccggca accttgggca gcagcgaagt cgaggcattt | 1380 |
| ctgtcctggc tggcgaacga gcgcaaggtt tcggtctcca cgcatcgtca ggcattggcg | 1440 |
| gccttgctgt tcttctacgg caaggtgctg tgcacggatc tgccctggct tcaggagatc | 1500 |
| ggaagacctc ggccgtcgcg gcgcttgccg gtggtgctga ccccggatga agtggttcgc | 1560 |
| atcctcggtt ttctggaagg cgagcatcgt ttgttcgccc agcttctgta tggaacgggc | 1620 |
| atgcggatca gtgagggttt gcaactgcgg gtcaaggatc tggatttcga tcacggcacg | 1680 |
| atcatcgtgc gggagggcaa gggctccaag gatcgggcct tgatgttacc cgagagcttg | 1740 |
| gcacccagcc tgcgcgagca ggggaattaa ttcccacggg ttttgctgcc cgcaaacggg | 1800 |
| ctgttctggt gttgctagtt tgttatcaga atcgcagatc cggcttcagc cggtttgccg | 1860 |
| gctgaaagcg ctatttcttc cagaattgcc atgattttt ccccacggga ggcgtcactg | 1920 |
| gctcccgtgt tgtcggcagc tttgattcga taagcagcat cgcctgtttc aggctgtcta | 1980 |
| tgtgtgactt tgagctgta acaagttgtc tcaggtgttc aatttcatgt tctagttgct | 2040 |
| ttgtttact ggtttcacct gttctattag gtgttacatg ctgttcatct gttacattgt | 2100 |
| cgatctgttc atggtgaaca gctttgaatg caccaaaaac tcgtaaaagc tctgatgtat | 2160 |
| ctatcttttt tacaccgttt tcatctgtgc atatggacag ttttcccttt gatatgtaac | 2220 |
| ggtgaacagt tgttctactt tgttttgtta gtcttgatgc ttcactgata gatacaagag | 2280 |
| ccataagaac ctcagatcct tccgtattta gccagtatgt tctctagtgt ggttcgttgt | 2340 |
| ttttgcgtga gccatgagaa cgaaccattg agatcatact tactttgcat gtcactcaaa | 2400 |
| aattttgcct caaaactggt gagctgaatt tttgcagtta aagcatcgtg tagtgttttt | 2460 |

```
cttagtccgt tatgtaggta ggaatctgat gtaatggttg ttggtatttt gtcaccattc    2520 attttatct ggttgttctc aagttcggtt acgagatcca tttgtctatc tagttcaact     2580
tggaaaatca acgtatcagt cgggcggcct cgcttatcaa ccaccaattt catattgctg    2640
taagtgttta aatctttact tattggtttc aaaacccatt ggttaagcct tttaaactca    2700
tggtagttat tttcaagcat taacatgaac ttaaattcat caaggctaat ctctatattt    2760
gccttgtgag ttttcttttg tgttagttct tttaataacc actcataaat cctcatagag    2820
tatttgtttt caaaagactt aacatgttcc agattatatt ttatgaattt ttttaactgg    2880
aaaagataag gcaatatctc ttcactaaaa actaattcta attttcgct tgagaacttg     2940 gcatagtttg tccactggaa aatctcaaag cctttaacca aaggattcct gatttccaca    3000
gttctcgtca tcagctctct ggttgcttta gctaatacac cataagcatt ttccctactg    3060
atgttcatca tctgagcgta ttggttataa gtgaacgata ccgtccgttc tttccttgta    3120
gggttttcaa tcgtggggtt gagtagtgcc acacagcata aaattagctt ggtttcatgc    3180
tccgttaagt catagcgact aatcgctagt tcatttgctt tgaaaacaac taattcagac    3240
atacatctca attggtctag gtgattttaa tcactatacc aattgagatg gctagtcaa     3300 tgataattac tagtcctttt cctttgagtt gtgggtatct gtaaattctg ctagaccttt    3360
gctggaaaac ttgtaaattc tgctagaccc tctgtaaatt ccgctagacc tttgtgtgtt    3420
ttttttgttt atattcaagt ggttataatt tatagaataa agaaagaata aaaaaagata    3480 aaagaatag atcccagccc tgtgtataac tcactacttt agtcagttcc gcagtattac     3540
aaaaggatgt cgcaaacgct gtttgctcct ctacaaaaca gaccttaaaa ccctaaaggc    3600
ttaagtagca ccctcgcaag ctcgggcaaa tcgctgaata ttccttttgt ctccgaccat    3660
caggcacctg agtcgctgtc ttttcgtga cattcagttc gctgcgctca cggctctggc    3720
agtgaatggg ggtaaatggc actacaggcg ccttttatgg attcatgcaa ggaaactacc    3780
cataatacaa gaaaagcccg tcacgggctt ctcagggcgt tttatggcgg gtctgctatg    3840
tggtgctatc tgacttttg ctgttcagca gttcctgccc tctgatttc cagtctgacc      3900 acttcggatt atcccgtgac aggtcattca gactggctaa tgcacccagt aaggcagcgg    3960
tatcatcaac aggcttaccc gtcttactgt cgggaattca tttaaatagt caaaagcctc    4020
cgaccggagg cttttgactg ctaggcgatc tgtgctgttt gccacggtat gcagcaccag    4080
cgcgagatta tgggctcgca cgctcgactg tcggacgggg gcactggaac gagaagtcag    4140
gcgagccgtc acgcccttga caatgccaca tcctgagcaa ataattcaac cactaaacaa    4200
atcaaccgcg tttcccggag gtaaccaagc ttgcgggaga gaatgatgaa caagagccaa    4260
caagttcaga caatcaccct ggccgccgcc cagcaaatgg cggcggcggt ggaaaaaaaa    4320
gccactgaga tcaacgtggc ggtggtgttt tccgtagttg accgcggagg caacacgctg    4380
cttatccagc ggatggacga ggccttcgtc tccagctgcg atatttccct gaataaagcc    4440
tggagcgcct gcagcctgaa gcaaggtacc catgaaatta cgtcagcggt ccagccagga    4500
caatctctgt acggtctgca gctaaccaac caacagcgaa ttattatttt tggcggcggc    4560
ctgccagtta ttttaatga gcaggtaatt ggcgccgtcg gcgttagcgg cggtacggtc     4620
gagcaggatc aattattagc ccagtgcgcc ctggattgtt tttccgcatt ataacctgaa    4680
gcgagaaggt atattatgag ctatcgtatg ttccgccagg cattctgagt gttaacgagg    4740
ggaccgtcat gtcgctttca ccgccaggcg tacgcctgtt ttacgatccg cgcgggcacc    4800
atgccggcgc catcaatgag ctgtgctggg gctggaggag gcaggggtc ccctgccaga    4860
```

```
ccataaccta tgacggaggc ggtgacgccg ctgcgctggg cgccctggcg gccagaagct    4920 cgccctgcg ggtgggtatc gggctcagcg cgtccggcga gatagccctc actcatgccc    4980
agctgccggc ggacgcgccg ctggctaccg gacacgtcac cgatagcgac gatcaactgc    5040
gtacgctcgg cgccaacgcc gggcagctgg ttaaagtcct gccgttaagt gagagaaact    5100
gaatgtatcg tatctatacc cgcaccgggg ataaaggcac caccgccctg tacgcggca     5160 gccgcatcga gaaagaccat attcgcgtcg aggcctacgg caccgtcgat gaactgatat    5220
cccagctggg cgtctgctac gccacgaccc gcgacgccgg gctgcgggaa agcctgcacc    5280
atattcagca gacgctgttc gtgctggggg ctgaactggc cagcgatgcg cggggcctga    5340
cccgcctgag ccagacgatc ggcgaagagg agatcaccgc cctggagcgg cttatcgacc    5400
gcaatatggc cgagagcggc ccgttaaaac agttcgtgat cccggggagg aatctcgcct    5460
ctgcccagct gcacgtggcg cgcacccagt cccgtcggct cgaacgcctg ctgacggcca    5520
tggaccgcgc gcatccgctg cgcgacgcgc tcaaacgcta cagcaatcgc ctgtcggatg    5580
ccctgttctc catggcgcga atcgaagaga ctaggcctga tgcttgcgct tgaactggcc    5640
tagcaaacac agaaaaaagc ccgcacctga cagtgcgggc ttttttttc ctaggcgatc     5700 tgtgctgttt gccacggtat gcagcaccag cgcgagatta tgggctcgca cgctcgactg    5760
tcggacgggg gcactggaac gagaagtcag gcgagccgtc acgcccttga caatgccaca    5820
tcctgagcaa ataattcaac cactaaacaa atcaaccgcg tttcccggag gtaaccaagc    5880
ttcacctttt gagccgatga acaatgaaaa gatcaaaacg atttgcagta ctggcccagc    5940
gccccgtcaa tcaggacggg ctgattggcg agtggcctga agaggggctg atcgccatgg    6000
acagcccctt tgacccggtc tcttcagtaa aagtggacaa cggtctgatc gtcgaactgg    6060
acggcaaacg ccgggaccag tttgacatga tcgaccgatt tatcgccgat tacgcgatca    6120
acgttgagcg cacagagcag gcaatgcgcc tggaggcggt ggaaatagcc cgtatgctgg    6180
tggatattca cgtcagccgg gaggagatca ttgccatcac taccgccatc acgccggcca    6240
aagcggtcga ggtgatggcg cagatgaacg tggtggagat gatgatgcg ctgcagaaga     6300 tgcgtgcccg ccggaccccc tccaaccagt gccacgtcac caatctcaaa gataatccgg    6360
tgcagattgc cgctgacgcc gccgaggccg ggatccgcgg cttctcagaa caggagacca    6420
cggtcggtat cgcgcgctac gcgccgttta acgccctggc gctgttggtc ggttcgcagt    6480
gcggccgccc cggcgtgttg acgcagtgct cggtggaaga ggccaccgag ctggagctgg    6540
gcatgcgtgg cttaaccagc tacgccgaga cggtgtcggt ctacggcacc gaagcggtat    6600
ttaccgacgg cgatgatacg ccgtggtcaa aggcgttcct cgcctcggcc tacgcctccc    6660
gcgggttgaa aatgcgctac acctccggca ccggatccga agcgctgatg ggctattcgg    6720
agagcaagtc gatgctctac ctcgaatcgc gctgcatctt cattactaaa ggcgccgggg    6780
ttcagggact gcaaaacggc gcggtgagct gtatcggcat gaccggcgct gtgccgtcgg    6840
gcattcgggc ggtgctggcg gaaaacctga tcgcctctat gctcgacctc gaagtggcgt    6900
ccgccaacga ccagactttc tcccactcgg atattcgccg caccgcgcgc accctgatgc    6960
agatgctgcc gggcaccgac tttatttct ccggctacag cgcggtgccg aactacgaca     7020
acatgttcgc cggctcgaac ttcgatgcgg aagatttga tgattacaac atcctgcagc     7080
gtgacctgat ggttgacggc ggcctgcgtc cggtgaccga ggcggaaacc attgccattc    7140
gccagaaagc ggcgcgggcg atccaggcgg tttccgcga gctggggctg ccgccaatcg     7200
```

```
ccgacgagga ggtggaggcc gccacctacg cgcacggcag caacgagatg ccgccgcgta    7260
acgtggtgga ggatctgagt gcggtggaag agatgatgaa gcgcaacatc accggcctcg    7320
atattgtcgg cgcgctgagc cgcagcggct tgaggatat cgccagcaat attctcaata    7380
tgctgcgcca gcgggtcacc ggcgattacc tgcagacctc ggccattctc gatcggcagt    7440
tcgaggtggt gagtgcggtc aacgacatca atgactatca ggggccgggc accggctatc    7500
gcatctctgc cgaacgctgg gcggagatca aaaatattcc gggcgtggtt cagcccgaca    7560
ccattgaata aggcggtatt cctgtgcaac agacaaccca aattcagccc tcttttaccc    7620
tgaaacccg cgagggcggg gtagcttctg ccgatgaacg cgccgatgaa gtggtgatcg    7680
gcgtcggccc tgccttcgat aaacaccagc atcacactct gatcgatatg ccccatggcg    7740
cgatcctcaa agagctgatt gccggggtgg aagaagaggg gcttcacgcc cgggtggtgc    7800
gcattctgcg cacgtccgac gtctcctta tggcctggga tgcggccaac ctgagcggct    7860
cggggatcgg catcggtatc cagtcgaagg ggaccacggt catccatcag cgcgatctgc    7920
tgccgctcag caacctggag ctgttctccc aggcgccgct gctgacgctg agacctacc    7980
ggcagattgg caaaaacgct gcgcgctatg cgcgcaaaga gtcaccttcg ccggtgccgg    8040
tggtgaacga tcagatggtg cggccgaaat ttatggccaa agccgcgcta tttcatatca    8100
aagagaccaa acatgtggtg caggacgccg agcccgtcac cctgcacatc gacttagtaa    8160
gggagtgacc atgagcgaga aaaccatgcg cgtgcaggat tatccgttag ccacccgctg    8220
cccggagcat atcctgacgc ctaccggcaa accattgacc gatattaccc tcgagaaggt    8280
gctctctggc gaggtgggcc cgcaggatgt gcggatctcc cgccagaccc ttgagtacca    8340
ggcgcagatt gccgagcaga tgcagcgcca tgccgtggcg cgcaatttcc gccgcgcggc    8400
ggagcttatc gccattcctg acgagcgcat tctggctatc tataacgcgc tgcgcccgtt    8460
ccgctcctcg caggcggagc tgctggcgat cgccgacgag ctggagcaca cctggcatgc    8520
gacagtgaat gccgcctttg tccgggagtc ggcggaagtg tatcagcagc ggcataagct    8580
gcgtaaagga agctaagcgg aggtcagcat gccgttaata gccgggattg atatcggcaa    8640
cgccaccacc gaggtggcgc tggcgtccga ctacccgcag gcgagggcgt tgttgccag    8700
cgggatcgtc gcgacgacgg gcatgaaagg gacgcgggac aatatcgccg ggaccctcgc    8760
cgcgctggag caggccctgg cgaaaacacc gtggtcgatg agcgatgtct ctcgcatcta    8820
tcttaacgaa gccgcgccgg tgattggcga tgtggcgatg gagaccatca ccgagaccat    8880
tatcaccgaa tcgaccatga tcggtcataa cccgcagacg ccggggcggg tgggcgttgg    8940
cgtggggacg actatcgccc tcgggcggct ggcgacgctg ccggcggcgc agtatgccga    9000
ggggtggatc gtactgattg acgacgccgt cgatttcctt gacgccgtgt ggtggctcaa    9060
tgaggcgctc gaccggggga tcaacgtggt ggcggcgatc ctcaaaaagg acgacggcgt    9120
gctggtgaac aaccgcctgc gtaaaaccct gccggtggtg gatgaagtga cgctgctgga    9180
gcaggtcccc gagggggtaa tggcggcggt ggaagtggcc gcgccgggcc aggtggtgcg    9240
gatcctgtcg aatccctacg ggatcgccac cttcttcggg ctaagcccgg aagagaccca    9300
ggccatcgtc cccatcgccc gcgccctgat tggcaaccgt tccgcggtgg tgctcaagac    9360
cccgcagggg gatgtgcagt gcgggtgat cccggcgggc aacctctaca ttagcggcga    9420
aaagcgccgc ggagaggccg atgtcgccga gggcgcggaa gccatcatgc aggcgatgag    9480
cgcctgcgct ccggtacgcg acatccgcgg cgaaccgggc acccacgccg gcggcatgct    9540
tgagcgggtg cgcaaggtaa tggcgtccct gaccggccat gagatgagcg cgatatacat    9600
```

```
ccaggatctg ctggcggtgg atacgtttat tccgcgcaag gtgcagggcg ggatggccgg   9660
cgagtgcgcc atggagaatg ccgtcgggat ggcggcgatg gtgaaagcgg atcgtctgca   9720
aatgcaggtt atcgcccgcg aactgagcgc ccgactgcag accgaggtgg tggtgggcgg   9780
cgtggaggcc aacatggcca tcgccggggc gttaaccact cccggctgtg cggcgccgct   9840
ggcgatcctc gacctcggcg ccggctcgac ggatgcggcg atcgtcaacg cggaggggca   9900
gataacggcg gtccatctcg ccggggcggg gaatatggtc agcctgttga ttaaaaccga   9960
gctgggcctc gaggatcttt cgctggcgga agcgataaaa aaatacccgc tggccaaagt  10020
ggaaagcctg ttcagtattc gtcacgagaa tggcgcggtg gagttctttc gggaagccct  10080
cagcccggcg gtgttcgcca agtggtgta catcaaggag ggcgaactgg tgccgatcga  10140
taacgccagc ccgctggaaa aaattcgtct cgtgcgccgg caggcgaaag agaaagtgtt  10200
tgtcaccaac tgcctgcgcg cgctgcgcca ggtctcaccc ggcggttcca ttcgcgatat  10260
cgcctttgtg gtgctggtgg gcggctcatc gctggacttt gagatcccgc agcttatcac  10320
ggaagccttg tcgcactatg gcgtggtcgc cgggcagggc aatattcggg aacagaagg  10380 gccgcgcaat gcggtcgcca ccgggctgct actggccggt caggcgaatt aaacgggcgc  10440
tcgcgccagc tctaggtac aaataaaaaa ggcacgtcag atgacgtgcc tttttcttg  10500 tctagcgtgc accaatgctt ctggcgtcag gcagccatcg gaagctgtgg tatggctgtg  10560
caggtcgtaa atcactgcat aattcgtgtc gctcaaggcg cactcccgtt ctggataatg  10620 tttttttgcgc cgacatcata acggttctgg caaatattct gaaatgagct gttgacaatt  10680
aatcatccgg ctcgtataat gtgtggaatt gtgagcggat aacaatttca cacaggaaac  10740
agaccatgac tagtaaggag gacaattcca tggctgctgc tgctgataga ttaaacttaa  10800
cttccggcca cttgaatgct ggtagaaaga gaagttcctc ttctgtttct ttgaaggctg  10860
ccgaaaagcc tttcaaggtt actgtgattg gatctggtaa ctggggtact actattgcca  10920
aggtggttgc cgaaaattgt aagggatacc agaagttttt cgctccaata gtacaaatgt  10980
gggtgttcga gaagagatc aatggtgaaa aattgactga atcataaat actagacatc  11040 aaaacgtgaa atacttgcct ggcatcactc tacccgacaa tttggttgct aatccagact  11100
tgattgattc agtcaaggat gtcgacatca tcgtttttca cattccacat caattttgc  11160 cccgtatctg tagccaattg aaaggtcatg ttgattcaca cgtcagagct atctcctgtc  11220
taaagggttt tgaagttggt gctaaaggtg tccaattgct atcctcttac atcactgagg  11280
aactaggtat tcaatgtggt gctctatctg gtgctaacat tgccaccgaa gtcgctcaag  11340
aacactggtc tgaaacaaca gttgcttacc acattccaaa ggatttcaga ggcgagggca  11400
aggacgtcga ccataaggtt ctaaaggcct tgttccacag accttacttc cacgttagtg  11460
tcatcgaaga tgttgctggt atctccatct gtggtgcttt gaagaacgtt gttgccttag  11520
gttgtggttt cgtcgaaggt ctaggctggg gtaacaacgc ttctgctgcc atccaaagag  11580
tcggtttggg tgagatcatc agattcggtc aaatgtttt cccagaatct agagaagaaa  11640
catactacca agagtctgct ggtgttgctg atttgatcac cacctgcgct ggtggtagaa  11700
acgtcaaggt tgctaggcta atggctactt ctggtaagga cgcctgggaa tgtgaaaagg  11760
agttgttgaa tggccaatcc gctcaaggtt taattacctg caaagaagtt cacgaatggt  11820
tggaaacatg tggctctgtc gaagacttcc cattatttga agccgtatac caaatcgttt  11880
acaacaacta cccaatgaag aacctgccgg acatgattga agaattagat ctacatgaag  11940
```

```
attagattta ttggatccag gaaacagact agaattatgg gattgactac taaacctcta   12000
tctttgaaag ttaacgccgc tttgttcgac gtcgacggta ccattatcat ctctcaacca   12060
gccattgctg cattctggag ggatttcggt aaggacaaac cttatttcga tgctgaacac   12120
gttatccaag tctcgcatgg ttggagaacg tttgatgcca ttgctaagtt cgctccagac   12180
tttgccaatg aagagtatgt taacaaatta gaagctgaaa ttccggtcaa gtacggtgaa   12240
aaatccattg aagtcccagg tgcagttaag ctgtgcaacg ctttgaacgc tctaccaaaa   12300
gagaaatggg ctgtggcaac ttccggtacc cgtgatatgg cacaaaaatg gttcgagcat   12360
ctgggaatca ggagaccaaa gtacttcatt accgctaatg atgtcaaaca gggtaagcct   12420
catccagaac catatctgaa gggcaggaat ggcttaggat atccgatcaa tgagcaagac   12480
ccttccaaat ctaaggtagt agtatttgaa gacgctccag caggtattgc cgccggaaaa   12540
gccgccggtt gtaagatcat tggtattgcc actactttcg acttggactt cctaaaggaa   12600
aaaggctgtg acatcattgt caaaaaccac gaatccatca gagttggcgg ctacaatgcc   12660
gaaacagacg aagttgaatt cattttttgac gactacttat atgctaagga cgatctgttg   12720
aaatggtaac ccgggctgca ggcatgcaag cttggctgtt ttggcggatg agagaagatt   12780
ttcagcctga tacagattaa atcagaacgc agaagcggtc tgataaaaca gaatttgcct   12840
ggcggcagta gcgcggtggt cccacctgac cccatgccga actcagaagt gaaacgccgt   12900
agcgccgatg gtagtgtggg gtctccccat gcgagagtag ggaactgcca ggcatcaaat   12960
aaaacgaaag gctcagtcga aagactgggc ctttcgtttt atctgttgtt tgtcggtgaa   13020
cgctctcctg agtaggacaa atccgccggg agcggatttg aacgttgcga agcaacggcc   13080
cggagggtgg cgggcaggac gcccgccata aactgccagg catcaaatta gcagaaggc   13140 catcctgacg gatggccttt tgcgtttct acaaactcca gctggatcgg cgctagagt   13200 atacatttaa atggtaccct ctagtcaagg ccttaagtga gtcgtattac ggactggccg   13260
tcgttttaca acgtcgtgac tgggaaaacc ctggcgttac ccaacttaat cgccttgcag   13320
cacatccccc tttcgccagc tggcgtaata gcgaagaggc ccgcaccgat cgcccttccc   13380
aacagttgcg cagcctgaat ggcgaatggc gcctgatgcg gtattttctc cttacgcatc   13440
tgtgcggtat ttcacaccgc atatggtgca ctctcagtac aatctgctct gatgccgcat   13500
agttaagcca gccccgacac ccgccaacac ccgctgacga gct                    13543
```

<210> SEQ ID NO 68
<211> LENGTH: 13402
<212> TYPE: DNA
<213> ORGANISM: Artificial sequence
<220> FEATURE:
<223> OTHER INFORMATION: Plasmid pSYCO109

<400> SEQUENCE: 68

```
tagtaaagcc ctcgctagat tttaatgcgg atgttgcgat tacttcgcca actattgcga    60
taacaagaaa aagccagcct ttcatgatat atctcccaat ttgtgtaggg cttattatgc   120
acgcttaaaa ataataaaag cagacttgac ctgatagttt ggctgtgagc aattatgtgc   180
ttagtgcatc taacgcttga gttaagccgc gccgcgaagc ggcgtcggct tgaacgaatt   240
gttagacatt atttgccgac taccttggtg atctcgcctt tcacgtagtg gacaaattct   300
tccaactgat ctgcgcgcga ggccaagcga tcttcttctt gtccaagata agcctgtcta   360
gcttcaagta tgacgggctg atactgggcc ggcaggcgct ccattgccca gtcggcagcg   420
acatccttcg gcgcgatttt gccggttact gcgctgtacc aaatgcggga caacgtaagc   480
```

```
actacatttc gctcatcgcc agcccagtcg ggcggcgagt tccatagcgt taaggtttca    540
tttagcgcct caaatagatc ctgttcagga accggatcaa agagttcctc cgccgctgga    600
cctaccaagg caacgctatg ttctcttgct tttgtcagca agatagccag atcaatgtcg    660
atcgtggctg gctcgaagat acctgcaaga atgtcattgc gctgccattc tccaaattgc    720
agttcgcgct tagctggata cgccacggaa atgatgtcgt cgtgcacaac aatggtgact    780
tctacagcgc ggagaatctc gctctctcca ggggaagccg aagtttccaa aaggtcgttg    840
atcaaagctc gccgcgttgt ttcatcaagc cttacggtca ccgtaaccag caaatcaata    900
tcactgtgtg gcttcaggcc gccatccact gcggagccgt acaaatgtac ggccagcaac    960
gtcggttcga gatggcgctc gatgacgcca actacctctg atagttgagt cgatacttcg   1020
gcgatcaccg cttccctcat gatgtttaac tttgttttag ggcgactgcc ctgctgcgta   1080
acatcgttgc tgctccataa catcaaacat cgacccacgg cgtaacgcgc ttgctgcttg   1140
gatgcccgag gcatagactg tacccccaaa aaacagtcat aacaagccat gaaaaccgcc   1200
actgcgccgt taccaccgct gcgttcggtc aaggttctgg accagttgcg tgagcgcata   1260
cgctacttgc attacagctt acgaaccgaa caggcttatg tccactgggt tcgtgccttc   1320
atccgttttcc acggtgtgcg tcacccggca accttgggca gcagcgaagt cgaggcattt   1380
ctgtcctggc tggcgaacga gcgcaaggtt tcggtctcca cgcatcgtca ggcattggcg   1440
gccttgctgt tcttctacgg caaggtgctg tgcacggatc tgccctggct tcaggagatc   1500
ggaagacctc ggccgtcgcg gcgcttgccg gtggtgctga ccccgatgaa gtggttcgc    1560
atcctcggtt ttctggaagg cgagcatcgt ttgttcgccc agcttctgta tggaacgggc   1620
atgcggatca gtgagggttt gcaactgcgg gtcaaggatc tggatttcga tcacggcacg   1680
atcatcgtgc gggagggcaa gggctccaag gatcgggcct tgatgttacc cgagagcttg   1740
gcacccagcc tgcgcgagca ggggaattaa ttcccacggg ttttgctgcc cgcaaacggg   1800
ctgttctggt gttgctagtt tgttatcaga atcgcagatc cggcttcagc cggtttgccg   1860
gctgaaagcg ctatttcttc cagaattgcc atgattttttt ccccacggga ggcgtcactg   1920
gctcccgtgt tgtcggcagc tttgattcga taagcagcat cgcctgtttc aggctgtcta   1980
tgtgtgactt tgagctgta acaagttgtc tcaggtgttc aatttcatgt tctagttgct   2040
ttgtttttact ggtttcacct gttctattag gtgttacatg ctgttcatct gttacattgt   2100
cgatctgttc atggtgaaca gctttgaatg caccaaaaac tcgtaaaagc tctgatgtat   2160
ctatctttt tacaccgttt tcatctgtgc atatggacag ttttcccttt gatatgtaac   2220
ggtgaacagt tgttctactt tgtttgtta gtcttgatgc ttcactgata gatacaagag   2280
ccataagaac ctcagatcct tccgtattta gccagtatgt tctctagtgt ggttcgttgt   2340
ttttgcgtga gccatgagaa cgaaccattg agatcatact tactttgcat gtcactcaaa   2400
aattttgcct caaaactggt gagctgaatt tttgcagtta aagcatcgtg tagtgttttt   2460
cttagtccgt tatgtaggta ggaatctgat gtaatggttg ttggtatttt gtcaccattc   2520
atttttatct ggttgttctc aagttcggtt acgagatcca tttgtctatc tagttcaact   2580
tggaaaatca acgtatcagt cgggcggcct cgcttatcaa ccaccaattt catattgctg   2640
taagtgttta atctttact tattggtttc aaaacccatt ggttaagcct tttaaactca   2700
tggtagttat tttcaagcat taacatgaac ttaaattcat caaggctaat ctctatattt   2760
gccttgtgag ttttctttttg tgttagttct tttaataacc actcataaat cctcatagag   2820
```

```
tatttgtttt caaaagactt aacatgttcc agattatatt ttatgaattt ttttaactgg    2880
aaaagataag gcaatatctc ttcactaaaa actaattcta attttcgct tgagaacttg    2940 gcatagtttg tccactggaa aatctcaaag cctttaacca aaggattcct gatttccaca    3000
gttctcgtca tcagctctct ggttgcttta gctaatacac cataagcatt ttccctactg    3060
atgttcatca tctgagcgta ttggttataa gtgaacgata ccgtccgttc tttccttgta    3120
gggttttcaa tcgtggggtt gagtagtgcc acacagcata aaattagctt ggtttcatgc    3180
tccgttaagt catagcgact aatcgctagt tcatttgctt tgaaaacaac taattcagac    3240
atacatctca attggtctag gtgattttaa tcactatacc aattgagatg ggctagtcaa    3300
tgataattac tagtcctttt cctttgagtt gtgggtatct gtaaattctg ctagaccttt    3360
gctggaaaac ttgtaaattc tgctagaccc tctgtaaatt ccgctagacc tttgtgtgtt    3420
ttttttgttt atattcaagt ggttataatt tatagaataa agaaagaata aaaaaagata    3480
aaagaaatag atcccagccc tgtgtataac tcactacttt agtcagttcc gcagtattac    3540
aaaaggatgt cgcaaacgct gtttgctcct ctacaaaaca gaccttaaaa ccctaaaggc    3600
ttaagtagca ccctcgcaag ctcgggcaaa tcgctgaata ttccttttgt ctccgaccat    3660
caggcacctg agtcgctgtc ttttcgtga cattcagttc gctgcgctca cggctctggc    3720
agtgaatggg ggtaaatggc actacaggcg ccttttatgg attcatgcaa ggaaactacc    3780
cataatacaa gaaaagcccg tcacgggctt ctcagggcgt tttatggcgg gtctgctatg    3840
tggtgctatc tgacttttg ctgttcagca gttcctgccc tctgattttc cagtctgacc    3900
acttcggatt atcccgtgac aggtcattca gactggctaa tgcacccagt aaggcagcgg    3960
tatcatcaac aggcttaccc gtcttactgt cgggaattca tttaaatagt caaaagcctc    4020
cgaccggagg cttttgactg ctaggcgatc tgtgctgttt gccacggtat gcagcaccag    4080
cgcgagatta tgggctcgca cgctcgactg tcggacgggg gcactggaac gagaagtcag    4140
gcgagccgtc acgcccttga caatgccaca tcctgagcaa ataattcaac cactaaacaa    4200
atcaaccgcg tttcccggag gtaaccaagc ttgcgggaga aatgatgaa caagagccaa    4260 caagttcaga caatcaccct ggccgccgcc cagcaaatgg cggcggcggt ggaaaaaaaa    4320
gccactgaga tcaacgtggc ggtggtgttt tccgtagttg accgcggagg caacacgctg    4380
cttatccagc ggatggacga ggccttcgtc tccagctgcg atatttccct gaataaagcc    4440
tggagcgcct gcagcctgaa gcaaggtacc catgaaatta cgtcagcggt ccagccagga    4500
caatctctgt acggtctgca gctaaccaac caacagcgaa ttattatttt tggcggcggc    4560
ctgccagtta tttttaatga gcaggtaatt ggcgccgtcg gcgttagcgg cggtacggtc    4620
gagcaggatc aattattagc ccagtgcgcc ctggattgtt tttccgcatt ataacctgaa    4680
gcgagaaggt atattatgag ctatcgtatg ttccgccagg cattctgagt gttaacgagg    4740
ggaccgtcat gtcgctttca ccgccaggcg tacgcctgtt ttacgatccg cgcgggcacc    4800
atgccggcgc catcaatgag ctgtgctggg ggctggagga gcaggggtc ccctgccaga    4860 ccataaccta tgacgaggc ggtgacgccg ctgcgctggg cgccctggcg ccagaaagct    4920 cgccctgcg ggtgggtatc gggctcagcg cgtccggcga gatagccctc actcatgccc    4980
agctgccggc ggacgcgccg ctggctaccg gacacgtcac cgatagcgac gatcaactgc    5040
gtacgctcgg cgccaacgcc gggcagctgg ttaaagtcct gccgttaagt gagagaaact    5100
gaatgtatcg tatctatacc cgcaccgggg ataaggcac caccgccctg tacgcggca    5160 gccgcatcga gaaagaccat attcgcgtcg aggcctacgg caccgtcgat gaactgatat    5220
```

```
cccagctggg cgtctgctac gccacgaccc gcgacgccgg gctgcgggaa agcctgcacc    5280
atattcagca gacgctgttc gtgctggggg ctgaactggc cagcgatgcg cggggcctga    5340
cccgcctgag ccagacgatc ggcgaagagg agatcaccgc cctggagcgg cttatcgacc    5400
gcaatatggc cgagagcggc ccgttaaaac agttcgtgat cccggggagg aatctcgcct    5460
ctgcccagct gcaccctgat gcttgcgctt gaactggcct agcaaacaca gaaaaaagcc    5520
cgcacctgac agtgcgggct ttttttttcc taggcgatct gtgctgtttg ccacggtatg    5580
cagcaccagc gcgagattat gggctcgcac gctcgactgt cggacggggg cactggaacg    5640
agaagtcagg cgagccgtca cgcccttgac aatgccacat cctgagcaaa taattcaacc    5700
actaaacaaa tcaaccgcgt ttcccggagg taaccaagct tcacctttg agccgatgaa     5760 caatgaaaag atcaaaacga tttgcagtac tggcccagcg ccccgtcaat caggacgggc    5820
tgattggcga gtggcctgaa gaggggctga tcgccatgga cagccccttt gacccggtct    5880
cttcagtaaa agtggacaac ggtctgatcg tcgaactgga cggcaaacgc cgggaccagt    5940
ttgacatgat cgaccgattt atcgccgatt acgcgatcaa cgttgagcgc acagagcagg    6000
caatgcgcct ggaggcggtg gaaatagccc gtatgctggt ggatattcac gtcagccggg    6060
aggagatcat tgccatcact accgccatca cgccggccaa agcggtcgag gtgatggcgc    6120
agatgaacgt ggtggagatg atgatggcgc tgcagaagat gcgtgcccgc cggaccccct    6180
ccaaccagtg ccacgtcacc aatctcaaag ataatccggt gcagattgcc gctgacgccg    6240
ccgaggccgg gatccgcggc ttctcagaac aggagaccac ggtcggtatc gcgcgctacg    6300
cgccgtttaa cgccctggcg ctgttggtcg gttcgcagtg cggccgcccc ggcgtgttga    6360
cgcagtgctc ggtggaagag gccaccgagc tggagctggg catgcgtggc ttaaccagct    6420
acgccgagac ggtgtcggtc tacggcaccg aagcggtatt taccgacggc gatgatacgc    6480
cgtggtcaaa ggcgttcctc gcctcggcct acgcctcccg cgggttgaaa atgcgctaca    6540
cctccggcac cggatccgaa gcgctgatgg gctattcgga gagcaagtcg atgctctacc    6600
tcgaatcgcg ctgcatcttc attactaaag gcgccggggt tcagggactg caaaacggcg    6660
cggtgagctg tatcggcatg accggcgctg tgccgtcggg cattcgggcg gtgctggcgg    6720
aaaacctgat cgcctctatg ctcgacctcg aagtggcgtc cgccaacgac cagactttct    6780
cccactcgga tattcgccgc accgcgcgca ccctgatgca gatgctgccg ggcaccgact    6840 ttatttctc cggctacagc gcggtgccga actacgacaa catgttcgcc ggctcgaact    6900
tcgatgcgga agattttgat gattacaaca tcctgcagcg tgacctgatg gttgacggcg    6960
gcctgcgtcc ggtgaccgag gcggaaacca ttgccattcg ccagaaagcg cgcgggcga    7020 tccaggcggt tttccgcgag ctggggctgc cgccaatcgc cgacgaggag gtggaggccg    7080
ccacctacgc gcacggcagc aacgagatgc cgccgcgtaa cgtggtggag gatctgagtg    7140
cggtggaaga gatgatgaag cgcaacatca ccggcctcga tattgtcggc gcgctgagcc    7200
gcagcggctt tgaggatatc gccagcaata ttctcaatat gctgcgccag cgggtcaccg    7260
gcgattacct gcagacctcg gccattctcg atcggcagtt cgaggtggtg agtgcggtca    7320
acgacatcaa tgactatcag gggcgggca ccggctatcg catctctgcc gaacgctggg    7380
cggagatcaa aaatattccg ggcgtggttc agcccgacac cattgaataa ggcggtattc    7440
ctgtgcaaca gacaacccaa attcagccct cttttaccct gaaaaccgcg agggcgggg    7500 tagcttctgc cgatgaacgc gccgatgaag tggtgatcgg cgtcggccct gccttcgata    7560
```

```
aacaccagca tcacactctg atcgatatgc cccatggcgc gatcctcaaa gagctgattg   7620
ccggggtgga agaagagggg cttcacgccc gggtggtgcg cattctgcgc acgtccgacg   7680
tctcctttat ggcctgggat gcggccaacc tgagcggctc ggggatcggc atcggtatcc   7740
agtcgaaggg gaccacggtc atccatcagc gcgatctgct gccgctcagc aacctggagc   7800
tgttctccca ggcgccgctg ctgacgctgg agacctaccg gcagattggc aaaaacgctg   7860
cgcgctatgc gcgcaaagag tcaccttcgc cggtgccggt ggtgaacgat cagatggtgc   7920
ggccgaaatt tatggccaaa gccgcgctat ttcatatcaa agagaccaaa catgtggtgc   7980
aggacgccga gcccgtcacc ctgcacatcg acttagtaag ggagtgacca tgagcgagaa   8040
aaccatgcgc gtgcaggatt atccgttagc cacccgctgc ccggagcata tcctgacgcc   8100
taccggcaaa ccattgaccg atattaccct cgagaaggtg ctctctggcg aggtgggccc   8160
gcaggatgtg cggatctccc gccagaccct tgagtaccag gcgcagattg ccgagcagat   8220
gcagcgccat gcggtggcgc gcaatttccg ccgcgcggcg gagcttatcg ccattcctga   8280
cgagcgcatt ctggctatct ataacgcgct gcgcccgttc cgctcctcgc aggcggagct   8340
gctggcgatc gccgacgagc tggagcacac ctggcatgcg acagtgaatg ccgcctttgt   8400
ccgggagtcg gcggaagtgt atcagcagcg gcataagctg cgtaaaggaa gctaagcgga   8460
ggtcagcatg ccgttaatag ccgggattga tatcggcaac gccaccaccg aggtggcgct   8520
ggcgtccgac tacccgcagg cgagggcgtt tgttgccagc gggatcgtcg cgacgacggg   8580
catgaaaggg acgcgggaca atatcgccgg gaccctcgcc gcgctggagc aggccctggc   8640
gaaaacaccg tggtcgatga gcgatgtctc tcgcatctat cttaacgaag ccgcgccggt   8700
gattggcgat gtggcgatgg agaccatcac cgagaccatt atcaccgaat cgaccatgat   8760
cggtcataac ccgcagacgc cgggcggggt gggcgttggc gtggggacga ctatcgccct   8820 cggggcggctg gcgacgctgc cggcggcgca gtatgccgag gggtggatcg tactgattga   8880
cgacgccgtc gatttccttg acgccgtgtg gtggctcaat gaggcgctcg accgggggat   8940
caacgtggtg gcggcgatcc tcaaaaagga cgacggcgtg ctggtgaaca accgcctgcg   9000
taaaaccctg ccggtggtgg atgaagtgac gctgctggag caggtccccg aggggtaat   9060 ggcggcggtg gaagtggccg cgccgggcca ggtggtgcgg atcctgtcga atccctacgg   9120
gatcgccacc ttcttcgggc taagcccgga agagacccag gccatcgtcc ccatcgcccg   9180
cgccctgatt ggcaaccgtt ccgcggtggt gctcaagacc ccgcagggggg atgtgcagtc   9240 gcgggtgatc ccggcgggca acctctacat tagcggcgaa aagcgccgcg gagaggccga   9300
tgtcgccgag ggcgcggaag ccatcatgca ggcgatgagc gcctgcgctc cggtacgcga   9360
catccgcggc gaaccgggca cccacgccgg cggcatgctt gagcgggtgc gcaaggtaat   9420
ggcgtccctg accggccatg agatgagcgc gatatacatc caggatctgc tggcggtgga   9480
tacgtttatt ccgcgcaagg tgcagggcgg gatggccggc gagtgcgcca tggagaatgc   9540
cgtcgggatg gcggcgatgg tgaaagcgga tcgtctgcaa atgcaggtta tcgcccgcga   9600
actgagcgcc cgactgcaga ccgaggtggt ggtgggcggc gtggaggcca acatggccat   9660
cgccggggcg ttaaccactc ccggctgtgc ggcgccgctg gcgatcctcg acctcggcgc   9720
cggctcgacg gatgcggcga tcgtcaacgc ggaggggcag ataacggcgg tccatctcgc   9780
cggggcgggg aatatggtca gcctgttgat taaaaccgag ctgggcctcg aggatctttc   9840
gctggcggaa gcgataaaaa aatacccgct ggccaaagtg gaaagcctgt tcagtattcg   9900
tcacgagaat ggcgcggtgg agttctttcg ggaagccctc agcccggcgg tgttcgccaa   9960
```

```
agtggtgtac atcaaggagg gcgaactggt gccgatcgat aacgccagcc cgctggaaaa  10020
aattcgtctc gtgcgccggc aggcgaaaga gaaagtgttt gtcaccaact gcctgcgcgc  10080
gctgcgccag gtctcacccg gcggttccat tcgcgatatc gcctttgtgg tgctggtggg  10140
cggctcatcg ctggactttg agatcccgca gcttatcacg gaagccttgt cgcactatgg  10200
cgtggtcgcc gggcagggca atattcgggg aacagaaggg ccgcgcaatg cggtcgccac  10260
cgggctgcta ctggccggtc aggcgaatta acgggcgct cgcgccagcc tctaggtaca  10320
aataaaaaag gcacgtcaga tgacgtgcct tttttcttgt ctagcgtgca ccaatgcttc  10380
tggcgtcagg cagccatcgg aagctgtggt atggctgtgc aggtcgtaaa tcactgcata  10440
attcgtgtcg ctcaaggcgc actcccgttc tggataatgt ttttgcgcc gacatcataa  10500
cggttctggc aaatattctg aaatgagctg ttgacaatta atcatccggc tcgtataatg  10560
tgtggaattg tgagcggata acaatttcac acaggaaaca gaccatgact agtaaggagg  10620
acaattccat ggctgctgct gctgatagat taaacttaac ttccggccac ttgaatgctg  10680
gtagaaagag aagttcctct tctgtttctt tgaaggctgc cgaaaagcct ttcaaggtta  10740
ctgtgattgg atctggtaac tggggtacta ctattgccaa ggtggttgcc gaaaattgta  10800
agggataccc agaagttttc gctccaatag tacaaatgtg ggtgttcgaa gagagatca  10860
atggtgaaaa attgactgaa atcataaata ctagacatca aaacgtgaaa tacttgcctg  10920
gcatcactct acccgacaat ttggttgcta atccagactt gattgattca gtcaaggatg  10980
tcgacatcat cgtttttcaac attccacatc aattttttgcc ccgtatctgt agccaattga  11040
aaggtcatgt tgattcacac gtcagagcta tctcctgtct aaagggtttt gaagttggtg  11100
ctaaaggtgt ccaattgcta tcctcttaca tcactgagga actaggtatt caatgtggtg  11160
ctctatctgg tgctaacatt gccaccgaag tcgctcaaga acactggtct gaaacaacag  11220
ttgcttacca cattccaaag gatttcagag gcgagggcaa ggacgtcgac cataaggttc  11280
taaaggcctt gttccacaga ccttacttcc acgttagtgt catcgaagat gttgctggta  11340
tctccatctg tggtgctttg aagaacgttg ttgccttagg ttgtggtttc gtcgaaggtc  11400
taggctgggg taacaacgct tctgctgcca tccaaagagt cggtttgggt gagatcatca  11460
gattcggtca aatgttttc ccagaatcta gagaagaaac atactaccaa gagtctgctg  11520
gtgttgctga tttgatcacc acctgcgctg gtggtagaaa cgtcaaggtt gctaggctaa  11580
tggctacttc tggtaaggac gcctgggaat gtgaaaagga gttgttgaat ggccaatccg  11640
ctcaaggttt aattacctgc aaagaagttc acgaatggtt ggaaacatgt ggctctgtcg  11700
aagacttccc attatttgaa gccgtatacc aaatcgttta caacaactac ccaatgaaga  11760
acctgccgga catgattgaa gaattagatc tacatgaaga ttagatttat tggatccagg  11820
aaacagacta gaattatggg attgactact aaacctctat ctttgaaagt taacgccgct  11880
ttgttcgacg tcgacggtac cattatcatc tctcaaccag ccattgctgc attctggagg  11940
gatttcggta aggacaaacc ttatttcgat gctgaacacg ttatccaagt ctcgcatggt  12000
tggagaacgt ttgatgccat tgctaagttc gctccagact ttgccaatga agagtatgtt  12060
aacaaattag aagctgaaat tccggtcaag tacggtgaaa aatccattga agtcccaggt  12120
gcagttaagc tgtgcaacgc tttgaacgct ctaccaaaag agaaatgggc tgtggcaact  12180
tccggtaccc gtgatatggc acaaaaatgg ttcgagcatc tgggaatcag gagaccaaag  12240
tacttcatta ccgctaatga tgtcaaacag ggtaagcctc atccagaacc atatctgaag  12300
```

```
                                                                    -continued ggcaggaatg gcttaggata tccgatcaat gagcaagacc cttccaaatc taaggtagta    12360
gtatttgaag acgctccagc aggtattgcc gccggaaaag ccgccggttg taagatcatt    12420
ggtattgcca ctactttcga cttggacttc ctaaaggaaa aaggctgtga catcattgtc    12480
aaaaaccacg aatccatcag agttggcggc tacaatgccg aaacagacga agttgaattc    12540
atttttgacg actacttata tgctaaggac gatctgttga aatggtaacc cgggctgcag    12600
gcatgcaagc ttggctgttt tggcggatga gagaagattt tcagcctgat acagattaaa    12660
tcagaacgca gaagcggtct gataaaacag aatttgcctg gcggcagtag cgcggtggtc    12720
ccacctgacc ccatgccgaa ctcagaagtg aaacgccgta gcgccgatgg tagtgtgggg    12780
tctccccatg cgagagtagg gaactgccag gcatcaaata aaacgaaagg ctcagtcgaa    12840
agactgggcc tttcgtttta tctgttgttt gtcggtgaac gctctcctga gtaggacaaa    12900
tccgccggga gcggatttga acgttgcgaa gcaacggccc ggagggtggc gggcaggacg    12960
cccgccataa actgccaggc atcaaattaa gcagaaggcc atcctgacgg atggcctttt    13020
tgcgtttcta caaactccag ctggatcggg cgctagagta tacatttaaa tggtaccctc    13080
tagtcaaggc cttaagtgag tcgtattacg gactggccgt cgttttacaa cgtcgtgact    13140
gggaaaaccc tggcgttacc caacttaatc gccttgcagc acatccccct ttcgccagct    13200
ggcgtaatag cgaagaggcc cgcaccgatc gcccttccca acagttgcgc agcctgaatg    13260
gcgaatggcg cctgatgcgg tattttctcc ttacgcatct gtgcggtatt tcacaccgca    13320
tatggtgcac tctcagtaca atctgctctg atgccgcata gttaagccag ccccgacacc    13380
cgccaacacc cgctgacgag ct                                             13402
```